US007884256B2

(12) United States Patent
Liu et al.

(10) Patent No.: US 7,884,256 B2
(45) Date of Patent: *Feb. 8, 2011

(54) POLYMERIZABLE HIGHER DIAMONDOID DERIVATIVES

(75) Inventors: Shenggao Liu, Hercules, CA (US); Robert M. Carlson, Petaluma, CA (US); Jeremy E. Dahl, Palo Alto, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 1657 days.

This patent is subject to a terminal disclaimer.

(21) Appl. No.: 11/013,638

(22) Filed: Dec. 17, 2004

(65) Prior Publication Data

US 2005/0159634 A1 Jul. 21, 2005

Related U.S. Application Data

(62) Division of application No. 10/046,486, filed on Jan. 16, 2002, now Pat. No. 6,858,700.

(60) Provisional application No. 60/262,842, filed on Jan. 19, 2001, provisional application No. 60/348,032, filed on Oct. 26, 2001.

(51) Int. Cl.
C07C 13/00 (2006.01)

(52) U.S. Cl. .............................. 585/17; 585/7; 585/10; 585/12; 585/25

(58) Field of Classification Search .................. 585/7, 585/10, 12, 17, 25
See application file for complete search history.

(56) References Cited

U.S. PATENT DOCUMENTS

| 3,457,318 A | 7/1969 | Capaldi |
| 3,832,332 A | 8/1974 | Thompson |
| 4,142,036 A | 2/1979 | Feinstein |
| 4,952,748 A | 8/1990 | Alexander |
| 4,952,749 A | 8/1990 | Alexander |
| 4,952,757 A | 8/1990 | Purcell et al. |
| 4,982,049 A | 1/1991 | Alexander |
| 5,015,758 A | 5/1991 | Pilgrim et al. |
| 5,017,734 A | 5/1991 | Baum |
| 5,019,660 A | 5/1991 | Chapman et al. |
| 5,019,665 A | 5/1991 | Partridge |
| 5,053,434 A | 10/1991 | Chapman |
| 5,238,705 A | 8/1993 | Hayashi et al. |
| 5,245,104 A | 9/1993 | Cullick |
| 5,256,391 A | 10/1993 | Chen et al. |
| 5,268,513 A | 12/1993 | Shen |
| 5,298,666 A | 3/1994 | Shen |
| 5,306,851 A | 4/1994 | Wu |
| 5,308,661 A | 5/1994 | Feng et al. |
| 5,347,063 A | 9/1994 | Shen |
| 5,367,051 A | 11/1994 | Narang et al. |
| 5,369,213 A | 11/1994 | Shen |
| 5,380,947 A | 1/1995 | Chen |
| 5,382,684 A | 1/1995 | Moini |
| 5,397,488 A | 3/1995 | Chen |
| 5,410,092 A | 4/1995 | Shen |
| 5,414,189 A | 5/1995 | Chen |
| 5,416,188 A | 5/1995 | Chiang et al. |
| 5,430,193 A | 7/1995 | Shen |
| 5,449,531 A | 9/1995 | Zhu et al. |
| 5,455,072 A | 10/1995 | Bension et al. |
| 5,461,184 A | 10/1995 | Swanson |
| 5,462,680 A | 10/1995 | Brois et al. |
| 5,462,776 A | 10/1995 | Gruen |
| 5,498,812 A | 3/1996 | Bradway |
| 5,576,355 A | 11/1996 | Chen |
| 5,635,581 A | 6/1997 | Chiang et al. |
| 5,695,847 A | 12/1997 | Browne |
| 5,739,376 A | 4/1998 | Bingel |
| 5,861,135 A | 1/1999 | Tanabe et al. |
| 5,874,175 A | 2/1999 | Li |
| 5,880,154 A | 3/1999 | Boukrinskaia |
| 6,080,470 A | 6/2000 | Dorfman |
| 6,162,412 A | 12/2000 | Fujimori |
| 6,235,851 B1 | 5/2001 | Ishii |
| 6,300,410 B1 | 10/2001 | Shachat et al. |
| 6,743,290 B2 * | 6/2004 | Dahl et al. ..................... 117/68 |
| 6,812,370 B2 * | 11/2004 | Dahl et al. ................. 585/352 |
| 6,815,569 B1 * | 11/2004 | Dahl et al. ................. 585/352 |
| 6,831,202 B2 * | 12/2004 | Dahl et al. ................. 585/352 |
| 6,843,851 B2 * | 1/2005 | Dahl et al. ..................... 117/68 |

(Continued)

FOREIGN PATENT DOCUMENTS

EP 0399851 11/1996

(Continued)

OTHER PUBLICATIONS

Aczel, et al., "Stability of Adamantane and its Derivatives to Coal-liquefaction Conditions, and its implications toward the organic structure of Coal", *Fuel*, vol. 58, pp. 228-230, (Mar. 1979).

(Continued)

*Primary Examiner*—Elizabeth D Wood
(74) *Attorney, Agent, or Firm*—Merchant & Gould

(57) ABSTRACT

Higher diamondoid derivatives capable of taking part in polymerization reactions are disclosed as well as intermediates to these derivatives, polymers formed from these derivatives and methods for preparing the polymers.

64 Claims, 59 Drawing Sheets

U.S. PATENT DOCUMENTS 7,034,194 B2 * 4/2006 Dahl et al. .................. 585/352

FOREIGN PATENT DOCUMENTS

| WO | WO 92/13909 | 8/1992 |
| WO | WO 95/06019 | 3/1995 |
| WO | WO 95/11472 | 4/1995 |

OTHER PUBLICATIONS

Badziag, P., et al., "Nanometre-sized Diamonds are More Stable than Graphite", Nature, vol. 343, pp. 244-245, and 517, (1990).
Bagrii, Ye, et al., "Catalytic Breakdown of Paraffinic Hydrocarbons in the Presence of Adamantanes", Petrol. Chem USSR, vol. 30, No. 2, pp. 131-134, (1990).
Balaban, et al., Systemic Classification and Nomenclature of Diamond Hydrocarbons-I, Tetrahedron, 34, pp. 3599-3606, (1978).
Baughman, GL, "Dibromination of Adamantane", Publication Unknown, vol. 29, pp. 238-240 (Jan. 1964).
Bingham, RC, et al., "Recent Developments in the Chemistry of Adamantane and Related Polycyclic Hydrocarbons", Chemistry of Adamantanes, Ch. 18, pp. 1-101 (1970).
Bott, Von K., "Synthese von Adamantan-und Norbornan chloressigsauren mit Trichlorathylen", Angew. Chem., vol. 79, pp. 943-945 (1967).
Broich, F., "Carbonsauresynthesen mit 1,1-Dichlorathylen", Angew. chem., vol. 78, pp. 932-936 (1966).
Cammas, S., et al., "Poly($\beta$-malic acid): Obtaining High Molecular Weights by Improvement of the Synthesis Route", Polymer, vol. 37, No. 18, pp. 4215-4220 (1996).
Chung, et al., Recent Development in High-Energy Density Liquid Fuels, Energy and Fuels, 13, pp. 641-649, (1999).
Courtney, T., et al., "The Chemistry of Diamantane: Part 1—Synthesis and Some Functionalisation Reactions", J.C.S.Perkin I, pp. 2691-2696 (1972).
Dahl, J., et al., Diamondoid Hydrocarbons as Indicators of Natural Oil Cracking, Nature, 399, pp. 54-57, (1999).
Drexler, Eric K., Nanosystems: Molecular Machinery Manufacturing and Computation, John Wiley & Sons, pp. 238-249, (1992).
Fort, Jr., et al., Adamantane: Consequences of the Diamondoid Structure, Chem. Rev., 64, pp. 277-300, (1964).
Haaf, W., "Untersuchungen uber die Ritter-Reacktion", pp. 3359-3369 (1963).
Hala, V.S., et al., "Analyse Unds erwendung on Pyrolyseol", Jahrgang, pp. 85-87, (Feb. 1971) in German—English Abstract on p. 85.
Koch, H., "Direkte Syntese der Adamantan-carbonsaure-(1)", Eingengangen Am., 29, p. Z 944 (1960).
Landa, S., "Adamantane and Its Homologues", Current Science, V. 52, pp. 485-489 (1963).
Liaw, Der-Jang, et al., "Synthesis and Characterization of new Polyamides and Polyimides Prepared from 2,2-bix[4-(4-aminophenoxy)phenyl]adamantane", Macromol. Chem. Phys., 200, No. 6, pp. 1326-1332 (1999).
Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, Fuel, 74:10, pp. 1512-1521, (1995).
Machacek, V., et al., "Let Od Objeveni Adamantanu", Chemicke Listy/svazek, pp. 753-761, (1982) Russian—English Abstract on p. 761.
McKervey, Synthetic Approaches to Large Diamondoid Hydrocarbonds, Tetrahedron, 36, pp. 971-992, (1980).
Moine, L., et al., "Polymers of Malic Acid Conjugated with the 1-adamantyl Moiety as Lipophilic Pendant Group", Polymer, vol. 38, No. 12, pp. 3121-3127 (1997).
Moiseev, IK, et al., "Reactions of Adamantanes in Electrophilic Media", Russian Chem. Reviews, vol. 68, No. 12, pp. 1001-1120 (1999).
Neavel, R., "Liquefaction of Coalinhydrogen-donor and Non-donor Vehicles", Fuel, vol. 55, pp. 237-242 (1976).
Oya, A, et al., "Carbonization of Adamantanes to a Graphitizable Carbon", Fuel, vol. 60, pp. 667-669, (Aug. 1981).
Petrov, A., "Hydrocarbons of Adamantane Series as Indicies of Petroleum Catagenesis Process", Advances in Organic Geo Chemistry, 6th International Meeting on Organic Geochemistry, pp. 517-522 (1973).
Prusova, D., Liquid Chromatography of Adamantanes and Carbon Adsorbents, J. Chrom, 234, pp. 1-11, (1982).
Rollman, L., et al., "Adamantanes From Petroleum, with Zeolites", American Chemical Study, 210th ACS National Meeting, Abstract and paper, Aug. 20, 1995).
Sandia National Laboratories (2000), World's First Diamond Micromachines Created at Sandia, Press Release, (Feb. 22, 2000), www.Sandia.gov.
Shen, M., et al., Finite $T_d$ Symmetry Models for Diamond: From Adamantane to Superadamantane ($C_{35}H_{36}$), J. Am., Chem. Soc., vol. 114, No. 2, pp. 497-505, (1992).
Smith, G., et al., "Some Reactions of Adamantane and Adamantane Derivatives", publication unknown, vol. 26, pp. 2207-2212 (1961).
Stetter, H., et al., "Monofunktionelle Adamantan-Derivate", Angew. Chem., 71, pp. 429-430 (1959).
Supryadkina, NY, et al., "Catalytic Dealkylation of Alkyladamantanes", Petrol. Chem., USSR, vol. 28, No. 2, pp. 103-110, (1988).
Tominaga, K., et al., "Next-generation Fine Chemicals Raw Material-Adamantane", Chem Econ & Eng. Review, vol. 17, No. 10, pp. 23-29, (Oct. 1985).
Vodicka, L, et al., "High Performance Liquid Chromatography of Halogeno Derivatives of Adamantane and Diamantane", J. Chrom, 270, pp. 199-205, (1983).
von Schleyer, P., et al., "Nonacyclo[11.7.1.1$^{2,18}$.0$^{3,16}$.0$^{4,13}$.0$^{5,10}$.0$^{6,14}$.0$^{7,11}$.0$^{15,20}$]-Docosane, a Bastard Tetramantane", J. of the Am. Chem. Soc., 90:8, letter to the editor, Aug. 28, 1968.
von R. Schleyer, P., et al., "The Preparation and Reactivity of 2-Substituted Derivatives", Frick Chemical Laboratory, vol. 83, pp. 182-187 (1961).
Wingert, W., "G.c.-m.s. Analysis of Diamondoid Hydrocarbons in Smackover Petroleums", Fuel, vol. 71, pp. 37-42, (Jan. 1992).

* cited by examiner

FIG. 1B
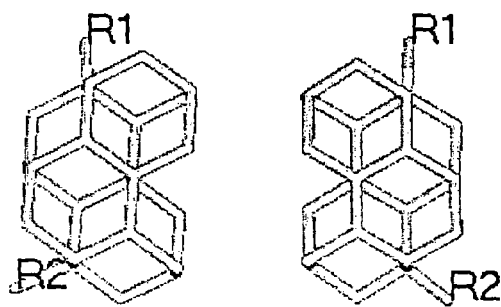
Enantiomeric [123] Tetramantanes
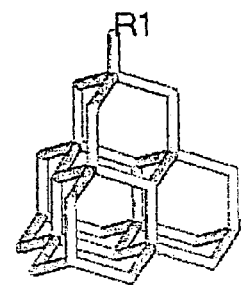
[1(2,3)4] Pentamantane
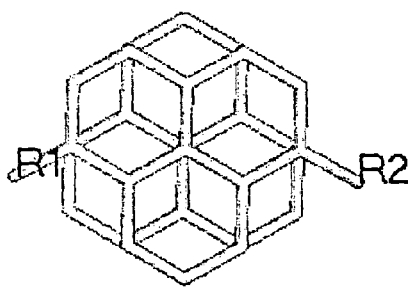
[12312] Hexamantane
(Cyclohexamantane)
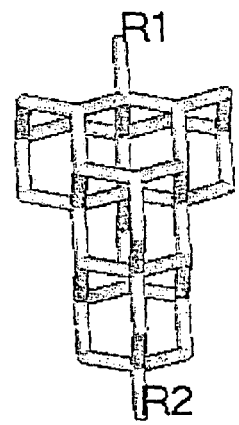
[121(3)4] Hexamantane
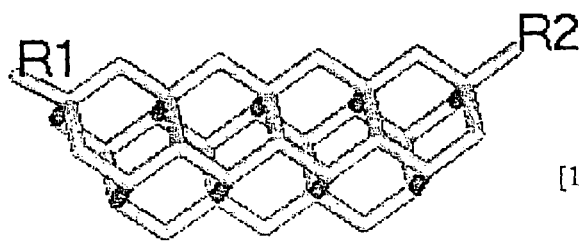
[121212] Heptamantanes FIG. 1B
(continued)
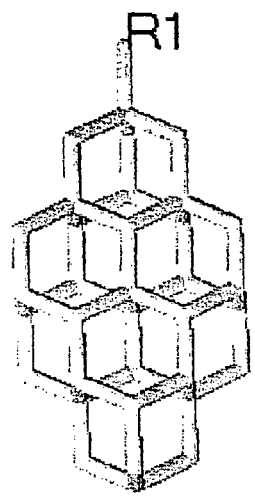
[1213(1)21] Octamantane
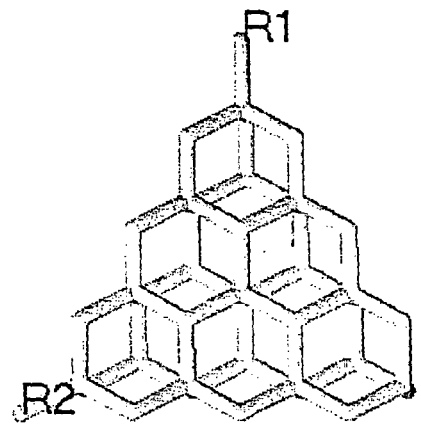
[121(2)32(1)3] Nonamantane
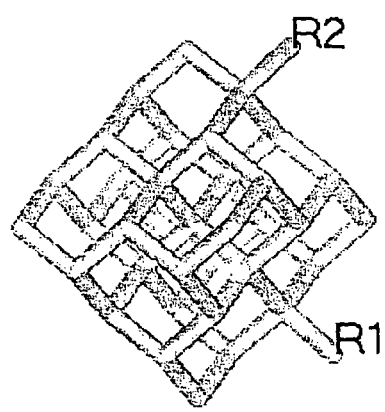
[1231241(2)3] Decamantane
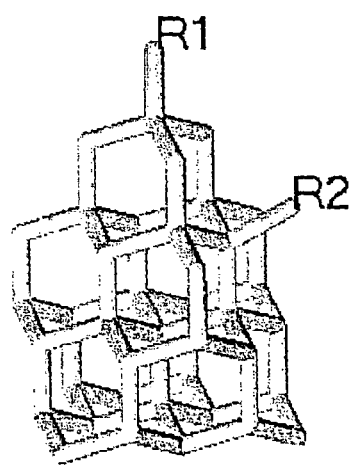
[123(1,2)42143] Undecamantane

FIG. 2B

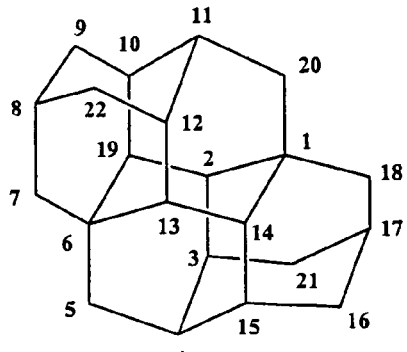

[121] Tetramantane (*anti-*)
4 non-equivalent tertiary carbons:

4, 11 (equivalent)
8, 17 (equivalent)
3, 10, 12, 15 (equivalent)
2, 13, 14, 19 (equivalent)

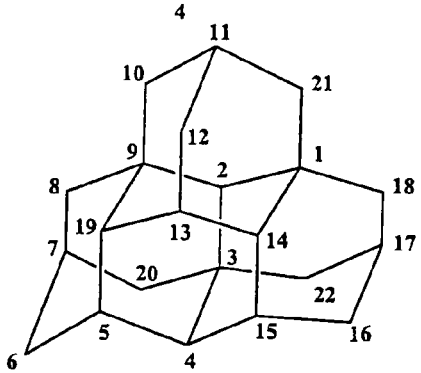

[1[2]3] Tetramantane (*iso-*)
4 non-equivalent tertiary carbons:

2
4, 14, 19 (equivalent)
5, 13, 15 (equivalent)
7, 11, 17 (equivalent)

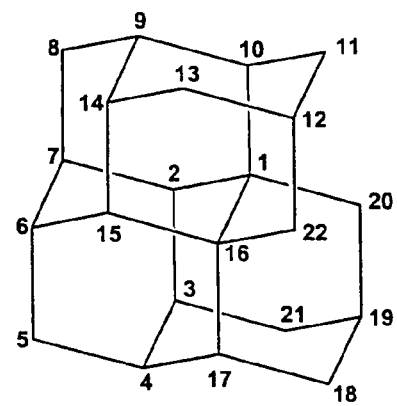

[123]A Tetramantane (*skew-* A)
6 non-equivalent tertiary carbons:

6, 7 (equivalent)
4, 9 (equivalent)
3, 14 (equivalent)
2, 15 (equivalent)
10, 17 (equivalent)
12, 19 (equivalent)

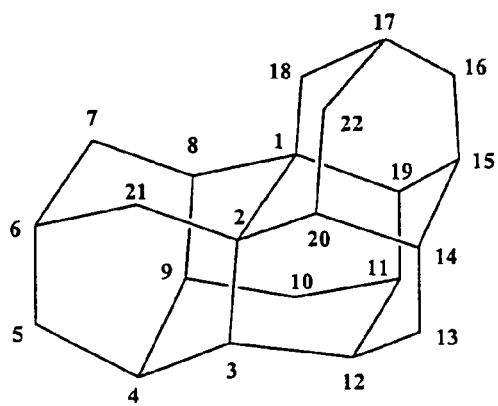

[123]B Tetramantane (*skew-* B)
6 non-equivalent tertiary carbons:

6, 17 (equivalent)
4, 15 (equivalent)
11, 12 (equivalent)
3, 19 (equivalent)
9, 14 (equivalent)
8, 20 (equivalent)

Pentamantane

Hexamantane

Octamantane

Undecamantane

FIG. 4I
Polyvinyl
D-CH=CH$_2$ monomer 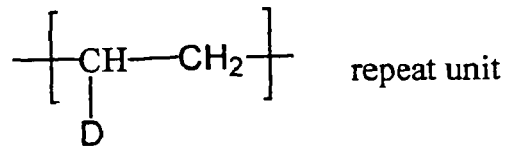 repeat unit
Further vinyl addition polymers
isobutylene    D-CH=C(CH$_3$)$_2$ 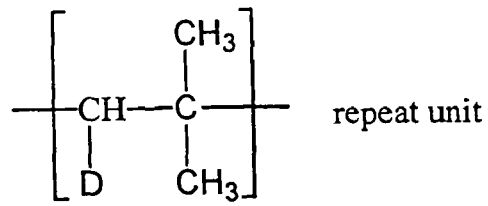 repeat unit
acryonitrile    D-CH=CH-CN 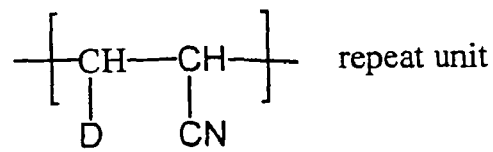 repeat unit
vinylchloride    D-CH=CH-Cl 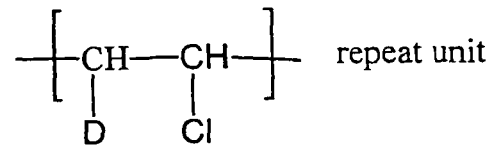 repeat unit
acrylates 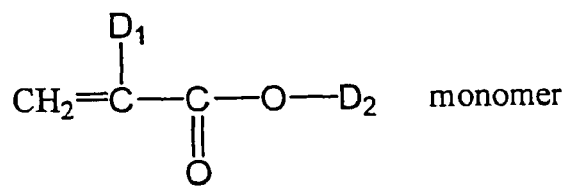 monomer
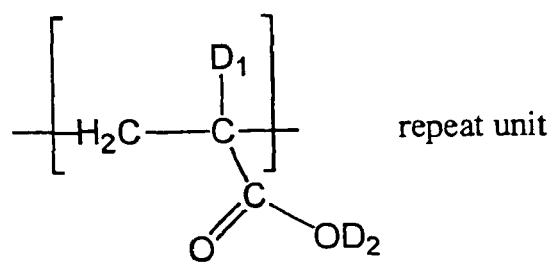 repeat unit

FIG. 4I (cont.)
Further addition polymers
Polyethylene oxide 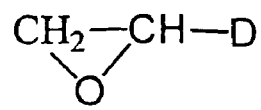 monomer
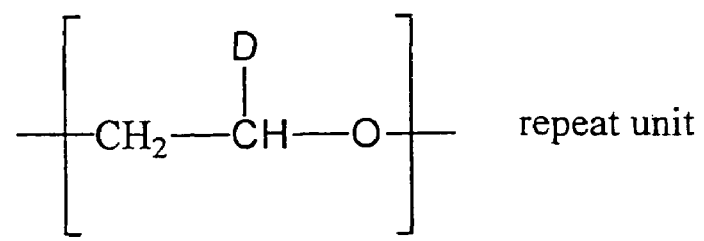 repeat unit
Polyacetaldehyde  monomer
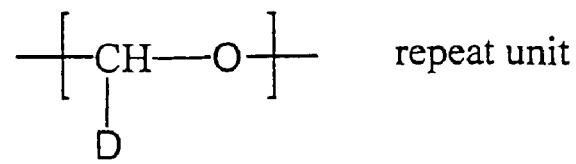 repeat unit

FIG. 4I (cont.)
Condensation polymers
Polyamide
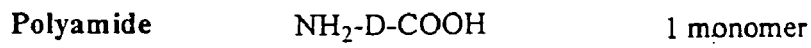
1 monomer
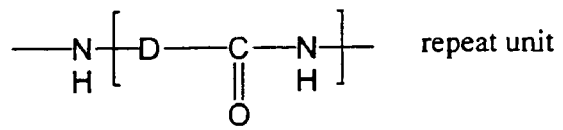
repeat unit
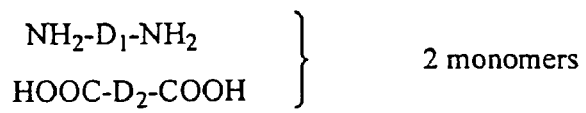
2 monomers
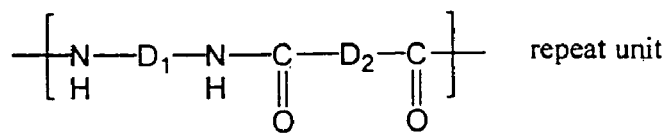
repeat unit
Polyurethane
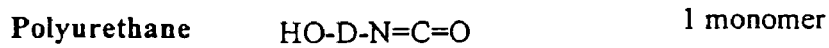
1 monomer
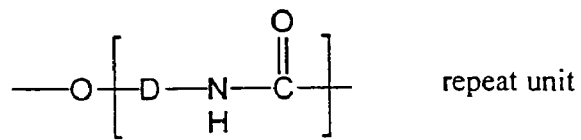
repeat unit
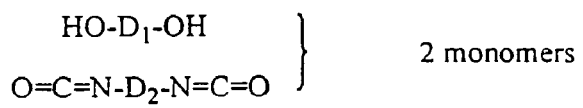
2 monomers
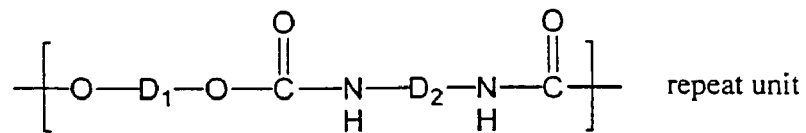
repeat unit
Polyester
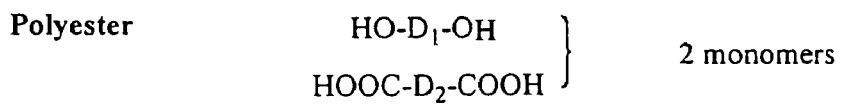
2 monomers
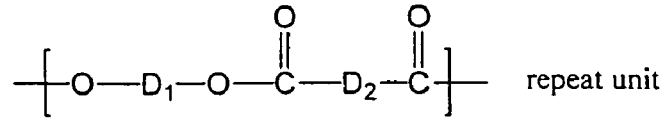
repeat unit
1 monomer
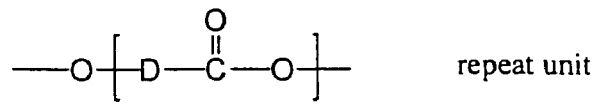
repeat unit

FIG. 4I (cont.)
Condensation polymers (cont.)
Polyacetaldehyde  HO-D$_1$-OH  } 2 monomers
D$_2$-CHO
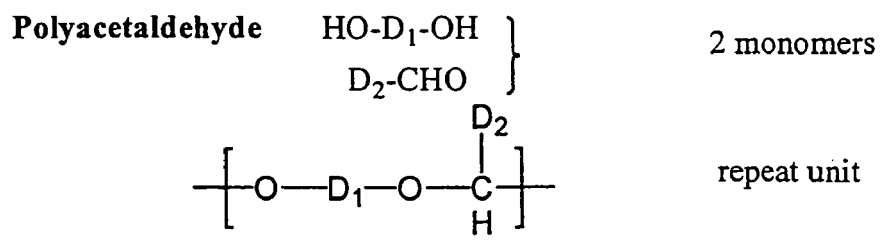 repeat unit
Polycarbonate
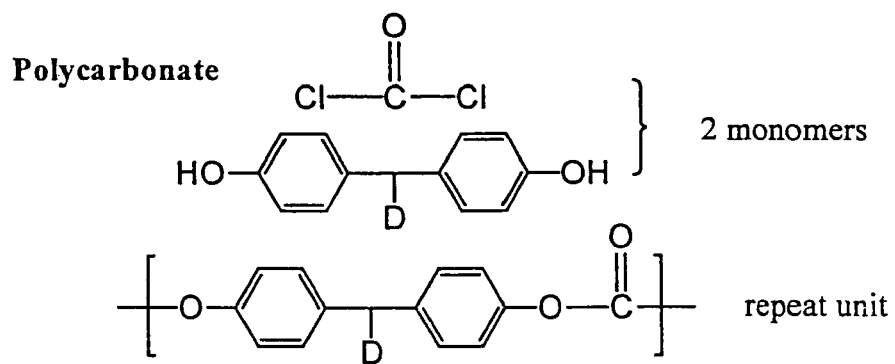
2 monomers
repeat unit
Epoxy resins (based on epichlorohydrin - bisphenol A resins)
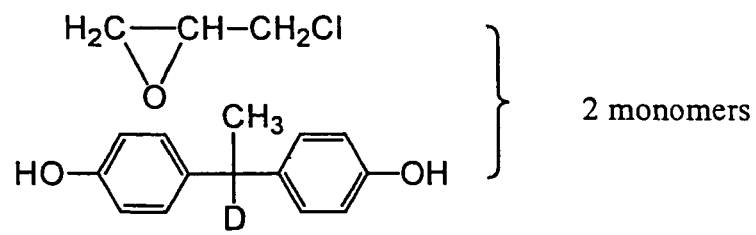 2 monomers
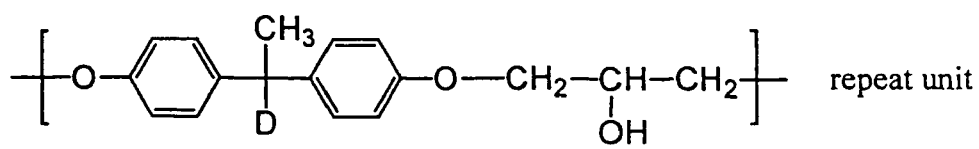 repeat unit Diamondoid-containing graft polymer Decreasing Rigidity of Cross-linked Materials

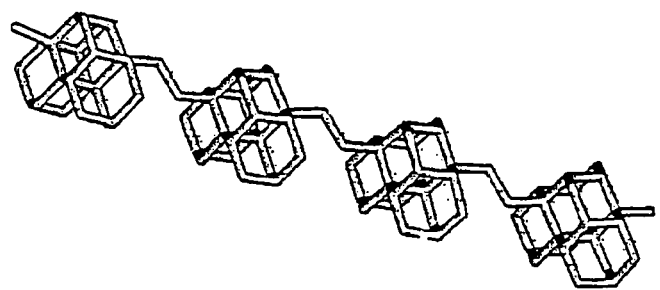
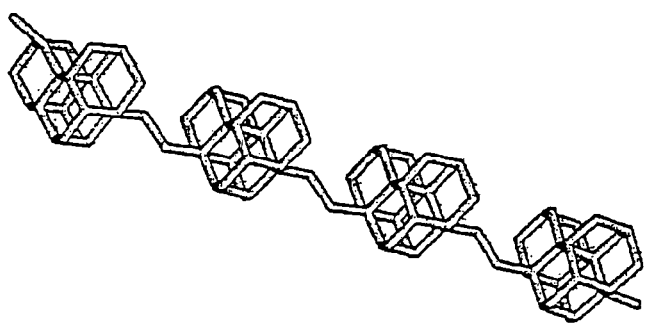
FIG. 5G
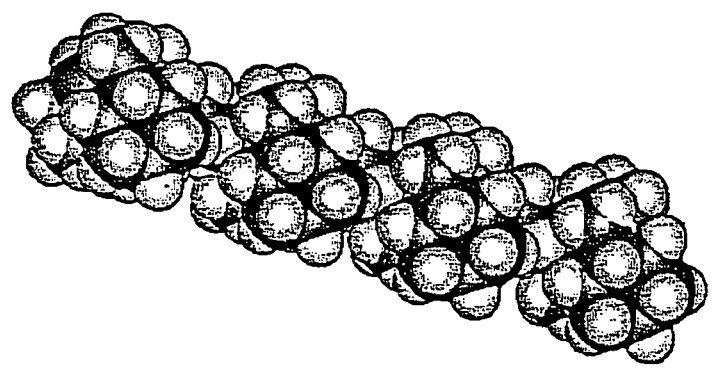
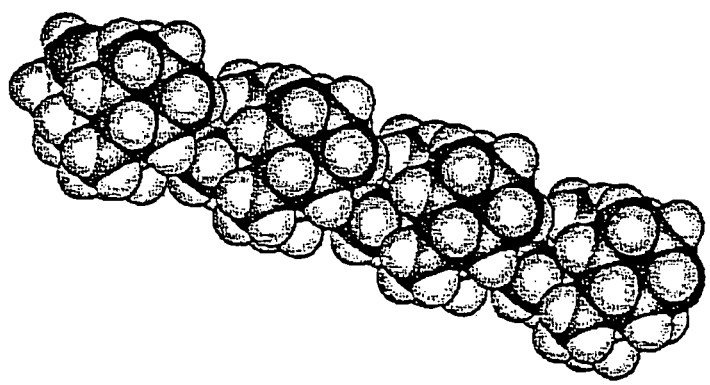
FIG. 5H

FIG. 8A

| Higher Diamondoid | Compound Reference Number | M+ (m/z) (Equals Base Peak) | GC/MS Retention Times* (min.) | GC/MS Relative Retention Times** (min.) |
|---|---|---|---|---|
| Tetramantane #1 | 4-1 | 292 | 8.10 | 1.00 |
| Tetramantane #2 | 4-2 | 292 | 8.66 | 1.07 |
| Tetramantane #3 | 4-3 | 292 | 9.12 | 1.13 |
| Pentamantane #1 | 5-1 | 344 | 10.40 | 1.28 |
| Pentamantane #2 | 5-2 | 344 | 11.93 | 1.47 |
| Pentamantane #3 | 5-3 | 344 | 11.98 | 1.48 |
| Pentamantane #4 | 5-4 | 344 | 12.38 | 1.53 |
| Pentamantane #5 | 5-5 | 344 | 12.50 | 1.54 |
| Pentamantane #6 | 5-6 | 344 | 12.71 | 1.57 |
| Cyclohexamantane | C-6 | 342 | 12.34 | 1.52 |
| Hexamantane #1 | 6-1 | 396 | 14.46 | 1.78 |
| Hexamantane #2 | 6-2 | 396 | 14.61 | 1.80 |
| Hexamantane #3 | 6-3 | 396 | 14.97 | 1.85 |
| Hexamantane #4 | 6-4 | 396 | 14.99 | 1.85 |
| Hexamantane #5 | 6-5 | 396 | 15.04 | 1.86 |
| Hexamantane #6 | 6-6 | 396 | 15.13 | 1.87 |
| Hexamantane #7 | 6-7 | 396 | 15.22 | 1.88 |
| Hexamantane #8 | 6-8 | 396 | 15.32 | 1.89 |
| Hexamantane #9 | 6-9 | 396 | 15.42 | 1.90 |
| Hexamantane #10 | 6-10 | 396 | 15.45 | 1.91 |
| Hexamantane #11 | 6-11 | 396 | 15.49 | 1.91 |
| Hexamantane #12 | 6-12 | 396 | 15.54 | 1.92 |
| Hexamantane #13 | 6-13 | 396 | 15.60 | 1.93 |
| Hexamantane #14 | 6-14 | 396 | 15.81 | 1.95 |
| Hexamantane #15 | 6-15 | 396 | 15.89 | 1.96 |
| Hexamantane #16 | 6-16 | 396 | 16.05 | 1.98 |
| Hexamantane #17 | 6-17 | 396 | 16.08 | 1.99 |
| Heptamantane #1 | 7-1 | 394 | 14.96 | 1.85 |
| Heptamantane #2 | 7-2 | 394 | 15.53 | 1.92 |
| Heptamantane #3 | 7-3 | 448 | 17.34 | 2.14 |
| Heptamantane #4A | 7-4A | 448 | 17.70 | 2.18 |
| Heptamantane #4B | 7-4B | 448 | 17.70 | 2.18 |
| Heptamantane #5 | 7-5 | 448 | 17.71 | 2.19 |
| Heptamantane #6 | 7-6 | 448 | 17.79 | 2.20 |
| Heptamantane #7 | 7-7 | 448 | 17.82 | 2.20 |
| Heptamantane #8 | 7-8 | 448 | 17.99 | 2.22 |
| Heptamantane #9A | 7-9A | 448 | 18.13 | 2.24 |
| Heptamantane #9B | 7-9B | 448 | 18.13 | 2.24 |
| Heptamantane #9C | 7-9C | 448 | 18.13 | 2.24 |
| Heptamantane #10 | 7-10 | 448 | 18.15 | 2.24 |
| Heptamantane #11 | 7-11 | 448 | 18.20 | 2.25 |
| Heptamantane #12 | 7-12 | 448 | 18.21 | 2.25 |
| Heptamantane #13A | 7-13A | 448 | 18.29 | 2.26 |
| Heptamantane #13B | 7-13B | 448 | 18.29 | 2.26 |
| Heptamantane #13C | 7-13C | 448 | 18.29 | 2.26 |
| Heptamantane #14 | 7-14 | 448 | 18.32 | 2.26 |

FIG. 8A cont'd

| Higher Diamondoid | Compound Reference Number | M+ (m/z) (Equals Base Peak) | GC/MS Retention Times* (min.) | GC/MS Relative Retention Times** (min.) |
|---|---|---|---|---|
| Octamantane #1 | 8-1 | 446 | 17.30 | 2.14 |
| Octamantane #2 | 8-2 | 446 | 17.37 | 2.14 |
| Octamantane #3 | 8-3 | 446 | 17.42 | 2.15 |
| Octamantane #4 | 8-4 | 446 | 17.47 | 2.16 |
| Octamantane #5 | 8-5 | 446 | 17.71 | 2.19 |
| Octamantane #6 | 8-6 | 446 | 17.82 | 2.20 |
| Octamantane #7 | 8-7 | 446 | 17.86 | 2.20 |
| Octamantane #8 | 8-8 | 446 | 18.22 | 2.25 |
| Octamantane #9 | 8-9 | 446 | 18.46 | 2.28 |
| Octamantane #10 | 8-10 | 446 | 18.65 | 2.30 |
| Octamantane #11 | 8-11 | 446 | 18.76 | 2.32 |
| Nonamantane #1 | 9-1 | 498 | 19.86 | 2.45 |
| Decamantane #1 | 10-1 | 456 | 18.57 | 2.29 |
| Decamantane #2 | 10-2 | 496 | 21.33 | 2.63 |
| Undecamantane#1 | 11-1 | 508 | 21.05 | 2.60 |

* HP-MS5 (30m X 0.25 mm, 0.25 micron film), helium carrier gas,
** Reference to Tetramantane #1

FIG. 8B

| Higher Diamondoid | Compound Reference Number | Fraction Number | Elution Time (min.) | Elution Volume (mL) | Elution Volume Relative to 4-1 |
|---|---|---|---|---|---|
| Tetramantane #1 | 4-1 | 4 | 119 | 594 | 1.00 |
| Tetramantane #2 | 4-2 | 7 | 125 | 627 | 1.05 |
| Tetramantane #3 | 4-3 | 6 | 123 | 616 | 1.04 |
| Pentamantane #1 | 5-1 | 11 | 134 | 669 | 1.13 |
| Pentamantane #2 | 5-2 | 19 | 151 | 754 | 1.27 |
| Pentamantane #3 | 5-3 | 28 | 170 | 850 | 1.43 |
| Pentamantane #4 | 5-4 | 22 | 157 | 786 | 1.32 |
| Pentamantane #5 | 5-5 | 19 | 151 | 754 | 1.27 |
| Pentamantane #6 | 5-6 | 20 | 153 | 765 | 1.29 |
| Cyclohexamantane | C-6 | 23 | 159 | 797 | 1.34 |
| Hexamantane #1 | 6-1 | 33 | 181 | 903 | 1.52 |
| Hexamantane #2 | 6-2 | 29 | 172 | 861 | 1.45 |
| Hexamantane #3 | 6-3 | 43 | 202 | 1012 | 1.70 |
| Hexamantane #4 | 6-4 | 33 | 181 | 903 | 1.52 |
| Hexamantane #5 | 6-5 | 35 | 185 | 924 | 1.56 |
| Hexamantane #6 | 6-6 | 63 | 242 | 1211 | 2.04 |
| Hexamantane #7 | 6-7 | 37 | 189 | 945 | 1.59 |
| Hexamantane #8 | 6-8 | 39 | 193 | 967 | 1.63 |
| Hexamantane #9 | 6-9 | 39 | 193 | 967 | 1.63 |
| Hexamantane #10 | 6-10 | 48 | 214 | 1071 | 1.80 |
| Hexamantane #11 | 6-11 | 36 | 187 | 935 | 1.57 |
| Hexamantane #12 | 6-12 | 44 | 205 | 1024 | 1.72 |
| Hexamantane #13 | 6-13 | 36 | 187 | 935 | 1.57 |
| Hexamantane #14 | 6-14 | 39 | 193 | 967 | 1.63 |
| Hexamantane #15 | 6-15 | 45 | 207 | 1036 | 1.74 |
| Hexamantane #16 | 6-16 | 44 | 205 | 1024 | 1.72 |
| Hexamantane #17 | 6-17 | 49 | 217 | 1083 | 1.82 |
| Heptamantane #1 | 7-1 | 45 | 207 | 1036 | 1.74 |
| Heptamantane #2 | 7-2 | 41 | 198 | 989 | 1.66 |
| Heptamantane #3 | 7-3 | 61 | 238 | 1190 | 2.00 |
| Heptamantane #4A | 7-4A | 90 | 304 | 1519 | 2.56 |
| Heptamantane #4B | 7-4B | 90 | 304 | 1519 | 2.56 |
| Heptamantane #5 | 7-5 | 76 | 270 | 1349 | 2.27 |
| Heptamantane #6 | 7-6 | 67 | 251 | 1253 | 2.11 |
| Heptamantane #7 | 7-7 | — | — | — | — |
| Heptamantane #8 | 7-8 | 59 | 234 | 1172 | 1.97 |
| Heptamantane #9A | 7-9A | 60 | 236 | 1181 | 1.99 |
| Heptamantane #9B | 7-9B | 62 | 240 | 1200 | 2.02 |
| Heptamantane #9C | 7-9C | 78 | 274 | 1370 | 2.31 |
| Heptamantane #10 | 7-10 | 86 | 291 | 1455 | 2.45 |
| Heptamantane #11 | 7-11 | — | — | — | — |
| Heptamantane #12 | 7-12 | — | — | — | — |
| Heptamantane #13A | 7-13A | 58 | 233 | 1163 | 1.96 |
| Heptamantane #13B | 7-13B | 74 | 266 | 1328 | 2.24 |
| Heptamantane #13C | 7-13C | 90 | 304 | 1519 | 2.56 |
| Heptamantane #14 | 7-14 | 70 | 257 | 1285 | 2.16 |

FIG. 8B cont'd

| Higher Diamondoid | Compound Reference Number | Fraction Number | Elution Time (min.) | Elution Volume (mL) | Elution Volume Relative to 4-1 |
|---|---|---|---|---|---|
| Octamantane #1 | 8-1 | 81 | 280 | 1402 | 2.36 |
| Octamantane #2 | 8-2 | 83 | 285 | 1423 | 2.40 |
| Octamantane #3 | 8-3 | 64 | 244 | 1221 | 2.06 |
| Octamantane #4 | 8-4 | — | — | — | — |
| Octamantane #5 | 8-5 | 63 | 242 | 1211 | 2.04 |
| Octamantane #6 | 8-6 | 79 | 276 | 1381 | 2.32 |
| Octamantane #7 | 8-7 | 71 | 259 | 1296 | 2.18 |
| Octamantane #8 | 8-8 | 84 | 287 | 1434 | 2.41 |
| Octamantane #9 | 8-9 | 74 | 266 | 1328 | 2.24 |
| Octamantane #10 | 8-10 | 80 | 280 | 1402 | 2.36 |
| Octamantane #11 | 8-11 | 85 | 289 | 1445 | 2.43 |
| Nonamantane #1 | 9-1 | 89 | 297 | 1487 | 2.50 |
| Decamantane #1 | 10-1 | 83 | 285 | 1423 | 2.40 |
| Decamantane #2 | 10-2 | — | — | — | — |
| Undecamantane#1 | 11-1 | 101 | 355 | 1774 | 2.99 |

ODS HPLC Whatman ODS-II 10/50
(2 Columns in series), acetone mobile phase @5.0 mL/min.

FIG. 10

| | 601-656 Fr.1 | 656-702 Fr.2 | 702-752 Fr.3 | 752-800 Fr.4 | 800-852 Fr.5 | 852-900 Fr.6 | 900-950 Fr.7 | 950-976 Fr.8 | 976-1000 Fr.9 | 1000-1026 Fr.10 |
|---|---|---|---|---|---|---|---|---|---|---|
| Higher Diamondoid | | | | | | | | | | |
| Tetramantanes | ▓ | | | | | | | | | |
| Pentamantanes | | ▓ | ▓ | | | | | | | |
| Cyclohexamantanes | | | ▓ | ▓ | | | | | | |
| Hexamantanes | | | | ▓ | ▓ | | | | | |
| Heptamantanes | | | | ▓ | ▓ | ▓ | | | | |
| Octamantanes | | | | | ▓ | ▓ | ▓ | ▓ | | |
| Nonamantanes | | | | | | ▓ | ▓ | ▓ | | |
| Decamantanes | | | | | | ▓ | ▓ | ▓ | ▓ | ▓ |
| Undecamantanes | | | | | | ▓ | ▓ | ▓ | ▓ | ▓ |

Distillation Cuts Made on Atmospheric Resid of Feedstock B (°C)

Starting Material

Fraction #6

Parr Reaction No. 4,

Fraction #6

| Hypercarb HPLC Fraction # | 1 | 2 | 3 | 4 | 5 | 6 | 7 | 8 | 9 | 10 | 11 | 12 | 13 | 14 | 15 | 16 | 17 | Fully Condensed Hexamantane | |
|---|---|---|---|---|---|---|---|---|---|---|---|---|---|---|---|---|---|---|---|
| 1 | | | | | | | | | | | | | | | | | | | |
| 2 | | | | | | | | | | | | | | | | | | | |
| 3 | | | | | | | | | | | | | | | | | | | |
| 4 | | | | | | | | | | | | | | | | | | ■ | |
| 5 | | | | | | | | | | | | | | | | | | | |
| 26 | | | | | | | | | | | | | | | | | | | |
| 27 | | | | | | | | | | | | | ■ | | | | | | Hex 13 |
| 28 | | | | | | | | | | | | | ■ | | | | | | |
| 29 | | | | | | | | | | | | | | ■ | | | | | Hex 14 |
| 30 | ■ | | | | | | | | | | | | | ■ | | | | | Hex 1 |
| 31 | | | | | | | | | | | | | | ■ | | | | | Hex 10 |
| 32 | | | | | | | | | | | ■ | | | ■ | | | | | Hex 11 |
| 33 | | | | | | | | | | | ■ | | | | | | | | |
| 34 | | | | | | | | | | | ■ | | | | | | | | |
| 35 | | | | | | | | | | | ■ | | | | | | | | |
| 43 | | | | | | | | | | | | | | | | | | | |
| 44 | | | | | | | ■ | | | | | | | | | | | | Hex 6 |
| 45 | | | | | | | | | | | | | | | | | | | |
| 46 | | | | | | | | | | | | | | | | | | | |
| 47 | | | | | | | | | | | | | | | | | | | |
| 48 | | | | | | | | | | | | | | | | | | | |
| 49 | | | | | | | | | | ■ | | | | | | ■ | | | Hex 15 |
| 50 | | | | | | | | | | ■ | | | | | | ■ | | | Hex 9 |
| 51 | | | | | | | | | | ■ | | | | | | | | | |
| 52 | | ■ | | | | | | | | ■ | | | | | | | | | |
| 53 | | ■ | | | | | | | | | | | | | | | | | |
| 54 | | ■ | | | | | | | | | | | | | | | | | Hex 2 |
| 55 | | ■ | | | | | | | | | | | | | | | | | |
| 56 | | ■ | | | | | | | | | | | | | | | | | |
| 57 | | ■ | | | | | | | | | | | | | | | | | |
| 58 | | ■ | | | | | | | | | | | | | | | | | |
| 59 | | ■ | | | | | | | | | | | | | | | | | |
| 60 | | ■ | | | | | | | | | | | | | | | | | |
| 61 | | ■ | | | | | | | | | | | | | | | | | |
| 62 | | | | | | | | | | | | | | | | | | | |
| 72 | | | | | | | ■ | | | | | | | | | | | | |
| 73 | | | | | | | ■ | | | | | | | | | | | | |
| 74 | | | | | | | ■ | | | | | | | | | | | | |
| 75 | | | | | | | ■ | | | | | | | | | | | | Hex 7 |
| 76 | | | | | | | ■ | | | | | | | | | | | | |
| 77 | | | | | | | ■ | | | | | | | | | | | | |
| 78 | | | | | | | | | | | | | | | | | | | |
| 84 | | | | | | | | | | | | | | | | | | | |

FIG. 15A
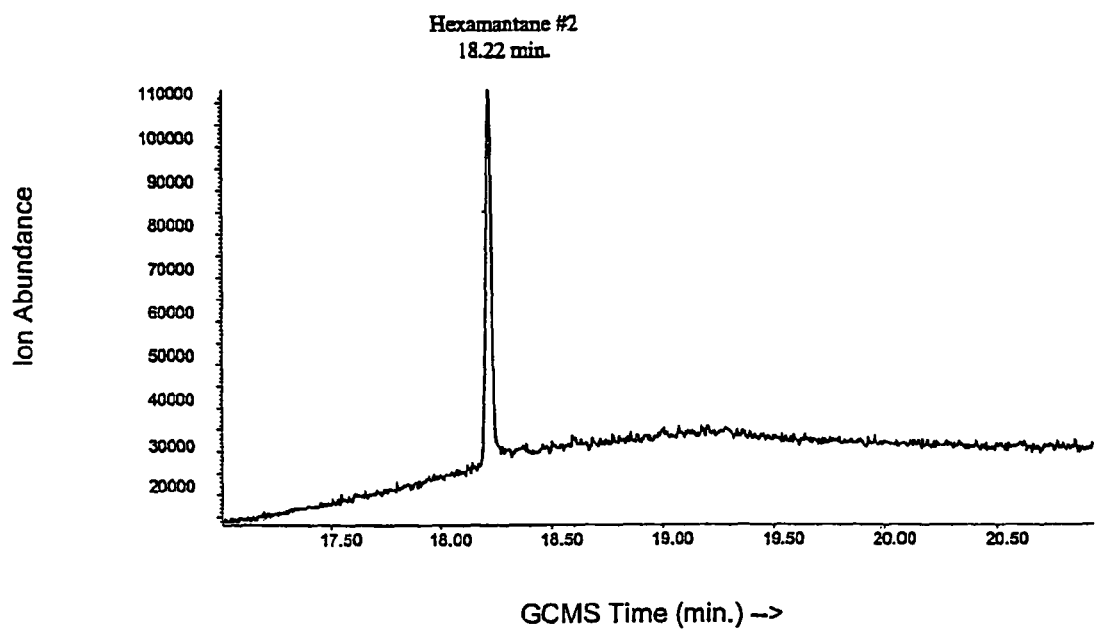
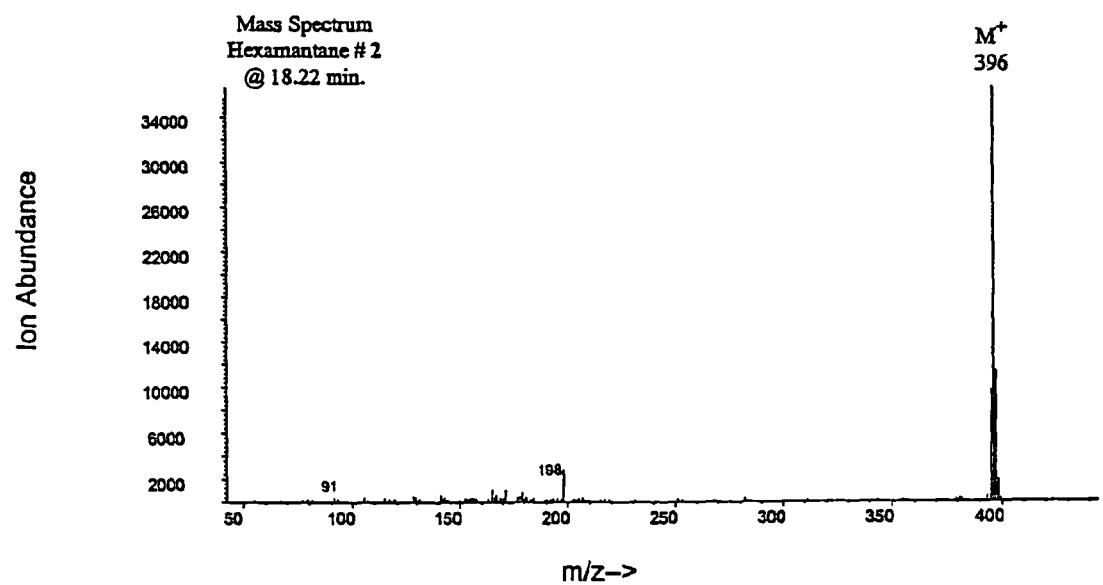
FIG. 15B

*Alkyltetramantane
+Alkane impurity

TIC of Bromination Products of a Feedstock Containing a Mixture of Tetramantanes and Alkyltetramantanes TIC of Mono-brominated Products TIC of Di- and Tri-brominated Products GC of a Mono-brominated Tetramantane (•, 12.038 min.)

GCMS of the Mono-brominated Tetramantane @ 12.038 min.

GC of Mono-brominated Methyltetramantanes (∗, 11.644 and 11.992 min.)

GCMS of the Monobrominated Methyltetramantanes @ 11.644 (inset) and 11.992 min.

GC of a Mono-brominated Dimethyltetramantane (∗, 12.192 min.)

GCMS of the Monobrominated Dimethyltetramantane @ 12.192 min.

GC of a Di-brominated Tetramantane (∗, 15.753 min.)

GCMS of the Di-brominated Tetramantane @ 15.753 min.

GC of a Di-brominated Methyltetramantane (*, 15.879 min.)

GCMS of the Di-brominated Methyltetramantane @ 15.879 min.

GC of a Tri-brominated Tetramantane (∗, 17.279 min.)

GCMS of the Tri-brominated Tetramantane @ 17.279 min.

GC of a Tri-brominated Methyltetramantane (*, 15.250 min.)

GCMS of the Tri-brominated Methyltetramantane @ 15.250 min.

FIG. 37A
Aromatic bisphenols: HO-Ar-OH
Ar:
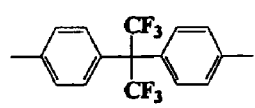 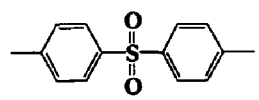 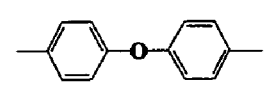
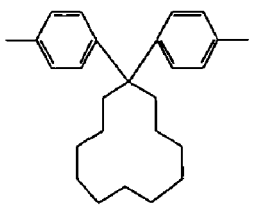 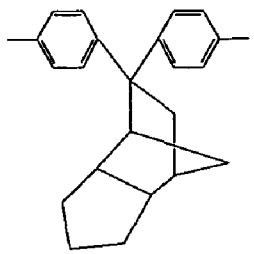 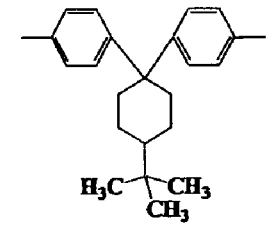
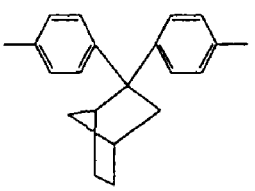 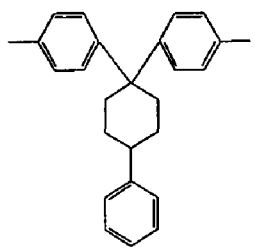 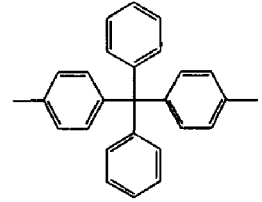
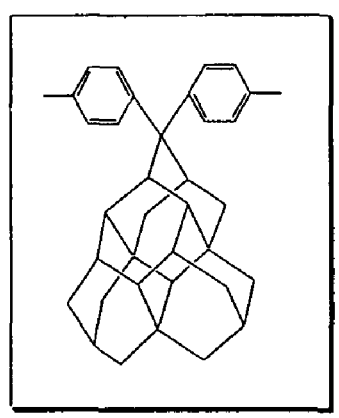 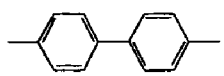 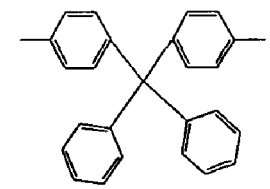

FIG. 39B
Aromatic Dianhydride
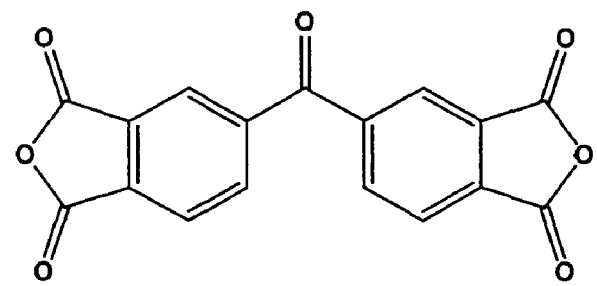
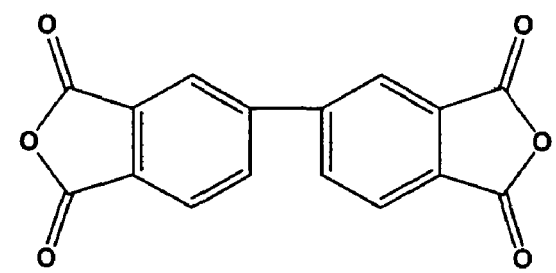
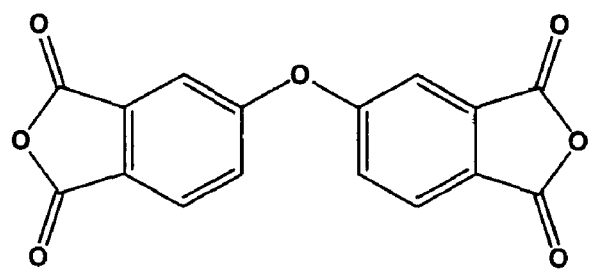
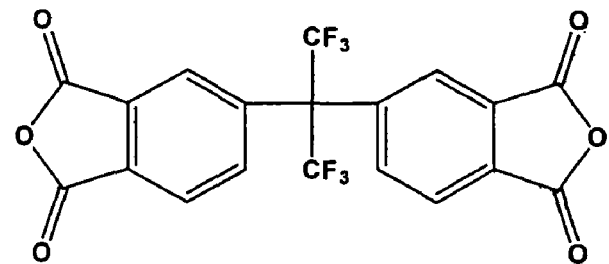

FIG. 42
Aromatic diamines: H₂N-Ar-NH₂
Ar:
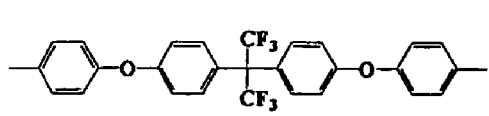
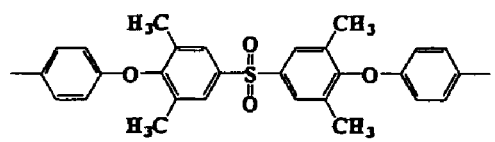
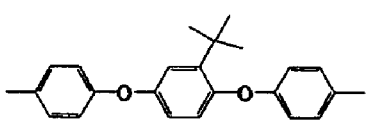
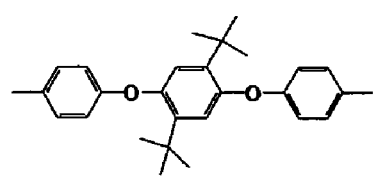
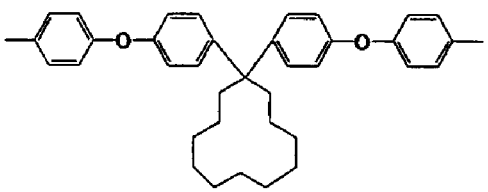
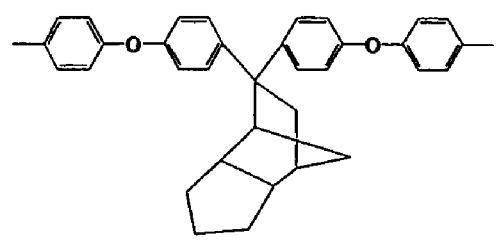
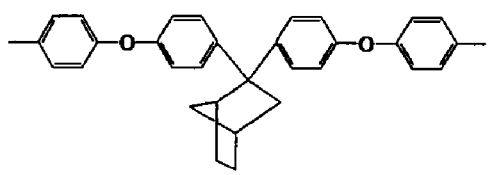
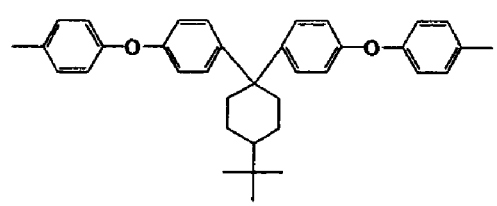
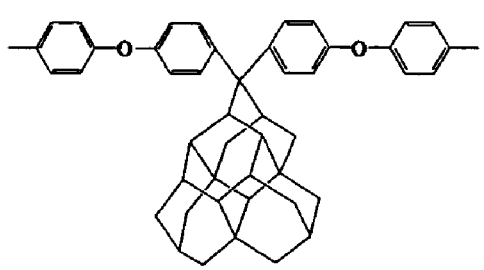
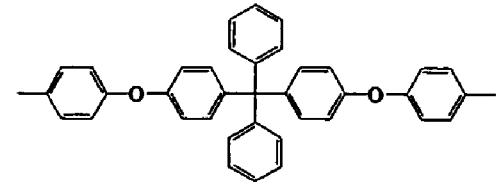

POLYMERIZABLE HIGHER DIAMONDOID DERIVATIVES

REFERENCE TO RELATED APPLICATIONS

This application is a divisional of U.S. Ser. No. 10/046,486 filed Jan. 16, 2002, now U.S. Pat. No. 6,858,700, which claimed priority under 35 U.S.C. §119(e) to U.S. Provisional Application No. 60/262,842, filed Jan. 19, 2001 and to U.S. Provisional Application No. 60/348,032, filed Oct. 26, 2001, all of which are incorporated by reference.

BACKGROUND OF THE INVENTION

Field of the Invention

This invention is directed to higher diamondoid derivatives containing moieties that are capable of undergoing polymerization. This invention is further directed to processes for polymerizing such derivatives, to chemical intermediates useful for the synthesis of such derivatives and to polymers based upon these derivatives.

References

The following publications and patents are cited in this application as superscript numbers:

[1] Fort, Jr., et al., Adamantane: *Consequences of the Diamondoid Structure*, Chem. Rev., 64:277-300 (1964).
[2] Capaldi, et al., Alkenyl Adamantanes, U.S. Pat. No. 3,457,318, issued Jul. 22, 1969.
[3] Thompson, Polyamide Polymer of Diamino Methyl Adamantane and Dicarboxylic Acid, U.S. Pat. No. 3,832,332, issued Aug. 27, 1974.
[4] Baum, et al., Ethynyl Adamantane Derivatives and Methods of Polymerization Thereof, U.S. Pat. No. 5,017,734, issued May 21, 1991.
[5] Ishii, et al., Polymerizable Adamantane Derivatives and Process for Producing Same, U.S. Pat. No. 6,235,851, issued May 22, 2001.
[6] McKervey, et al., *Synthetic Approaches to Large Diamondoid Hydrocarbons*, Tetrahedron, 36:971-992 (1980).
[7] Lin, et al., Natural Occurrence of Tetramantane ($C_{22}H_{28}$), Pentamantane ($C_{26}H_{32}$) and Hexamantane ($C_{30}H_{36}$) in a Deep Petroleum Reservoir, Fuel, 74(10):1512-1521 (1995).
[8] Chen, et al., Isolation of High Purity Diamondoid Fractions and Components, U.S. Pat. No. 5,414,189, issued May 9, 1995.
[9] Balaban et al., *Systematic Classification and Nomenclature of Diamond Hydrocarbons-I, Tetrahedron.* 34, 3599-3606 (1978).

All of the above publications and patents are herein incorporated by reference in their entirety to the same extent as if each individual publication or patent was specifically and individually indicated to be incorporated by reference in its entirety.

State of the Art

Diamondoids are cage-shaped hydrocarbon molecules possessing rigid structures resembling tiny fragments of a diamond crystal lattice as described by Fort, Jr., et al.[1] Adamantane is the smallest member of the diamondoid series and consists of a single cage structure of the diamond crystal lattice. Diamantane contains two adamantane subunits face-fused to each other, triamantane three, tetramantane four, and so on. While there is only one isomeric form of adamantane, diamantane and triamantane, there are four different isomeric tetramantanes (i.e., four different shapes containing four adamantane subunits). Two of the isomeric tetramantanes are enantiomeric. The number of possible isomers increases rapidly with each higher member of the diamondoid series.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$), excellent thermal conductivity, and superb optical properties.

Adamantane, which is commercially available, has been studied extensively. The studies have been directed to a number of areas, such as thermodynamic stability, functionalization and properties of adamantane-containing materials. For instance, the following patents describe adamantane derivatives and adamantane-based polymers. U.S. Pat. No. 3,457,318 teaches the preparation of polymers from alkenyl adamantanes;[2] U.S. Pat. No. 3,832,332 describes a polyamide polymer formed from alkyladamantane diamine;[3] U.S. Pat. No. 5,017,734 discusses the formation of thermally stable resins from ethynyl adamantane derivatives;[4] and, U.S. Pat. No. 6,235,851 reports the synthesis and polymerization of a variety of adamantane derivatives.[5]

The higher diamondoids, which include the tetramantanes, pentamantanes, etc., have received comparatively little attention. In fact, prior to the work of inventors Dahl and Carlson embodied in U.S. Patent Application Ser. No. 60/262,842 filed Jan. 19, 2001 and numerous subsequent filings, these compounds were nearly hypothetical with only one such compound having been synthesized and a few others tentatively identified (but not isolated). More specifically, McKervey, et al. reported the synthesis of anti-tetramantane in low yields using a laborious, multistep process.[6] Lin, et al. have suggested the existence of tetramantane, pentamantane and hexamantane in deep petroleum reservoirs from mass spectroscopy alone and without any attempt to isolate materials.[7] The possible presence of tetramantane and pentamantane in pot material recovered after a distillation of a diamondoid-containing feedstock has been discussed by Chen, et al.[8]

SUMMARY OF THE INVENTION

This invention is directed to higher diamondoids that have been derivatized to contain moieties which are capable of undergoing polymerization reactions or being bonded to polymers, to processes for polymerizing these derivatized higher diamondoids, to intermediates useful in forming these derivatives; and to polymers formed from these derivatized higher diamondoids.

Thus, in one aspect this invention is related to polymerizable higher diamondoid derivatives which are higher diamondoids which have one or more polymerizable substituent groups substituting for original hydrogens. Polymerizable higher diamondoid derivatives may be represented by Formula I below:

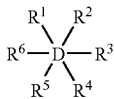

wherein D is a higher diamondoid nucleus; and $R^1$, $R^2$, $R^3$, $R^4$, $R^5$ and $R^6$ are independently selected from a group consisting of hydrogen and one or more polymerizable moieties; provided there is at least one polymerizable moiety on the compound. Preferably, the compound contains either one or two polymerizable moieties.

This invention also relates to intermediates useful in the synthesis of such higher diamondoid derivatives. These higher diamondoid intermediates may be represented by Formula II below:

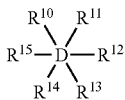

wherein D is as set forth in Formula I and at least one of $R^{10}$—$R^{15}$ is a covalently attached moiety which can be converted to a polymerizable moiety or which, in some cases, may be a polymerizable moiety as well. The remaining R's are hydrogens.

In the intermediates represented by Formula II, $R^{10}$, $R^{11}$, $R^{12}$, $R^{13}$, $R^{14}$ and $R^{15}$ are preferably independently selected from a group of moieties consisting of —H, —F, —Cl, —Br, —I, —OH, —SH, —NH$_2$, —NHCOCH$_3$, —NHCHO, —CO$_2$H, —CO$_2$R', —COCl, —CHO, —CH$_2$OH, =O, —NO$_2$, —CH=CH$_2$, —C≡CH and —C$_6$H$_5$; where R' is alkyl (preferably ethyl) provided that $R^{10}$, $R^{11}$, $R^{12}$, $R^{13}$, $R^{14}$ and $R^{15}$ are not all hydrogen. Typically one or two of $R^{10}$—$R^{15}$ are nonhydrogen moieties and the remaining R's are hydrogens. These intermediates can be present in reaction media and the like in concentrations of at least about 10 ppm and especially at least about 100 ppm. Mixtures of these intermediates may be used as well.

In another aspect, this invention is directed to methods of obtaining polymers which comprise higher diamondoids. These methods comprise: a) selecting one or more higher diamondoid derivatives of Formula I, alone or in combination with other polymerizable materials; b) subjecting the materials selected in a) to polymerization or coupling conditions thereby forming a higher diamondoid-containing polymer; and c) recovering the higher diamondoid-containing polymer.

In yet another aspect, this invention is directed to polymers which contain higher diamondoids as recurring units.

BRIEF DESCRIPTION OF THE DRAWINGS

FIG. 1B illustrates a variety of representative derivatized higher diamondoids carrying one or two polymerizable moieties.

FIG. 2B shows a carbon numbering sequence we used for the four isomeric tetramantanes.

FIGS. 5G and 5H illustrate with both carbon framework and CPK structures exemplary chiral polymers prepared from enantiomeric higher diamondoid derivatives, in this case one of the enantiomeric tetramantanes.

FIGS. 8A and 8B are compilations of the GC/MS and HPLC properties of various higher diamondoids included in this application.

FIG. 10 is a chart illustrating distillation of cuts of a higher diamondoid-containing feedstock (Fedstock B, atmospheric distillation residue) showing cut selections to favor the enrichment of specific groups of higher diamondoids.

FIGS. 12A and 12B are charts illustrating elution sequences for a variety of individual higher diamondoids (hexamantanes) on two different HPLC chromatography columns: ODS and Hypercarb.

FIG. 14A shows the first column cuts, containing two of the hexamantanes from Feedstock B that were sent to the secund column. FIG. 14B shows the second column peaks isolated and sent to the traps. Using this procedure pure hexamantanes were isolated. Hexamantane #2 was the second hexamantane to elute in our GC/MS assay, while hexamantane #8 was the eighth to elute.

FIGS. 15A and 15B illustrate the GC/MS total ion chromatogram and mass spectrum of hexamantane #2 in FIG. 13.

FIG. 17 is a total ion chromatogram of a tetramantane and alkyltetramantane-containing starting material.

FIG. 18 illustrates the GC/MS total ion chromatogram showing mono, di and tri brominated tetramantanes.

FIG. 19 shows the presence of monobrominated tetramantanes in the total ion chromatogram of the reaction product showing that these compounds are the major components within this GC/MS retention time range.

FIG. 20 shows the presence of polybrominated tetramantanes in a brominated tetramantane product as the major components within this GC/MS retention time range.

FIG. 21 shows the presence on a monobrominated tetramantane eluting at 12.038 in the total ion chromatogram of the reaction product.

FIG. 22 is the mass spectrum of a monobrominated tetramantane with GC/MS retention time of 12.038 minutes. The based peak in this spectrum is the 371 m/z molecular ion.

FIG. 23 shows the presence of monobrominated methyltetramantanes in the total ion chromatogram of the reaction product.

FIG. 24 is the mass spectra of monobrominated methyltetramantanes with GC/MS retention times of 11.644 and 11.992 minutes. The base peaks in these spectra are both the 385 m/z molecular ion.

FIG. 25 shows the presence of brominated dimethyl tetramantanes in the total ion chromatogram of the reaction product.

FIG. 26 is the mass spectrum of the monobrominated dimethyltatramantane with GC/MS retention time of at 12.192 minutes.

FIG. 27 shows the presence of dibrominated tetramantanes in the total ion chromatogram of the reaction product.

FIG. 28 is the mass spectrum of a dibrominated tetramantane with GC/MS retention time of 15.753 minutes. The base peak in this spectrum is the 447 m/z molecular ion.

FIG. 29 shows the presence of dibrominated methyltetramantanes in the total ion chromatogram of the reaction product.

FIG. 30 is the mass spectrum of a dibrominated methyltetramantane with GC/MS retention time of 15.879 minutes. The base peak in this spectrum is the 461 m/z molecular ion.

FIG. 31 shows the presence of tribrominated tetramantanes in the total ion chromatogram of the reaction product.

FIG. 32 is the mass spectrum of a tribrominated tetramantane with GC/MS retention time of 17.279 minutes. The base peak in this spectrum is the 527 m/z molecular ion.

FIG. 33 shows the presence of tribrominated methyltetramantanes in the total ion chromatogram of the reaction product.

FIG. 34 is the mass spectrum of a tribrominated methyltetramantane with GC/MS retention time of 15.250 minutes. The molecular ion is 541 m/z.

FIGS. 35-42 depict a variety of additional polymers that may be prepared in accord with this invention and representative components for incorporation into such polymers.

DETAILED DESCRIPTION OF THE INVENTION

Figure 1A:
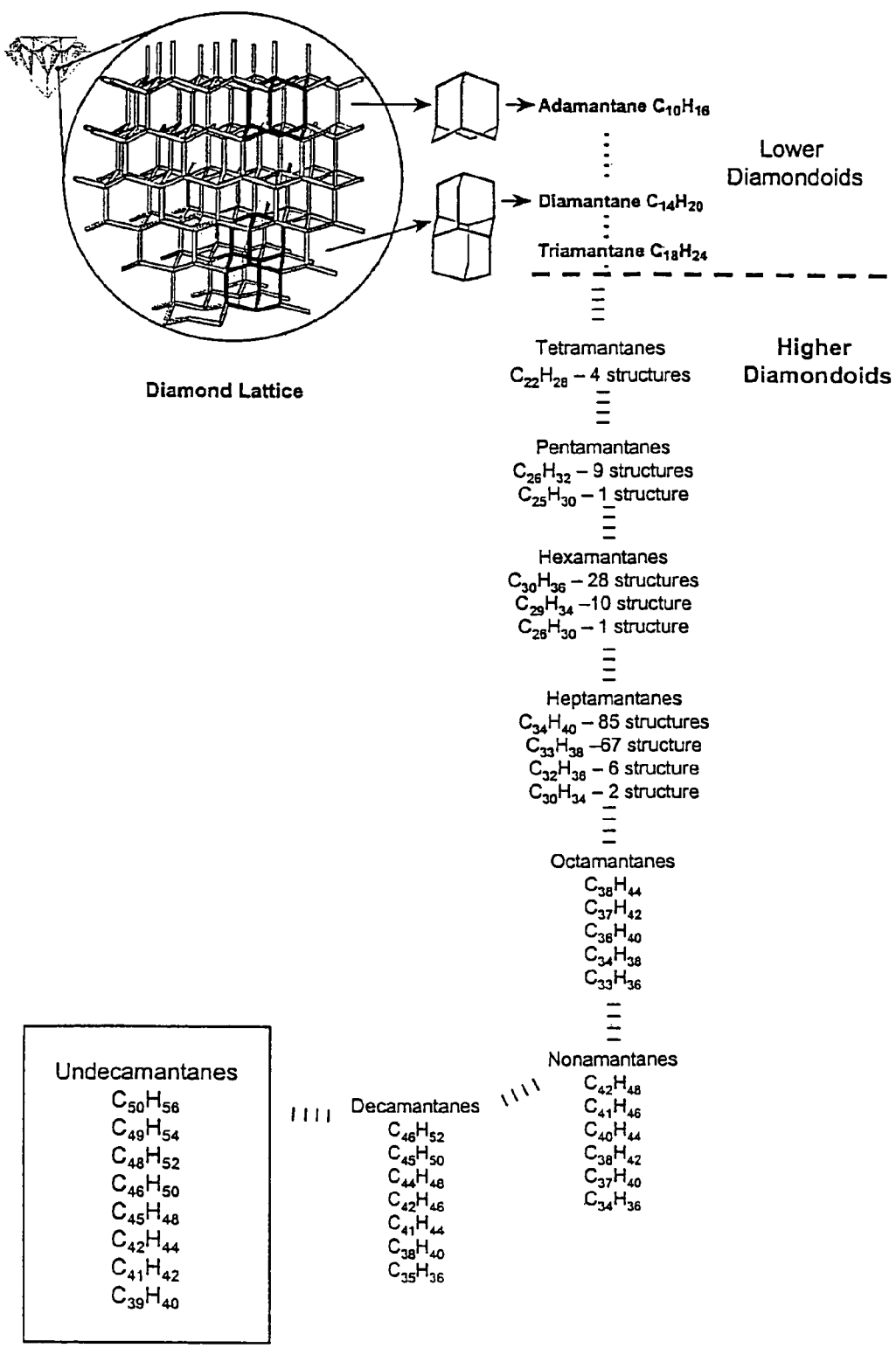
FIG. 1A illustrates the cage-shaped structure of diamondoids and their correlation to diamonds. Specifically, illustrated is the correlation of the structures of diamondoids to subunits of the diamond crystal lattice.

This Detailed Description is presented in the following subsections:
Definitions
Higher Diamondoids and Their Recovery
The Higher Diamondoid Derivatives
The Higher Diamondoid Intermediates
Methods For Preparing Higher Diamondoid Derivatives and Intermediates
Polymerization of Higher Diamondoid Derivatives
Higher Diamondoid-Containing Polymers
Utility Definitions As used herein, the following terms have the following meanings.

The term "diamondoid" refers to substituted and unsubstituted caged compounds of the adamantane series including substituted and unsubstituted adamantane, diamantane, triamantane, tetramantane, pentamantane, hexamantane, heptamantane, octamantane, nonamantane, decamantane, undecamantane, and the like and also including various molecular weight forms of these components and including isomers of these forms. Substituted diamondoids preferably comprise from 1 to 10 and more preferably 1 to 4 alkyl substituents. "Diamondoids" include "lower diamondoids" and "higher diamondoids".

The term "lower diamondoids" or "adamantane, diamantane and triamantane" refers to any and/or all unsubstituted and substituted derivatives of adamantane, diamantane or triamantane. These lower diamondoids show no isomers and are readily synthesized, distinguishing them from the "higher diamondoids".

The term "higher diamondoids" refers to any and/or all substituted and unsubstituted tetramantanes; to any and/or all substituted and unsubstituted pentamantanes; to any and/or all substituted and unsubstituted hexamantanes; to any and/or all substituted and unsubstituted heptamantanes; to any and/or all substituted and unsubstituted octamantanes; to any and/or all substituted and unsubstituted nonamantanes; to any and/or all substituted and unsubstituted decamantanes; to any and/or all substituted and unsubstituted undecamantanes; as well as mixtures of the above as well as isomers and stereoisomers. When reference is being made to one or more specific higher diamondoid isomers, they will often be referred to as "component" or "components", for example a "tetramantane component."

The term "higher diamondoid derivative" refers to a higher diamondoid which has had at least one of its hydrogens replaced by a polymerizable moiety. The portion of the higher diamondoid present in a higher diamondoid derivative is referred to as a "higher diamondoid nucleus."

The term "polymerizable moiety" refers to any chemical functional group that, when covalently attached to a higher diamondoid, can participate in a polymerization reaction to form a polymer or can participate in the covalent attachment of the diamondoid to a polymer substrate. Such groups include, without limitation, the following: unsaturated esters, amides, epoxides, alkenes, alkynes, amines, hydroxyls, and carboxyls. Preferably, the polymerizable moiety is an alkene, an unsaturated ester or an amide.

The term "higher diamondoid intermediate" refers to a higher diamondoid which has had at least one of its hydrogens replaced by an "intermediate moiety."

The term "intermediate moiety" refers to any chemical functional group that, when covalently attached to a higher diamondoid, can either serve as a polymerizable moiety or as an intermediate in the synthesis of a polymerizable moiety on the higher diamondoid.

The terms "conditions suitable for inducing a polymerization reaction", "suitable polymerization conditions" and the like refer to any chemical reaction parameters that will allow at least one polymerizable higher diamondoid derivative to form a covalent bond with another, or with a polymer substrate.

The terms "polymer" and "higher diamondoid-containing polymer" and the like refer to a molecule having multiple copies of the same or different higher diamondoid nucleus, covalently attached to each other or to a backbone chain. This includes polymers where the higher diamondoid nucleus is pendant from and not part of the polymer chain including atactic ard isotactic polymers and polymers where a higher diamondoid nucleus is part of the polymer chain. FIGS. 4 and 35-41 show a variety of representative polymer structures of this invention. "Polymers" include "homopolymers" and "copolymers" and "terpolymers." A unit or group, whether higher diamondoid or other, which reports in a polymer is said to "recur" to be a "recurring unit" of the polymer.

The term "homopolymer" refers to a polymer having only higher diamondoid recurring units. For the purposes of this specification and claims homopolymers will also include polymers having two or more different higher diamondoid recurring units.

The term "copolymer" refers to a polymer formed from one or more higher diamondoid derivative and an additional nondiamondoid monomer and thus having higher diamondoid and nondiamondoid recurring units.

The term "terpolymer" refers a polymer formed from one or more higher diamondoid derivatives and two or more nondiamondoid monomers.

The term "linker" refers to a nondiamondoid moiety having at least 2 and preferably 2-10 identical or different functional groups. At least one of the functional groups reacts with at least one polymerizable moiety or intermediate moiety on the higher diamondoid derivative. At least one additional functional group takes part in the polymerization reaction.

The term "a polymerization reaction" refers to the reaction of a higher diamondoid derivative performed under suitable polymerization conditions to form a polymer.

The term "feedstock" or "hydrocarbonaceous feedstock" refers to hydro-carbonaceous materials comprising recoverable amounts of higher diamondoids. Preferably, such feedstocks include oil, gas condensates, refinery streams, oils derived from reservoir rocks, oil shale, tar sands, and source rocks, and the like. Such components typically, but not necessarily, comprise one or more lower diamondoid components as well as nondiamondoid components. The latter is typically characterized as comprising components having a boiling point both below and above the lowest boiling point tetramantane which boils at about 350° C. at atmospheric pressure. Typical feedstocks may also contain impurities such as sediment, metals including nickel, vanadium and other inorganics. They may also contain heteromolecules containing sulfur, nitrogen and the like. All of these nondiamondoid materials are included in "nondiamondoid components" as that term is defined herein.

The term "nondiamondoid components" refers to components of the feedstock from which diamondoids are isolated that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography (GC), high performance liquid chromatography (HPLC), and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, cyclopropyl, cyclobutyl, cyclopentyl, cyclohexyl and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a divalent (branched or unbranched) saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monovalent of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. Preferred alkenyl groups include ethenyl (—CH═CH$_2$), n-propenyl(—CH$_2$CH═CH$_2$), iso-propenyl (—C(CH$_3$)═CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a divalent of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1-6 sites of vinyl unsaturation. This term is exemplified by groups such as ethenylene (—CH═CH—), the propenylene isomers (e.g., —CH$_2$CH═CH— and —C(CH$_3$)═CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monovalent unsaturated hydrocarbon preferably having from 2 to 40 carbon atoms, more preferably 2 to 20 carbon atoms and even more preferably 2 to 6 carbon atoms and having at least 1 and preferably from 1-6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a divalent unsaturated hydrocarbon preferably having from 2 to 40 carbon atoms, more preferably 2 to 10 carbon atoms and even more preferably 2 to 6 carbon atoms and having at least 1 and preferably from 1-6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the divalent derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)β-cycloalkyl", "—C(O)O-substituted cycloalkyl", "—C(O)O-alkenyl", "—(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-alkyl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heteroarylene" refers to the divalent group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "alkheteroaryl" refers to the group -alkylene-heteroaryl where alkylene and heteroaryl are as defined herein.

The term "alkheteroarylene" refers to the group -alkylene-heteroarylene where alkylene and heteroarylene are as defined herein.

The term "heterocycle" or "heterocyclic" refers to a monovalent saturated unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the divalent group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Higher Diamondoids and Their Recovery

As shown in FIG. 1A, higher diamondoids are bridged-ring cycloalkanes that have carbon-atom frameworks that can be superimposed on the diamond crystal lattice. They are the tetramers, pentamers, hexamers, heptamers, octamers, nonamers, decamers, etc. of adamantane (tricyclo[3.3.1.1$^{3,7}$]decane) or $C_{10}H_{16}$ in which various adamantane units are face-fused. The higher diamondoids can contain many alkyl substituents. These compounds have extremely rigid structures and have the highest stability of any compound with their formula. There are four tetramantane structures; iso-tetramantane [1(2)3], anti-tetramantane [121] and two enantiomers of skew-tetramantane [123] with the more general bracketed nomenclature for these diamondoids in accordance to a convention by Balaban et al.[15] There are ten pentamantanes, nine have the molecular formula $C_{26}H_{32}$ (molecular weight 344), and among these nine there are three pairs of enantiomers represented by: [12(1)3], [1234], [1213] with the non-enantiomeric pentamantanes represented by: [12(3)4], [1(2,3)4], [1212]. There also exists a more strained pentamantane, [1231], represented by the molecular formula $C_{25}H_{30}$ (molecular weight 330). Hexamantanes exist with thirty-nine different structures, twenty-eight having the molecular formula $C_{30}H_{36}$ (molecular weight 396) and of these, six are achiral; ten more strained hexamantanes have the molecular formula $C_{29}H_{34}$ (molecular weight 382) and the remaining hexamantane [12312] has the molecular formula $C_{26}H_{30}$ (molecular weight 342), also called cyclohexamantane because of its highly condensed circular structure. Heptamantanes are postulated to exist in one hundred and sixty possible structures; with eighty-five having the molecular formula $C_{34}H_{40}$ (molecular weight 448) and of these, seven are achiral, having no enantiomers. Of the heptamantanes, sixty-seven have the molecular formula $C_{33}H_{38}$ (molecular weight 434), and six have the molecular formula $C_{32}H_{36}$ (molecular weight 420). These two heptamantane families have structures showing greater internal bond strain, with correspondingly lower stabilities. The remaining two have the molecular formula $C_{30}H_{34}$ (molecular weight 394). Octamantanes possess eight of the "diamond crystal cage units" and exist within five families of different molecular weight core structures. Among the octamantanes, eighteen have the molecular formula $C_{34}H_{38}$ (molecular weight 446). Other octamantanes have the molecular formula $C_{38}H_{44}$ (molecular weight 500). The remaining octamantane families, $C_{37}H_{42}$ (molecular weight 486), $C_{36}H_{40}$ (molecular weight 472) and $C_{33}H_{36}$ (molecular weight 432) show greater bond strain and correspondingly lower stability. Nonamantanes exist within six families of different molecular weights having the following molecular formulas: $C_{42}H_{48}$ (molecular weight 552), $C_{41}H_{46}$ (molecular weight 538), $C_{40}H_{44}$ (molecular weight 524), $C_{38}H_{42}$ (molecular weight 498), $C_{37}H_{40}$ (molecular weight 484) and $C_{34}H_{36}$ (molecular weight 444). Additionally, decamantane exists within families of seven different molecular weights. Among the decamantanes, there is a single decamantane having the molecular formula $C_{35}H_{36}$ (molecular weight 456) which is structurally compact in relation to the other decamantanes and has low internal bond strain. The other decamantane families have the molecular formulas: $C_{46}H_{52}$ (molecular weight 604), $C_{45}H_{50}$ (molecular weight 590), $C_{44}H_{48}$ (molecular weight 576), $C_{42}H_{46}$ (molecular weight 550), $C_{41}H_{44}$ (molecular weight 536) and $C_{38}H_{40}$ (molecular weight 496). Undecamantanes exist as molecular formulas $C_{50}H_{56}$ (molecular weight 656), $C_{49}H_{54}$ (molecular weight 642), $C_{48}H_{52}$ (molecular weight 628), $C_{46}H_{50}$ (molecular weight 602), $C_{45}H_{48}$ (molecular weight 588), $C_{42}H_{44}$ (molecular weight 548), $C_{41}H_{42}$ (molecular weight 534), $C_{39}H_{40}$ (molecular weight 508). More preferred and less preferred higher diamondoids are based on their internal bond strain and corresponding stabilities which is reflected by their relative concentrations in the various feedstocks. FIG. 1B shows examples of higher diamondoid monomer structures (tetramantanes to undecamantanes) that contain one or two derivative (R) groups useful for polymer preparation. FIG. 1B gives examples showing that higher diamondoids have a great variety of shapes, dimensions and attachment sites for R groups. These variations will have significant effects in determining the properties of the polymers they will form. Also, FIGS. 5D-5F indicate that the rigidity of polymer structures formed from higher diamondoid monomers will vary greatly with the attachment sites of R groups on the monomers.

Figure 2A:
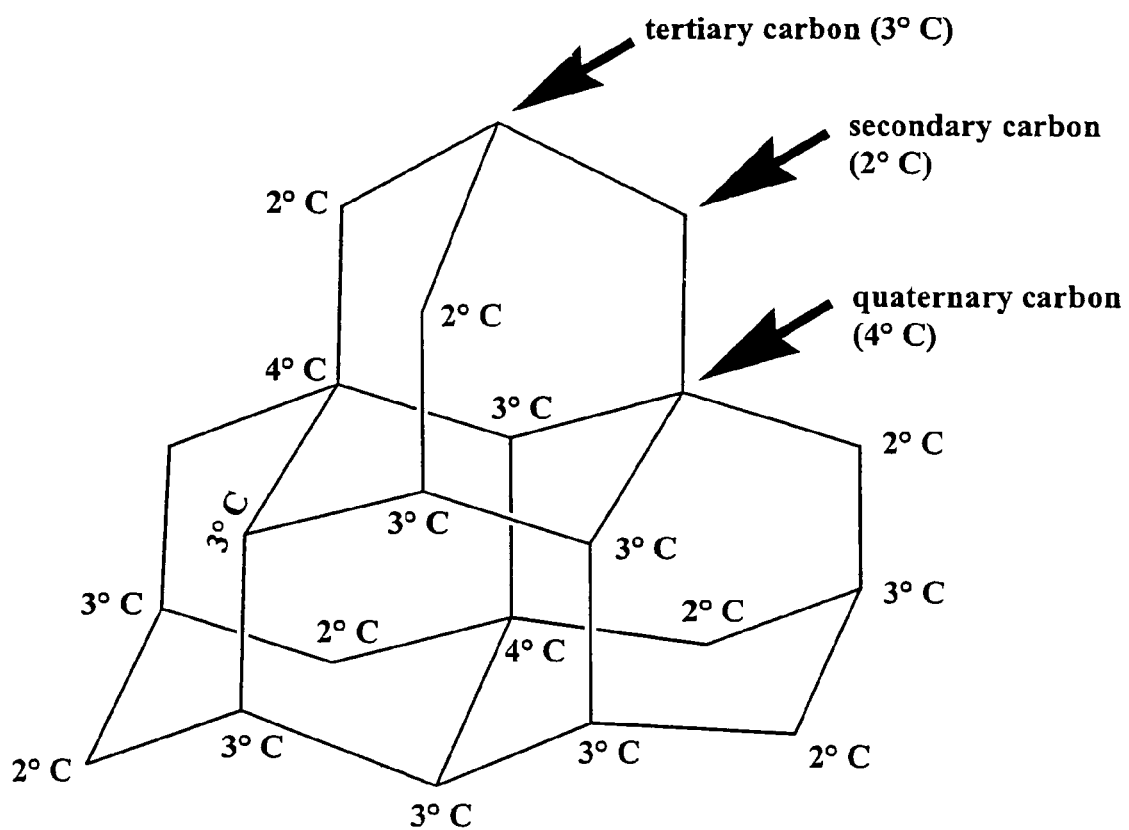
FIG. 2A illustrates that higher diamondoids (in this case [1(2)3]-tetramantane) have quaternary (4°), tertiary (bridgehead, 3°) and secondary (2°) carbons.
Figure 2C:
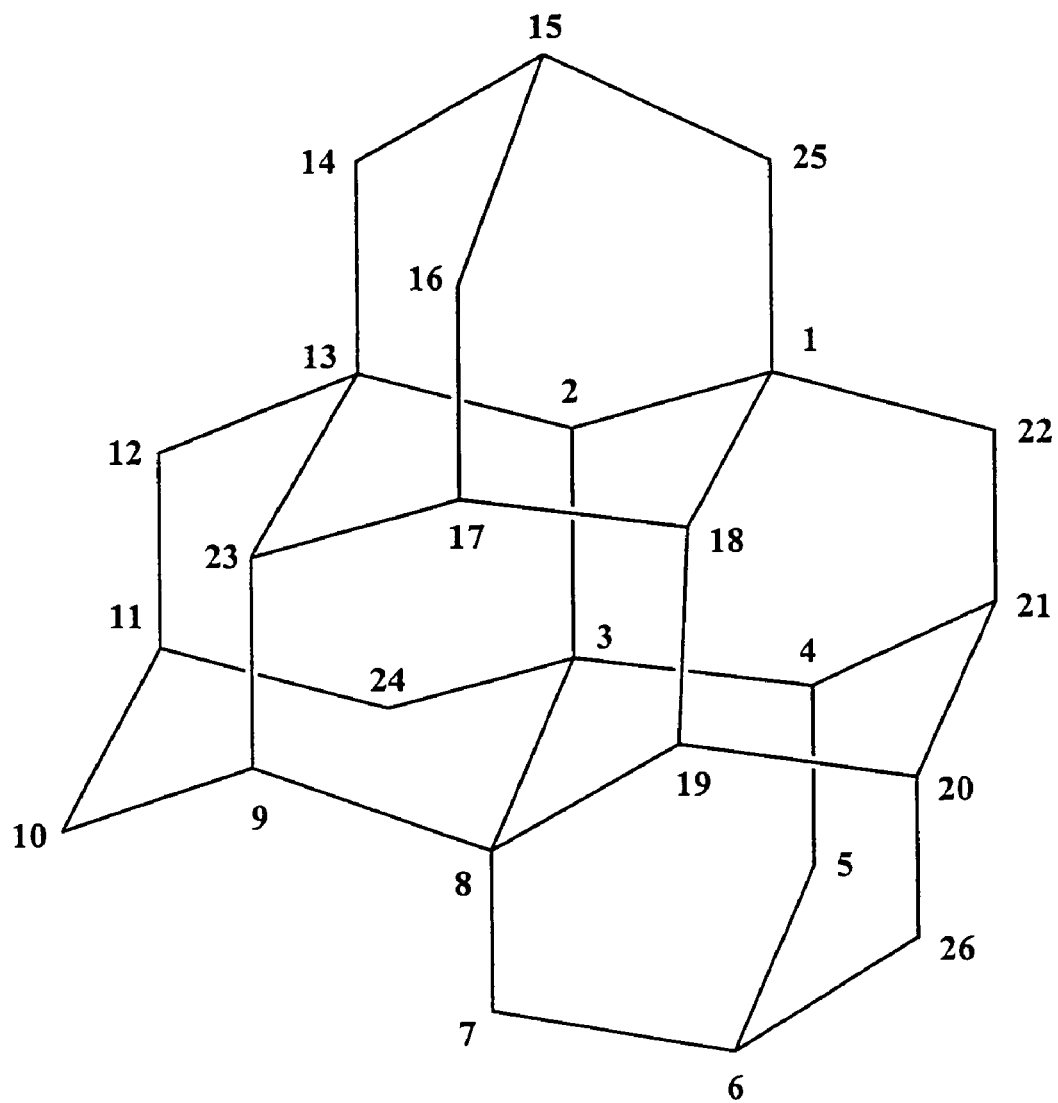
FIG. 2C shows the numbering scheme of a representative pentamantane.
Figure 2D:
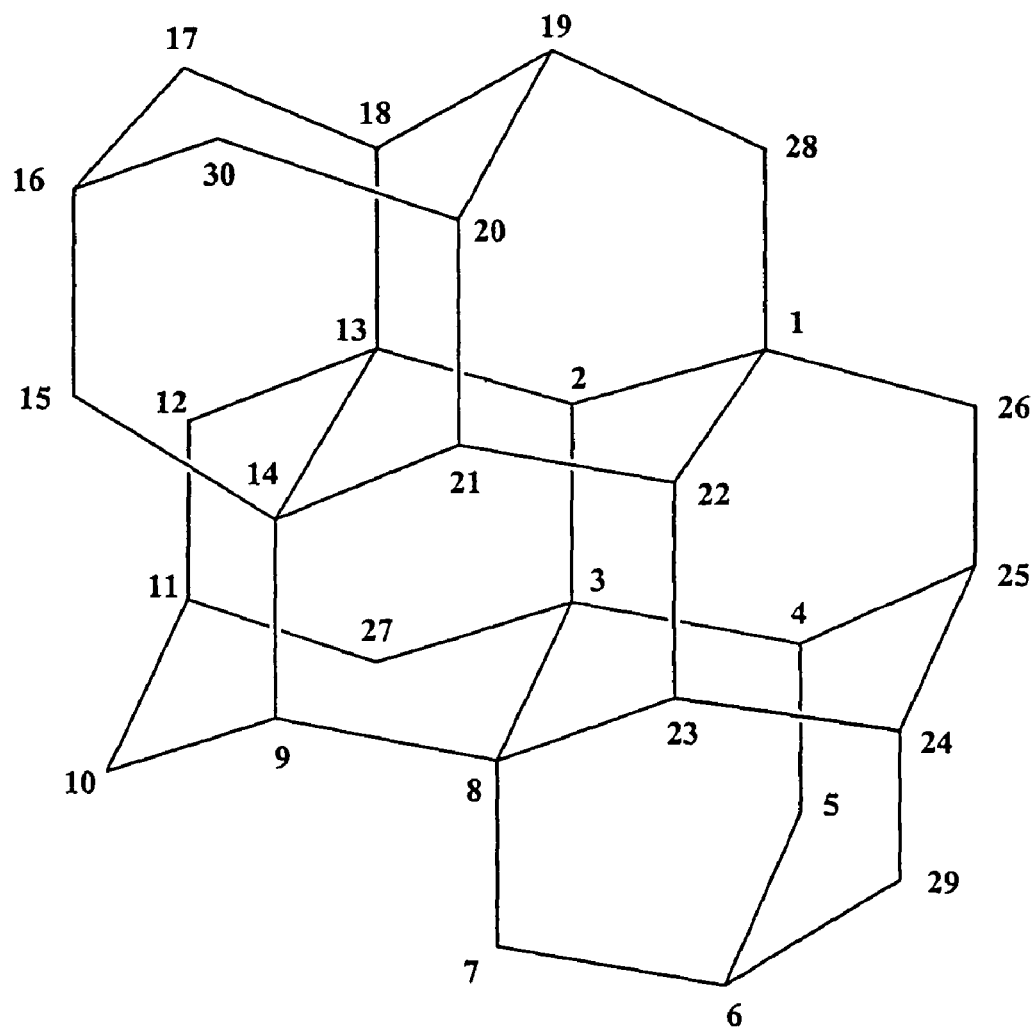
FIG. 2D shows the numbering scheme of a representative hexamantane.
Figure 2E:
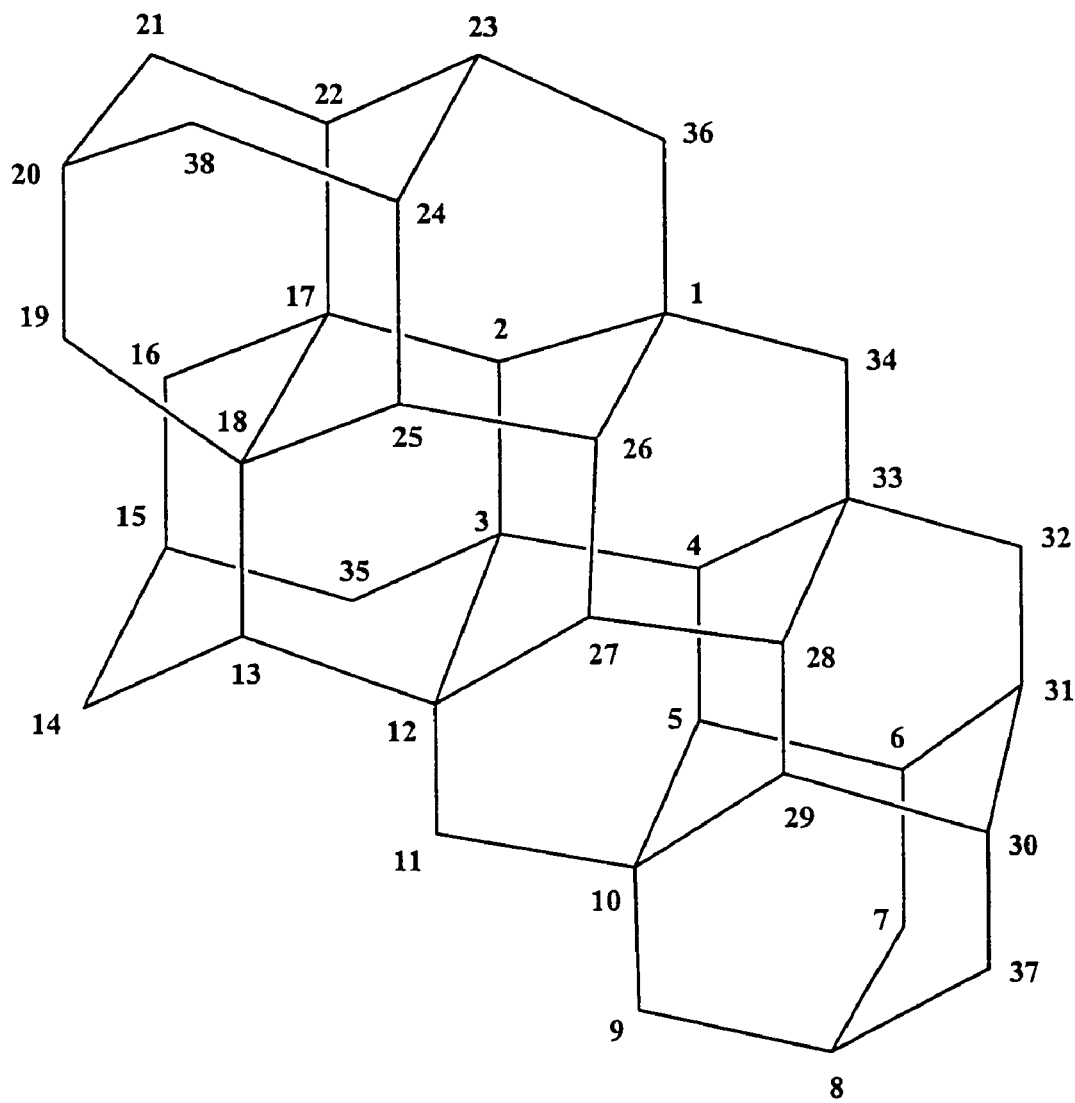
FIG. 2E shows the numbering scheme of a representative octamantane.
Figure 2F:
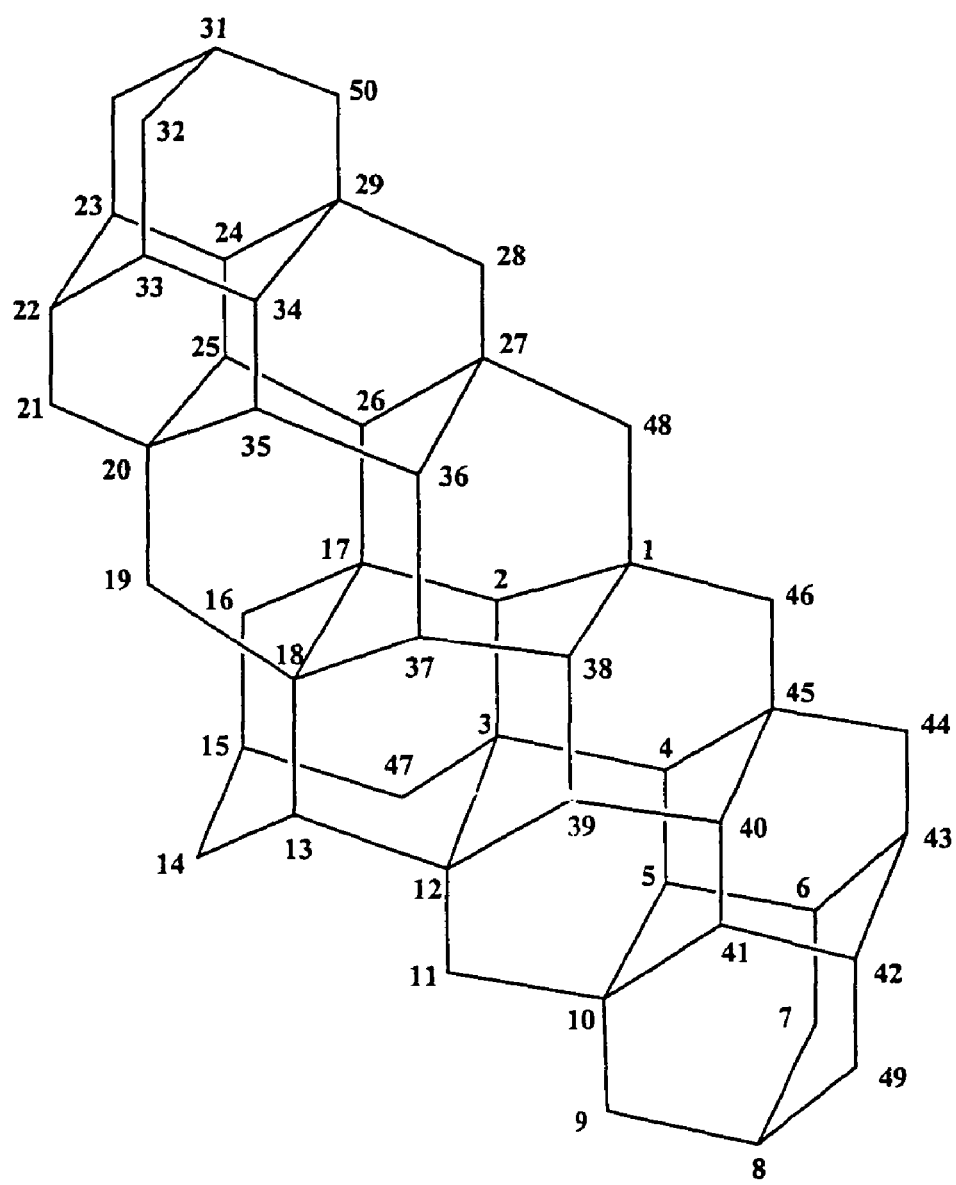
FIG. 2F shows the numbering scheme of a representative undecamantane.

FIG. 2A shows a representative carbon-numbering scheme for a tetramantane, in which the quaternary, tertiary, and secondary carbons are highlighted. Carbon numbering schemes for several representative higher diamondoids are illustrated in FIGS. 2B-2F.

After numbering the carbons atoms in a higher diamondoid, a determination of the number of equivalent tertiary and secondary carbons can be made. This can be based upon observations of molecular symmetry or it can be based upon computerized simulations of Nuclear Magnetic Resonance (NMR) spectra, which correlate with the symmetry of the caged molecule, i.e., equivalent carbons have identical NMR chemical shifts. FIG. 2B shows the structures of the four different tetramantanes. Each carbon is numbered. As shown, these tetramantanes have different numbers of equivalent and non-equivalent tertiary carbons.

FIG. 2C-2F show some examples of pentamantane, hexamantane, octamantane, and undecamantane diamondoids, respectively, and the numbering of their individual carbon atoms.

The higher diamondoid families contain multiple isomers (including stereoisomers) and substituted or derivatized diamondoids will typically contain one or more chiral centers. Higher diamondoids larger than tetramantane exist in forms with more than one molecular weight. If desired, such compounds can be isolated as pure isomers or stereoisomers (e.g., as individual enantiomers or diastereomers, or as stereoisomer-enriched mixtures). Pure stereoisomers (or enriched mixtures) may be prepared using, for example, crystallization, optically active solvents or stereo-selective reagents well-known in the art. Alternatively, racemic mixtures of such compounds can be separated using, for example, chiral column chromatography, chiral resolving agents and the like.

Higher diamondoids can be recovered from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures.

A feedstock is selected such that it comprises recoverable amounts of higher diamondoid components. Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include condensate feedstocks recovered from the Norphlet Formation in the Gulf of Mexico and from the LeDuc Formation in Canada. These feedstocks contain approximately 0.3 weight percent higher diamondoids, as determined by GC and GC/MS. These feedstocks are light colored and have API gravities in the 19 to 20° range.

Figure 7:
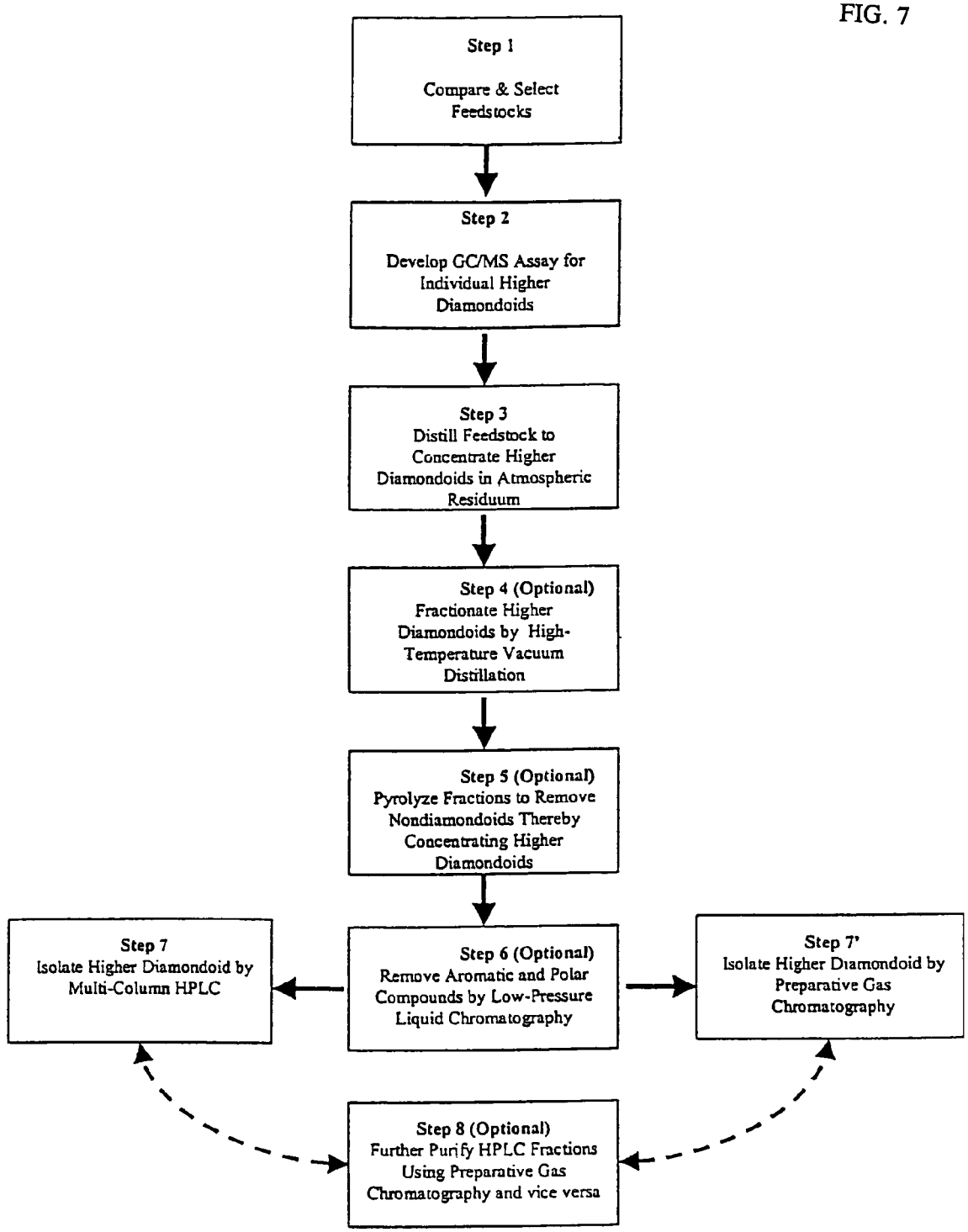
FIG. 7 gives a flow chart representing the various steps used in the isolation of higher diamondoid-containing fractions and individual higher diamondoid components. Note that the steps can in some cases be used in a different sequence and possibly skipped as discussed in the Examples.

The general isolation processes of higher diamondoids are shown in FIG. 7.

In one embodiment, the removal of contaminants includes distillation of the feedstock to remove non-diamondoid components as well as lower diamondoid components and in some cases other nonselected higher diamondoids having boiling points less than that of the lowest boiling point higher diamondoid component selected for recovery.

In a particularly preferred embodiment, the feedstock is distilled to provide cuts above and below about 335° C., atmospheric equivalent boiling point and, more preferably, above and below about 345° C. atmospheric equivalent boiling point. In either instance, the lower cuts, which are enriched in lower diamondoids and low boiling point non-diamondoid components are taken overhead and discarded and the higher boiling cut, which is enriched in higher diamondoids, is retained. It is understood, of course, that the temperature for the cut point during distillation is a function of pressure and that the above temperatures are referenced to atmospheric pressure. A reduced pressure will result in a lower distillation temperature to achieve the same cut point whereas an elevated pressure will result in a higher distillation temperature to achieve the same cut point. The correlation of pressure/temperature from atmospheric distillation to either reduced pressure or elevated pressure distillation is well within the skill of the art.

Distillation can be operated to fractionate the feedstocks and provide several cuts in a temperature range of interest to provide the initial enrichment of the selected higher diamondoids or groups of selected higher diamondoids. The cuts, which are enriched in one or more selected diamondoids or a particular diamondoid component of interest, are retained and may require further purification. The following Table illustrates representative fractionation points that may be used to enrich various higher diamondoids in overheads. In practice it may be advantageous to make wider temperature range cuts which would often contain groups of higher diamondoids which could be separated together in subsequent separation steps.

Fractionation Points

|  | Most Preferred | | Preferred | | Useful | |
| --- | --- | --- | --- | --- | --- | --- |
| Higher Diamondoid | Lower Cut Temperature (° C.) | Higher Cut Temperature (° C.) | Lower Cut Temperature (° C.) | Higher Cut Temperature (° C.) | Lower Cut Temperature (° C.) | Higher Cut Temperature (° C.) |
| Tetramantanes | 349 | 382 | 330 | 400 | 300 | 430 |
| Pentamantanes | 385 | 427 | 360 | 450 | 330 | 490 |
| Cyclohexamantanes | 393 | 466 | 365 | 500 | 330 | 550 |
| Hexamantanes | 393 | 466 | 365 | 500 | 330 | 550 |
| Heptamantanes | 432 | 504 | 395 | 540 | 350 | 600 |
| Octamantanes | 454 | 527 | 420 | 560 | 375 | 610 |
| Nonamantanes | 463 | 549 | 425 | 590 | 380 | 650 |
| Decamantanes | 472 | 571 | 435 | 610 | 390 | 660 |
| Undecamantanes | 499 | 588 | 455 | 625 | 400 | 675 |

It shall be understood that substituted higher diamondoids may accordingly shift these preferred cut-point temperatures to higher temperatures due to the addition of substituent groups. Additional temperature refinements will allow for higher purity cuts for the diamondoid of interest. FIG. 10 provides further illustrations of how fractionation can provide cuts enriched in individual or multiple higher diamondoid components.

It will be further understood that fractionation can be stopped before a selected higher diamondoid is taken overhead. In this case the higher diamondoid can be isolated from the fractionation bottoms.

Other processes for the removal of lower diamondoids, unselected higher diamondoids, if any, and/or hydrocarbonaceous non-diamondoid components include, by way of example only, size separation techniques, evaporation either under normal or reduced pressure, crystallization, chromatography, well head separators, reduced pressure and the like. Removal processes can utilize the larger sizes of the higher diamondoids to effect separation of lower diamondoids therefrom. For example, size separation techniques using membranes will allow a feedstock retained in the membrane to selectively pass lower diamondoids across the membrane barrier provided that the pore size of the membrane barrier is selected to differentiate between compounds having the size of higher diamondoid components as compared to lower diamondoid components. The pore size of molecular sieves such as zeolites and the like can also be used to effect size separation.

In a preferred embodiment, the removal process provides for a treated feedstock having a ratio of lower diamondoid components to higher diamondoid components of no greater than 9:1; more preferably, no greater than 2:1; and even more preferably, the ratio is no greater than 1:1. Even more preferably, after removal of the lower diamondoid component(s) from the feedstock, at least about 10%, more preferably at least 50% and still more preferably at least 90% of the higher diamondoid components are retained in the feedstock as compared to that amount found in the feedstock prior to the removal.

When recovery of hexamantane and higher diamondoid components is desired and when the feedstock contains non-diamondoid contaminants, the feedstock will also be generally subjected to pyrolysis to effect removal of at least a portion of the hydrocarbonaceous non-diamondoid components from the feedstock. The pyrolysis effectively concentrates the amount of higher diamondoids in the pyrolytically treated feedstock thereby rendering their recovery possible (FIG. 11).

Pyrolysis is effected by heating the feedstock under vacuum conditions or in an inert atmosphere, at a temperature of at least about 390° C. and, preferably, from about 400 to about 550° C., more preferably from about 400 to about 450° C., and especially 410 to 430° C.; for a period of time to effect pyrolysis of at least a portion of the non-diamondoid components of the feedstock. The specific conditions employed are selected such that recoverable amounts of selected higher diamondoid components are retained in the feedstock. The selection of such conditions is well within the skill of the art.

Preferably, pyrolysis is continued for a sufficient period and at a sufficiently high temperature to thermally degrade at least about 10% of the non-diamondoid components (more preferably at least about 50% and even more preferably at least about 90%) from the pyrolytically treated feedstock based on the total weight of the non-diamondoid components in the feedstock prior to pyrolysis.

In yet another preferred embodiment, after pyrolysis of the feedstock, at least about 10%, more preferably at least about 50%, and still more preferably at least about 90% of the higher diamondoid components are retained in the feedstock after pyrolytic treatment compared to that amount found in the feedstock prior to pyrolytic treatment.

In a preferred embodiment, removal of lower diamondoids and low boiling point hydrocarbonaceous non-diamondoid components from the feedstock precedes pyrolytic treatment. However, it is understood, that the order of these procedures can be inverted such that pyrolysis occurs prior to removal of lower diamondoids from the feedstock.

The pyrolysis procedure, while a preferred embodiment, is not always necessary. This arises because the concentration of higher diamondoids can be sufficiently high in certain feedstocks that the treated feedstock (after removal of the lower diamondoid components) can be used directly in purification techniques such as chromatography, crystallization, etc. to provide higher diamondoid components. However, when the concentration or purity of higher diamondoid components in the feedstock is not at the level to effect such a recovery, then a pyrolytic step should be employed.

Even when pyrolysis is employed, it is preferred to further purify the recovered feedstock using one or more purification techniques such as chromatography, crystallization, thermal diffusion techniques, zone refining, progressive recrystalization, size separation and the like. In a particularly preferred process, the recovered feedstock is first subjected to gravity column chromatography using silver nitrate impregnated silica gel followed by HPLC using two different columns of differing selectivities to isolate the selected diamondoids and crystallization to provide crystals of the highly concentrated target higher diamondoids. Where higher diamondoid concentrations are not high enough for crystallization to occur, further concentration by, for example, preparative capillary gas chromatography may be necessary.

Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the high diamondoids can be achieved using several approaches. One such approach is spontaneous crystallization with resolution and mechanical separation. This approach to enantiomer resolution can be enhanced by preparation of derivatives or by the use of additives, chiral solvents, or various types of seed crystals. Another resolution option is chemical separation under kinetic or thermodynamic control. Other suitable processes for enantiomer resolution include chiral separations, which can be performed using a gas chromatographic (GC) see "Chiral Chromatography", T. E. Beesley, et. al, Wiley, Johnson & Sons, January 1998, incorporated herein by references, by high performance liquid chromatographic (HPLC) and by supercritical fluid chromatographic (SFC) techniques, see Supercritical fluids in Chromatography and Extraction", R. M. Smith, Elsevier Science, December 1997, incorporated herein by references.

The examples illustrate methods for recovering various higher diamondoids from the tetramantanes to the undecamantanes.

The Higher Diamondoid Derivatives

A higher diamondoid derivative is a higher diamondoid which has had at least 1 and suitably from 1 to 6 of its hydrogens replaced by a covalent bond to a polymerizable moiety.

These higher diamondoid derivatives can be represented by Formula I below:

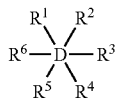

I wherein D is a higher diamondoid and, $R^1$, $R^2$, $R^3$, $R^4$, $R^5$ and $R^6$ are independently selected from a group consisting of hydrogen and one or more polymerizable moieties; provided there is at least one polymerizable moiety on the compound. Preferably, the compound contains either one or two polymerizable moieties.

These preferred materials may be represented by Formulae IA and IB below:

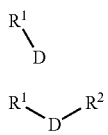

IA

IB

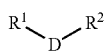

in which $R^1$ or $R^1$ and $R^2$ are the same or different polymerizable moieties. such as alkenyl, alkynyl, —OH, —$C_2H_3O$, —SH, —$NH_2$, —$CO_2H$, —$C_6H_5$, —$C_6H_4NH_2$, —$C_6H_4CO_2H$ or —$C_6H_4OH$.

The higher diamondoid, D, may preferably be selected from the: tetramantanes, pentamantanes, hexamantanes, heptamantanes, octamantanes, nonamantanes, decamantanes, and undecamantanes. These higher diamondoids may be substituted or unsubstituted. Individual isolated higher-diamondoid components may be used as well as mixtures of isomers from a single higher diamondoid family as well as mixtures of materials from several higher diamondoid families.

Of the higher diamondoids, the tetramantanes and pentamantanes are the most plentiful. The very high molecular weight materials such as decamantanes and undecamantanes are the least plentiful. Each family can offer unique structures and properties, however. Thus, while availability favors the tetramantanes and pentamantanes and hexamantanes, there may be compelling reasons to select others as well.

The polymerizable moieties which make up $R^1$—$R^6$ can be selected from groups which can participate in a polymerization reaction. These include vinyls (alkenyls), alkynyls, epoxides, cyclic ethers sucil as ethoxites, hydroxyls, aldehyde, cyanos, siloxyls, cyanates, and the like.

These groups are capable of participating in addition polymerization, condensation polymerizations, and the like. In some cases, such as vinyl polymerizations, a single polymerizable group can form an addition polymer. In other cases, two different polymerizable groups may need to react with one another to effect polymerization, for example an acid and an amine reacting to form an amide-linked polymer.

Other examples of covalent bonds formed from complementary reactive groups are documented in the art. Representative complimentary groups are depicted in the Table 1.

TABLE 1

| Complementary Polymerization Chemistries | | |
|---|---|---|
| Diamondoid Polymerizable Group | Reactive Group on Second Diamondoid Or Linking Group | Covalent Linkage |
| Hydroxyl | Isocyanoate | Urethane |
| Epoxide | Hydroxyl | Ether |
| Carboxyl | Amine | Amide |
| Amine | Carboxyl | Amide |
| Vinyl | Vinyl | Alkylene |
| Thiol | Epoxide | Thioether |

In addition to these R groups, the polymerizable moieties can include groups that are capable of linking the higher diamondoids to preformed polymers. For example, an acid $R^1$—$R^6$ group could react with an amine on a polymer to attach a higher diamondoid through an amide link. A wide range of moieties can serve this role. Examples of these latter $R^1$—$R^6$ groups include —F, —Cl, —Br, —I, —OH, —SH, —$NH_2$, —$NHCOCH_3$, —NHCHO, —$CO_2H$, —$CO_2R'$, —COCl, —CHO, —$CH_2OH$, =O, —$NO_2$, —CH=$CH_2$, —C≡CH and —$C_6H_5$; where R' is alkyl (preferably ethyl).

Suitable $R^1$—$R^6$ groups may also be described by the following structure: —$(X)_m$—$(Y)_n$—Z, wherein X is —O—, —NR—, —OC(O)—, —$NR^8C(O)$—, —C(O)O— or —$C(O)NR^9$—, wherein $R^7$, $R^8$ and $R^9$ are independently hydrogen or alkyl; Y is alkylene, arylene, alkarylene, heteroarylene or alkheteroarylene; Z is alkenyl, alkynyl, —OH, —$C_2H_3O$, —SH, —$NH_2$, —$CO_2H$, —$C_6H_5$, —$C_6H_4NH_2$, —$C_6H_4CO_2H$ or —$C_6H_4OH$; m is 0 or 1; and n is 0 or 1.

Preferably, X is selected from a group consisting of —O—, —$NR^7$— and —C(O)O—. Preferably, Z is selected from a group consisting of ethenyl, ethynyl, propenyl, propynyl, isobutenyl, butynyl, —$NH_2$, —$CO_2H$ and —OH.

In one preferred embodiment, m and n are zero and Z is selected from a group consisting of ethenyl, ethynyl, propenyl, propynyl, isobutenyl, butynyl, —$NH_2$, —$C_2H_3O$, —$CO_2H$, —OH and —SH.

In another preferred embodiment, Z is ethenyl, ethynyl, propenyl, propynyl, isobutenyl or butynyl, and X is —O—, —OC(O)— or —C(O)O— and m is 1 and n is 0.

In another preferred embodiment, Z is —OH, —$NH_2$, —$C_2H_3O$ or —$CO_2H$, and more preferably —$NH_2$, —$C_2H_3O$ or —$CO_2H$, while m is 0, and Y is alkylene or arylene.

In still another preferred embodiment, Z is —$C_2H_3O$ or —SH, m is 0, and Y is alkylene.

Other preferred embodiments include, for instance: where Z is —$C_6H_5$, —$C_6H_4NH_2$, —$C_6H_4CO_2H$ or —$C_6H_4OH$, m is 0, and n is 0. In another preferred embodiment Z is ethenyl, ethynyl, propenyl, propynyl, isobutenyl or butynyl, m is one and X is —O—, —OC(O)— or —C(O)O—, and n is one and Y is —$CH_2$— or —$(CH_2)_2$—.

More preferred higher diamondoid derivatives include materials of formulae I and IA and IB wherein $R^1$ and $R^2$ are independently selected from —F, —Cl, —Br, —I, —OH, —SH, —$NH_2$, —$NHCOCH_3$, —NHCHO, —$CO_2H$, —$CO_2R'$, —COCl, —CHO, —$CH_2OH$, =O, —$NO_2$, —CH=$CH_2$, —C≡CH and —$C_6H_5$; where R' is alkyl (preferably ethyl).

The Higher Diamondoid Intermediates

The higher diamondoid derivatives may often be formed going through intermediates referred to as "higher diamondoid intermediates". In some cases an intermediate may be polymerizable in its own right.

The higher diamondoid intermides may be represented by Formula II below:

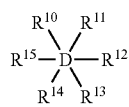

II wherein D is a higher diamondoid nucleus and at least one of $R^{10}$—$R^{15}$ is a covalently-attached moiety replacing a hydrogen which can be converted to a polymerizable moiety or which, in some cases, may be a polymerizable moiety as well. The remaining R's are hydrogens. Preferred intermediates have one or two nonhydrogen R's and are represented by Formulae IIA and IIB:

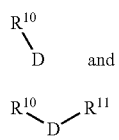

IIA

IIB wherein $R^{10}$ and $R^{11}$ are nonhydrogen moieties capable of conversion to polymerizable moieties or capable of serving as polymerizable moieties.

In view of the broad definition of these intermediates, they can include the polymerizable moieties defined above but also can include a wide range of halos, aldehydes, amines, alcohols, thiols, alkyls, aryls and the like.

In Formulae II, IIA and IIB examples of $R^{10}$—$R^{15}$ include —H, —F, —Cl, —Br, —I, —OH, —SH, —$NH_2$, —$NHCOCH_3$, —NHCHO, —$CO_2H$, —$CO_2R'$, —COCl, —CHO, —$CH_2OH$, =O, —$NO_2$, —CH=$CH_2$, —C≡CH and —$C_6H_5$; where R' is alkyl (preferably ethyl) provided that $R^{10}$, $R^{11}$, $R^{12}$, $R^{13}$, $R^{14}$ and $R^{15}$ are not all hydrogens.

These intermediates may be synthesized and isolated or may be present in reaction mixtures. In either event they are generally present in concentrations of at least about 100 ppm and usually at least 1000 ppm or even greater, such as at least about 1% by weight.

Methods for Preparing of Higher Diamondoid Derivatives and Intermediates

There are two major reactions for the preparation of higher diamondoid derivatives and intermediates: nucleophilic ($S_N1$-type) and electrophilic ($S_E2$-type) substitution reactions (details for such reactions and their mechanisms for lower diamondoids, see, for instance, "*Recent developments in the adamantane and related polycyclic hydrocarbons*" written by R. C. Bingham and P. v. R. Schleryer as a part of the book: "*Chemistry of Adamantanes*", Springer-Verlag, Berlin Heidelberg, New York, 1971; "*Reactions of adamantanes in electrophilic media*" by I. K. Moiseev, N. V. Makarova, M. N. Zemtsova published in *Russian Chemical Review*, 68(12), 1001-1020 (1999); "*Cage hydrocarbons*" edited by George A. Olah, John Wiley & Son, Inc., New York, 1990).

$S_N1$ reactions involve the generation of higher diamondoid carbocations, which subsequently react with various nucleophiles. Such nucleophiles include, without limitation the following: water (providing hydroxylated higher diamondoids); halide ions (providing halogenated higher diamondoids); ammonia (providing aminated higher diamondoids); azide (providing azidylated higher diamondoids); nitriles ("Ritter reaction," providing aminated higher diamondoids after hydrolysis); carbon monoxide ("Koch-Haaf reaction," providing carboxylated diamondoids after hydrolysis); olefins (providing alkenylated higher diamondoids after deprotonation); and aromatic compounds (providing arylated higher diamondoids after deprotonation). The reactions occur similarly to those of open chain alkyl systems, such as t-butyl, t-cumyl and cycloalkyl systems. Since tertiary (bridgehead) carbons of higher diamondoids are considerably more reactive than secondary carbons under $S_N1$ reaction conditions, substitution at the tertiary carbons is favored.

Figure 3A:
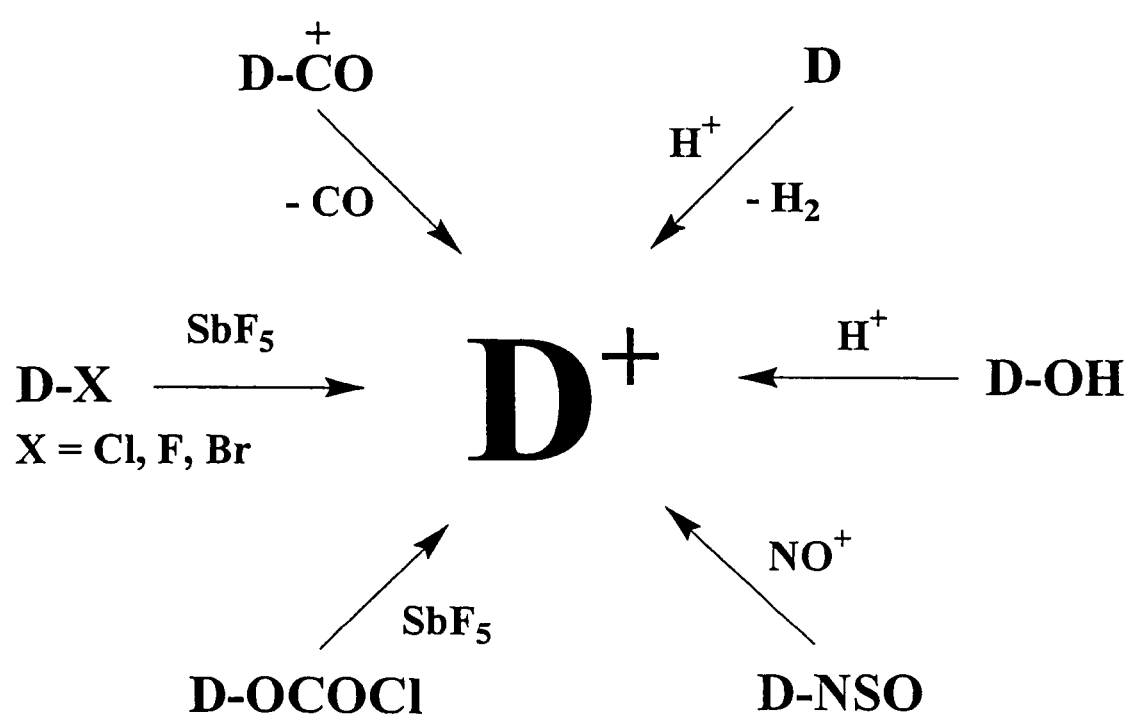
FIG. 3A shows representative pathways by which higher diamondoid carbocations are generated during the synthesis of diamondoid derivatives.
Figure 3B:
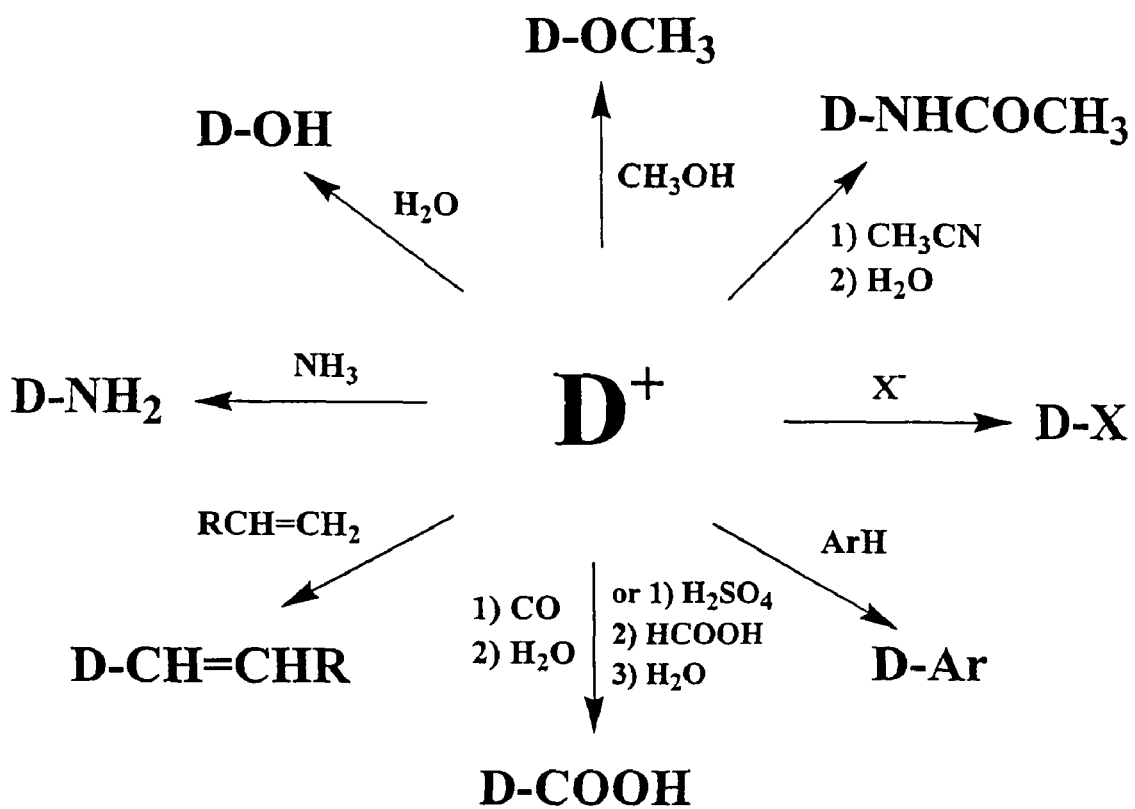
FIG. 3B shows representative pathways by which higher diamondoids are derivatized via higher diamondoid carbocations ($S_N1$ reactions).

An illustration of representative pathways by which higher diamondoid carbocations are generated is shown in FIG. 3A, wherein D is a higher diamondoid nucleus. Preferably the carbocation is generated from a parent higher diamondoid, a hydroxylated higher diamondoid intermediate or a halogenated higher diamondoid intermediate. FIG. 3B shows representative $S_N1$ reaction pathways by which these higher diamondoid carbocations can react to form higher diamondoid derivatives and intermediates. Intermediates expressed in the figures can be further derivatized (e.g., amide from amine or ester from alcohol) or reacted under appropriate conditions to provide desired derivatives.

Figure 3C:
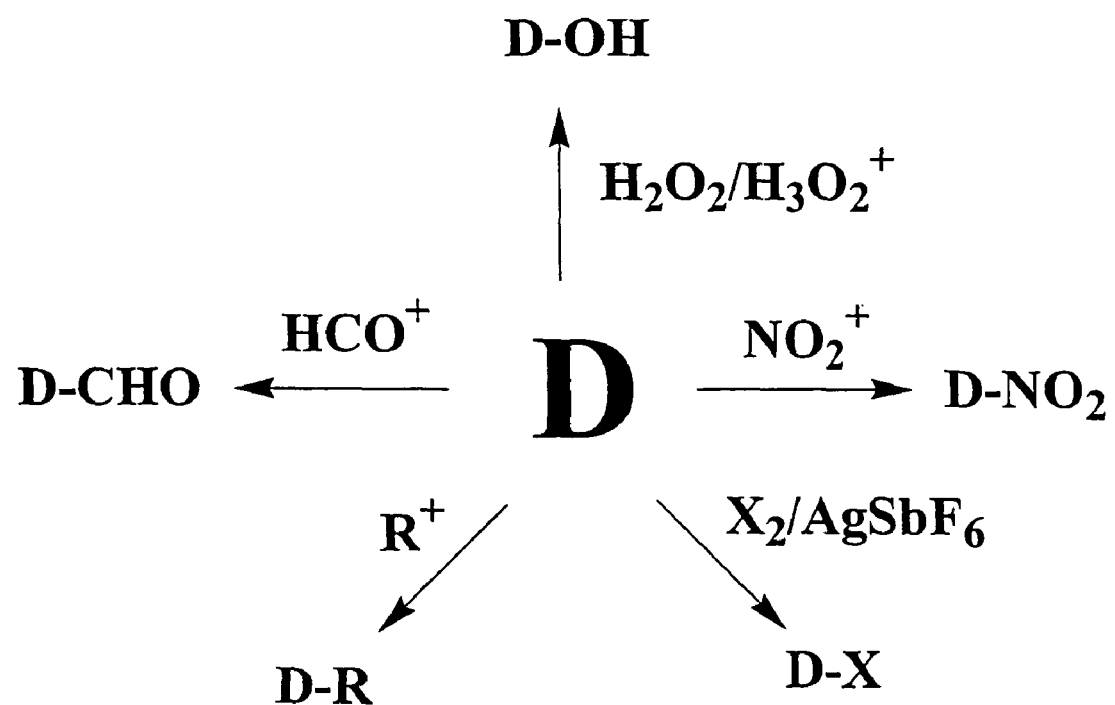
FIG. 3C shows representative pathways by which higher diamondoids are derivatized via eletrophilic substitution reactions ($S_E2$ reactions).

$S_E2$-type reactions (i.e., an electrophile substitution of a C—H bond via a five-coordinate carbocation intermediate) include, but are not limited to, the following reactions: hydrogen-deuterium exchange upon treatment with deuterated superacids (e.g., DF-$SbF_5$ or $DSO_3F$-$SbF_5$); nitration upon treatment with nitronium salts, such as $NO_2^+BF_4^-$ or $NO_2^+PF_6^-$ in the presence of superacids (e.g., $CF_3SO_3H$); halogenation upon, for instance, reaction with $Cl_2$+$AgSbF_6$; alkylation of the bridgehead carbons under Friedel-Crafts conditions (i.e., $S_E2$-type σ alkylation); carboxylation under Koch reaction conditions; and, oxygenation under $S_E2$-type σ hydroxylation conditions (e.g., hydrogen peroxide or ozone using superacid catalysis involving $H_3O_2^+$ or $HO_3^+$, respectively). An illustration of representative pathways by which higher diamondoids are derivatized via eletrophilic substitution reactions ($S_E2$ reactions) is shown in FIG. 3C.

Of the two major reactions for the derivatization of higher diamondoids, the $S_N1$-type is preferred.

Mono- and multi-brominated higher diamondoids are some of the most versatile intermediates in the derivative chemistry of higher diamondoids. These intermediates are used in, for example, the Koch-Haaf, Ritter, and Friedel-Crafts alkylation/arylation reactions. Brominated higher diamondoids are prepared by two different general routes. One involves direct bromination of the higher diamondoids or substituted higher diamondoids with elemental bromine in the presence or absence of a Lewis acid (e.g. $BBr_3$—$AlBr_3$) catalyst. The other involves the substitution reaction of hydroxylated higher diamondoids with hydrobromic acid.

Direct bromination of higher diamondoids is highly selective, favoring substitution at the bridgehead (tertiary) carbons. By proper choice of catalyst and reaction conditions, one, two, three, four, or more bromine moieties can be introduced sequentially into the molecule, all at bridgehead positions. In the absence of a catalyst, the mono-bromo derivative is the major product with minor amounts of higher bromination products being formed. However, by use of suitable catalysts (e.g., boron bromide and/or aluminum bromide), di-, tri-, tetra-, penta-, and higher bromide derivatives of higher diamondoids are isolated as major products in the bromination reaction. Typically, the tetrabromo or higher bromo derivatives are synthesized at elevated temperatures in a sealed tube.

Bromination reactions of higher diamondoids are usually terminated by pouring the reaction mixture onto ice or ice water and adding a suitable amount of chloroform, or ethyl ether, or carbon tetrachloride, to the ice mixture. Excess bromine is then removed by distillation under vacuum with the addition of solid sodium disulfide or sodium hydrogen sulfide. The organic layer is separated and the aqueous layer is extracted with chloroform, or ethyl ether, or carbon tetrachloride. This is repeated 2-3 times. The resulting organic layers are then combined and washed with aqueous sodium hydrogen carbonate and water, and dried.

To isolate the brominated derivatives, the solvent is typically removed under vacuum. Typically, the reaction mixture is subjected to column chromatography on either alumina or silica gel using standard elution conditions (e.g., eluting with light petroleum ether, n-hexane, or cyclohexane, or mixtures thereof, with ethyl ether) to separate out the bromo higher diamondoid. Separation by preparative gas chromatography (GC) or high performance liquid chromatography (HPLC) can also be often used where normal column chromatography is difficult and/or the reaction is performed on extremely small quantities of material.

To prepare bromo derivatives where the bromos are present on secondary carbons, for example, the corresponding hydroxylated higher diamondoid hydroxylated at the secondary sites is treated under mild conditions with hydrobromic acid. Hydroxlyation of higher diamondoids is less selective than bromination, allowing the preparation of compounds functionalized at secondary carbons. Preferably, higher diamondoids hydroxylated at secondary carbons are prepared by the reduction of the corresponding keto derivative.

For the general synthesis of higher diamondoid compounds substituted at secondary carbons, free radical reactions are often employed. These types of reactions provide a higher ratio of secondary to tertiary substitution than do the nucleophilic reactions. Photochlorination is a particularly useful free radical reaction, since chloro higher diamondoid derivatives are similar to bromo compounds in reactivity.

Notwithstanding the above, several other reactions can be used to functionalize higher diamondoids. The following reactions are illustrative of some of these methods. For instance, higher diamondoids can be halogenated in the following manner. As an example, fluorination of a higher diamondoid is carried out by reacting the higher diamondoid with a mixture of polyhydrogen fluoride and pyridine (30% Py, 70% HF) in the presence of nitronium tetrafluoroborate. Sulfur tetrafluoride reacts with a higher diamondoid in the presence of sulfur monochloride to afford a mixture of mono-, di-, tri- and even higher fluorinated higher diamondoids. Higher diamondoids are brominated upon treatment with bromine. This reaction can be carried out either in the presence or absence of a Lewis acid (e.g., $BBr_3$—$AlBr_3$). Iodo higher diamondoids are obtained by a substitutive iodination of chloro, bromo or hydroxyl higher diamondoids.

Higher diamondoids can be functionaiized by other groups, they are nitrated by concentrated nitric acid in the presence of glacial acetic acid under high temperature and pressure. Higher diamondoidones are synthesized by photo-oxidation in the presence of peracetic acid followed by treatment with chromic acid-sulfuric acid. Higher diamondoidones are reduced by, for instance, $LiAlH_4$, to hydroxylated higher diamondoids at the secondary carbons. 2,2-bis(4-hydroxyphenyl) higher diamondoids or 2,2-bis(4-aminophenyl) higher diamondoids are directly synthesized by the acid-catalyzed (HCl-catalyzed) condensation of higher diamondoidones with excess phenol or aniline in the presence of hydrogen chloride.

Reaction of the brominated derivatives with hydrochloric acid in dimethylformamide (DMF) converts the compounds to the corresponding hydroxylated derivatives. Brominated or iodinated higher diamondoids are converted to thiolated higher diamondoids by way of, for instance, reacting with thioacetic acid to form higher diamondoid thioacetates followed by removal of the acetate group under basic conditions. The amino derivatives are also synthesized from the brominated derivatives by heating them in the presence of formamide and subsequently hydrolyzing the resultant amide.

Direct hydroxylation is also effected on higher diamondoids upon treatment with N-hydroxyphthalimide and a binary co-catalyst in acetic acid. The hydroxylated derivatives are esterified, for example, under standard conditions such as reaction with an activated acid derivative (e.g., $CH_2\!\!=\!\!CHCOCl$, $CH_3CH\!\!=\!\!CHCOCl$ or $(CH_3)_2C\!\!=\!\!CHCOCl$). Alkylation is performed on the hydroxylated compounds through nucleophilic displacement on an appropriate alkenyl halide (e.g., $CH_2\!\!=\!\!CHCH_2Br$, $CH_3CH\!\!=\!\!CHCH_2Br$ or $(CH_3)_2C\!\!=\!\!CHCH_2Br$).

Similarly to the hydroxylated compounds, aminated higher diamonds are acylated or alkylated. For instance, reaction of an amino higher diamondoid with an activated acid derivative produces the corresponding amide. Alkylation is typically performed by reacting the amine with a suitable carbonyl containing compound (e.g., $CH_2\!\!=\!\!CH(CH_2)_3CHO$) in the presence of a reducing agent (e.g., sodium cyanoborohydride).

Carboxylated derivatives are obtained from the reaction of hydroxylated derivatives with formic acid. The derivatives are esterified through activation (e.g., conversion to acid chloride) and subsequent exposure to an appropriate alcohol (e.g., $CH_2\!\!=\!\!CHCH_2OH$, $CH_3CH\!\!=\!\!CHCH_2OH$ or $(CH_3)_2C\!\!=\!\!CHCH_2OH$). Amide formation is performed through activation of the carboxylated derivative and reaction with a suitable amine (e.g., $CH_2$=$CHCH_2NH_2$, $CH_3CH$=$CHCH_2NH_2$ or $(CH_3)_2C$=$CHCH_2NH_2$).

Ethenylated higher diamondoid derivatives are synthesized by reacting a brominated higher diamondoid with ethylene in the presence of $AlBr_3$ followed by dehydrobromination with potassium hydroxide or the like. The ethenylated compound is transformed into the corresponding epoxide under standard reaction conditions (e.g., 3-chloroperbenzoic acid). Oxidative cleavage (e.g., ozonolysis) of the ethenylated higher diamondoid affords the related aldehyde. The ethynylated higher diamondoid derivatives are obtained by treating a brominated higher diamondoid with vinyl bromide in the presence of $AlBr_3$. The resultant product is dehydrohalogenated using potassium t-butoxide in dimethyl sulfoxide (DMSO) to provide the desired compound.

The following table (Table 2) provides a representative list of higher diamondoid intermediate groups that are used for the production of polymerizable higher diamondoid derivatives.

TABLE 2

Higher Diamondoid Intermediate Substituent Groups

| HIGHER DIAMONDOID | SUBSTITUENT |
|---|---|
| tetramantane - undecamantane | F |
| tetramantane - undecamantane | Cl |
| tetramantane - undecamantane | Br |
| tetramantane - undecamantane | I |
| tetramantane - undecamantane | OH |
| tetramantane - undecamantane | $CO_2H$ |
| tetramantane - undecamantane | $CO_2CH_2CH_3$ |
| tetramantane - undecamantane | COCl |
| tetramantane - undecamantane | SH |
| tetramantane - undecamantane | CHO |
| tetramantane - undecamantane | $CH_2OH$ |
| tetramantane - undecamantane | $NH_2$ |
| tetramantane - undecamantane | $NO_2$ |
| tetramantane - undecamantane. | =O (keto) |
| tetramantane - undecamantane | CH=$CH_2$ |
| tetramantane - undecamantane | C≡CH |
| tetramantane - undecamantane | $C_6H_5$ |
| tetramantane - undecamantane | $NHCOCH_3$ |
| tetramantane - undecamantane | NHCHO |

Polymerization of Higher Diamondoid Derivatives

Polymerizable higher diamondoid derivatives are subjected to suitable reaction conditions so that polymers, e.g., homopolymers or co-polymers, are produced. Polymerization is typically carried out using one of the following different methods: free radical polymerization, cationic polymerization, anionic polymerization or polycondensation reactions.

Free radical polymerization occurs spontaneously upon the absorption of an adequate amount of heat, ultraviolet light or high-energy radiation. Typically, however, this polymerization process is induced by the addition of a small amount of an initiator such as peroxides, azo compounds, Lewis acids ard organometallic agents. Examples of initiators include, without limitation, the following: aceyl and benzoyl peroxide, alkyl peroxides such as cumyl and t-butyl, hydroperoxides, peresters, azobisisobutyronitrile, di-t-butylperoxide and benzophenone.

Free radical polymerization can be conducted either on the underivatized or derivatized higher diamondoid provided that the derivatized higher diamondoid contains a functional group amenable to free radical polymerization. In the case of the underivatized higher diamondoid, or preferably using a higher diamondoid derivative as the starting material, such as a monobromo or dibromo substituted higher diamondoid, a covalent bond is formed between two of the higher diamondoid components. Such a polymer formed can be represented generically by $(D)_r$-D where D is independently one or more higher diamondoid groups and r is an integer from 1 to 1,000,000, and preferably from 1 to 1000.

For cationic polymerization, a cationic catalyst is used to promote the reaction. Suitable catalysts are typically Lewis acid catalysts, such as boron trifluoride or aluminum trichloride. These polymerization reactions are usually conducted in solutions at low temperature (e.g., −80 to −100° C.).

Subjecting the derivative to anionic polymerization typically involves the addition of a strong nucleophile. Such nucleophiles include, for example, Grignard reagents and other organometallic compounds. Anionic polymerization reactions are oftentimes facilitated through the removal of water and oxygen from the medium, as those substances tend to terminate the polymerization reaction.

Where the polymerizable moiety is a suitable nucleophile (e.g., alcohol, amine and thiol) or electrophile (e.g., activated carboxylic acid derivative and epoxide), polymerization typically occurs through a polycondensation reaction. Examples of higher diamondoid-containing polymers that are formed using such a method include polyesters, polyamides, polyimides, polyaspartimides, polyamideimides, polyethers and so on, are formed where a higher diamondoid derivative is substituted such that it contains at least two different groups that can couple to one another (e.g., amine and carboxylic acid to form an amide). Heteropolymers, e.g. copolymers, in contrast, are formed where the higher diamondoid derivative is substituted such that it contains at least two groups (e.g., two carboxylic acid groups) that can couple to other bifunctional monomer(s), a linker such as (e.g., 1,3-diaminopropane).

The following are examples of polycondensation reactions involving higher diamondoid derivatives with a suitable linker: reaction of diepoxy higher diamondoid derivatives in the presence of a suitable diol (e.g., diethylene glycol) under either basic or acid conditions to form polyethers; reaction of bisphenolic higher diamondoid derivatives with aromatic dicarboxylic acids or activated dicarboxylic acids (e.g., acid chlorides) using pyridine as an HCl quencher at a relatively high temperature to form polyesters; reaction of bisphenolic higher diamondoid derivatives with activated aromatic dihalides (i.e., nucleophilic aromatic substitution polymerization) in N,N-dimethylacetamide (DMAc) in the presence of potassium carbonate under reflux to form poly(aryl ethers); reaction of bisphenolic higher diamondoid derivatives and aromatic bisphenols in different molar ratios with activated aromatic dihalides to form co-polymers; reaction of diamino higher diamondoid derivatives with aromatic dicarboxylic acids in the presence of triphenyl phosphite and pyridine to form polyamides; reaction of diamino higher diamondoid derivatives with aromatic tetracarboxylic dianhydrides in the presence of DMAc and an equimolar mixture of acetic anhydride and pyridine to form polyimides; reaction of diamino higher diamondoid derivatives with aromatic tetracarboxylic dianhydrides in m-cresol under reflux to form polyimides; reaction of diamino higher diamondoid derivatives with bis (3-ethyl-5-methyl-4-maleimidophenyl)methane in m-cresol in the presence of glacial acetic acid to form linear polyaspartimides; and, reaction of dicarboxyl higher diamondoid derivatives with diamines or dialcohols under suitable polycondensation conditions to form polyesters, polyamides or polyamide-imides.

As shown in FIGS. 4A-4H, the higher diamondoids can be incorporated into polymers in a wide range of configurations.

Figure 4A:
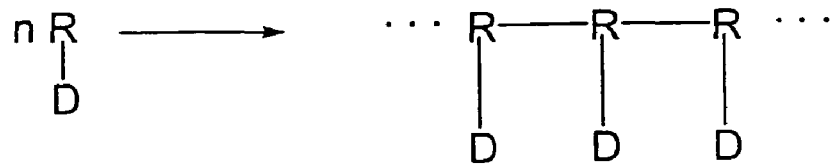
FIGS. 4A-4H are eight schematic chemical formulae and equations showing the structures and preparation of eight representative higher diamondoid-containing polymers.

FIG. 4A shows a homopolymer in which the higher diamondoid is a recurring unit pendant from the polymer backbone.

Figure 4B:
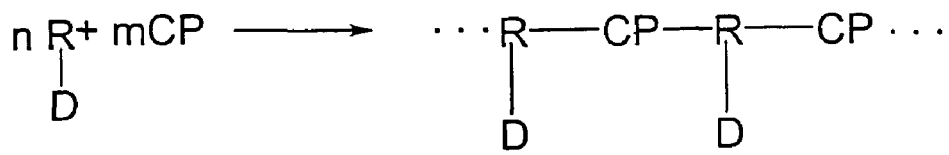
Figure 4C:
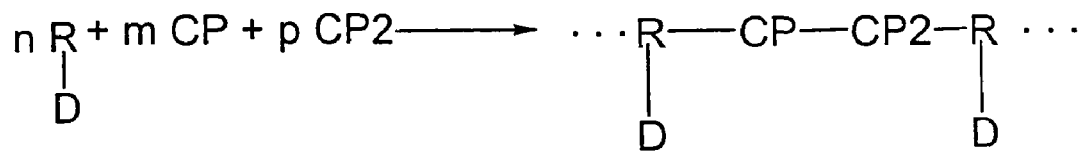

FIGS. 4B and 4C show copolymers or terpolymers where CP and CP2 are one or more copolymeric units, and the diamondoid is again pendant. When copolymeric units are present, their proportion to the proportion of higher diamondoid, for instance the ratio of n to m in the polymer of 4B or the ratio of n to m+p in the polymer of 4C can vary widely. Proportions (based on number of units) can range from 1 part higher diamondoid/0-1000 parts copolymeric unit with ratios of 1 part higher diamondoid/0-500 parts of copolymeric unit being preferred.

Figure 4D:
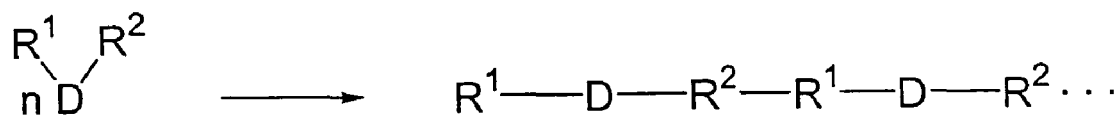
Figure 4E:
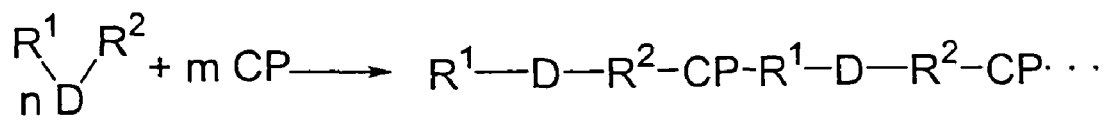

The higher diamondoid can also be incorporated into the backbone, per se. A representative homopolymer is shown in FIG. 4D and a copolymer is shown in FIG. 4E.

Figure 4F:
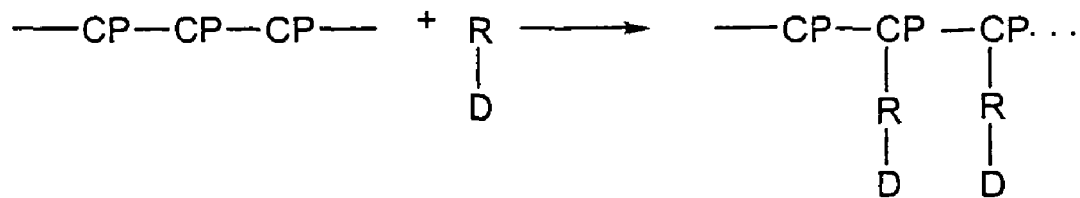
Figure 4G:
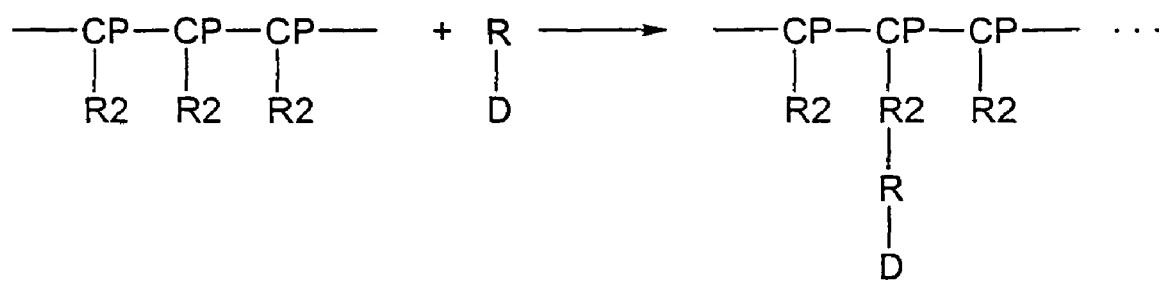

As shown in FIGS. 4F and 4G, a polymer can also have a preformed backbone with the diamondoids pendant from it.

Figure 4H:
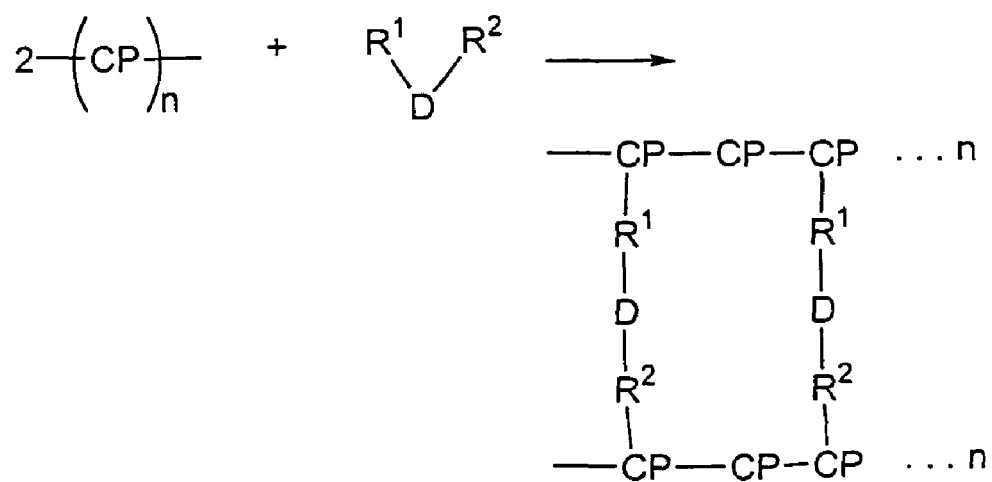

As shown in FIG. 4H, the higher diamondoid derivatives can function as a cross-linker, in which case the higher diamondoid links two polymer chains.

Figure 4I:
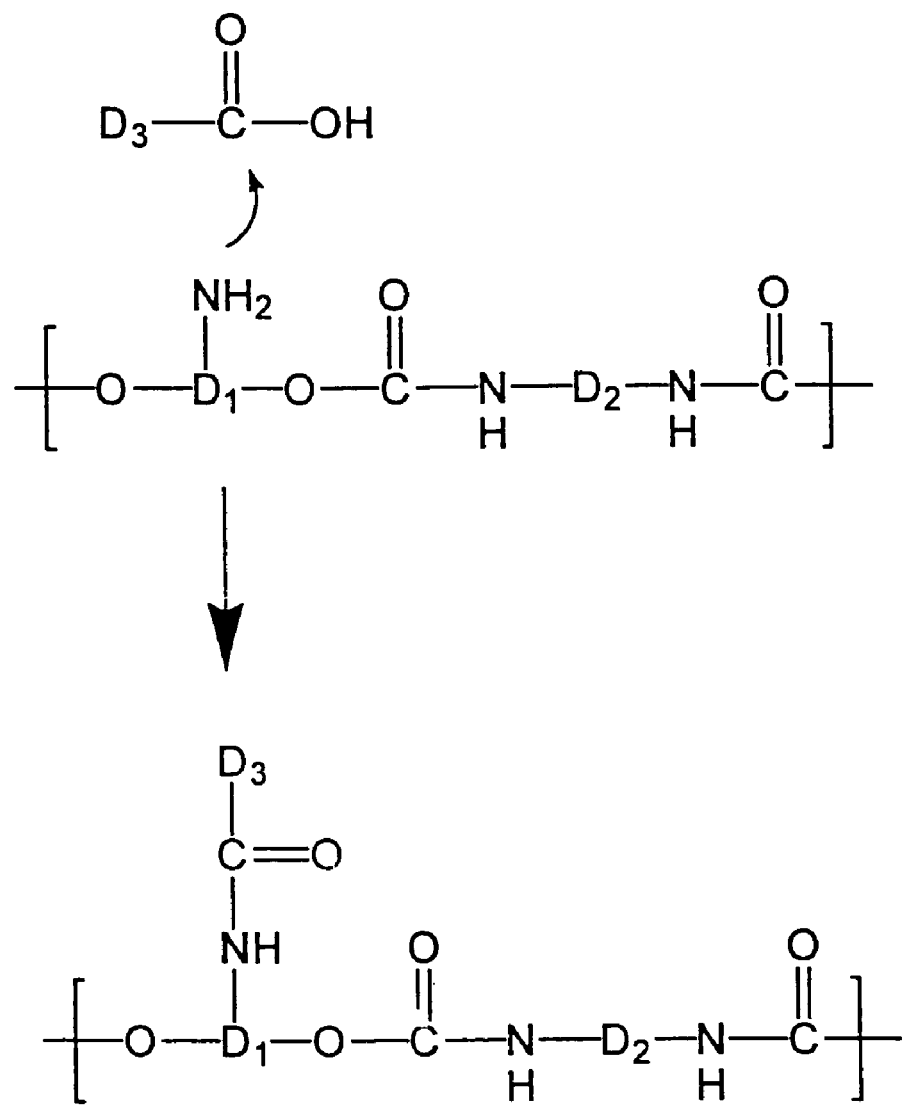
FIG. 4I is a table of representative polymerizable higher diamondoid derivatives and representative polymers they enable.

A range of polymerization reactions are depicted in FIG. 4I where prepresentative higher diamondoid derivatives are shown together with reaction routes to polymers.

Higher Diamondoid-Containing Polymers

As just described, the polymers contain higher diamondoids as recurring units. They may be present as part of the polymer backbone, as sidegroups or as branches off of the chain.

In one embodiment, the polymer comprises multiple copies of the same or different higher diamondoid covalently bonded to each other and preferably attached through a linker. Such resulting polymer may be a homopolymer or in another aspect, a co-polymer. Accordingly, one such polymer represented by formula

(D)$_q$-L wherein

D is a higher diamondoid;

L is a linker having at least two complementary functional groups wherein at least one functional group is covalently bonded to the higher diamondoid; and q is an integer from 2 to 1000 or higher.

In yet another embodiment, the polymer comprises multiple copies of the same or different higher diamondoid attached to multiple copies of the same or different linker, these polymers also may be homopolymers or heteropolymers. Such a polymer is represented by formula:

D-L(-D-L)$_r$-D wherein each D is independently a higher diamondoid group;

L is a linker; and r is an integer from 1 to 1,000,000 and preferably from 1 to 1000.

In yet another aspect of this invention the higher diamond derivatives can be covalently bonded to each other through their derivatizing moieties (R) without the use of a linker, accordingly such polymers formed can be represented by

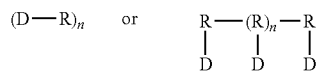

where each D is independently selected from a higher diamondoid group, R is a derivatizing group and n is an integer from 2 to 1000 or higher.

In another embodiment, the higher diamondoid derivative contains a single polymerizable moiety and is formed into a dimeric material by reaction with a single linker. For example, a dimeric diamondoid structure of the formula:

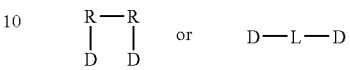

which could be prepared by reaction of a carboxyl containing higher diamondoid derivative with ethylene diamine to provide e.g. [higher diamondoid]-C(O)NHCH$_2$CH$_2$NHC(O)-[higher diamondoid]. In another aspect, there are multiple higher diamondoids attached to a common linker or backbone.

The variety of polymers formed from the polymerizable higher diamondoids derivatices is shown in FIG. 4 which illustrate representative types and classes of polymers. In these formulae, D is a higher diamoindoid derivative and CP, etc. are copolymerizable materials.

Many of these polymers include a linking group which can react with two or more diamondoid derivatives. Such linking moieties can for example, be derived from diacids, dicarboxylic acids, disulfonyl halides, dialdehydes, diketones, dihalides, diisocyanates, diamines, diols, dithiols, and the like or mixtures of carboxylic acids, sulfonylhalides, aldehydes, ketones, diols and the like.

A preferred linker L, may be represented by the following formula:

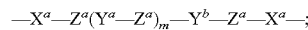

—X$^a$—Z$^a$(Y$^a$—Z$^a$)$_m$—Y$^b$—Z$^a$—X$^a$—;

in which m is an integer from 0 to 50, preferably from 0 to 20, X$^a$ at each separate occurrence is selected from the group consisting of —O—, —S—, —NR$^{20}$—, —C(O)—, —C(O)O—, —C(O)NR$^{20}$—, —C(S), —C(S)O—, —C(S)NR$^{20}$— or a covalent bond, wherein the R$^{20}$s, at each separate occurrence, are independently defined as selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic; Z$^a$ is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond; Y$^a$ and Y$^b$ at each separate occurrence are selected from the group consisting of —C(O)NR$^{21}$—, —NR$^{21}$C(O)—, —NR$^{21}$C(O)NR$^{21}$—, —C(=NR$^{21}$)—NR$^{21}$—, —NR$^{21}$C(=NR$^{21}$)—, —NR$^{21}$—C(O)—O—, —N=C(X$^a$)—NR$^{21}$—, —P(O)(OR$^{21}$)—O—, —S(O)$_n$CR$^{21}$R$^{22}$—, —S(O)$_n$—NR$^{21}$—, —S—S— and a covalent bond, where n is 0, 1, and 2; and wherein R$^{21}$ and R$^{22}$ at each separate occurrence are independently defined as selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic; provided that at least one of X$^a$, Y$^a$, Y$^b$ or Z$^a$ is not a covalent bond.

Some of the preferred linkers can be derived from mono or polyamide, mono or polyimide, mono or polyurethane, mono or polyacetal, mono or polyethylene, mono or polyisobutenylene, mono or polyacrylonitril, mono or polycarbonate, mono or poly(vinyl chloride), mono or polystyrene, mono or polyvinyl acetal, mono or poly(methyl metharcylate), mono or poly(vinylidene chloride), mono or polyisoprene, mono or polyoxymethylene, mono or polyaspartimides, polyamide-imides and the like.

Figure 5A:
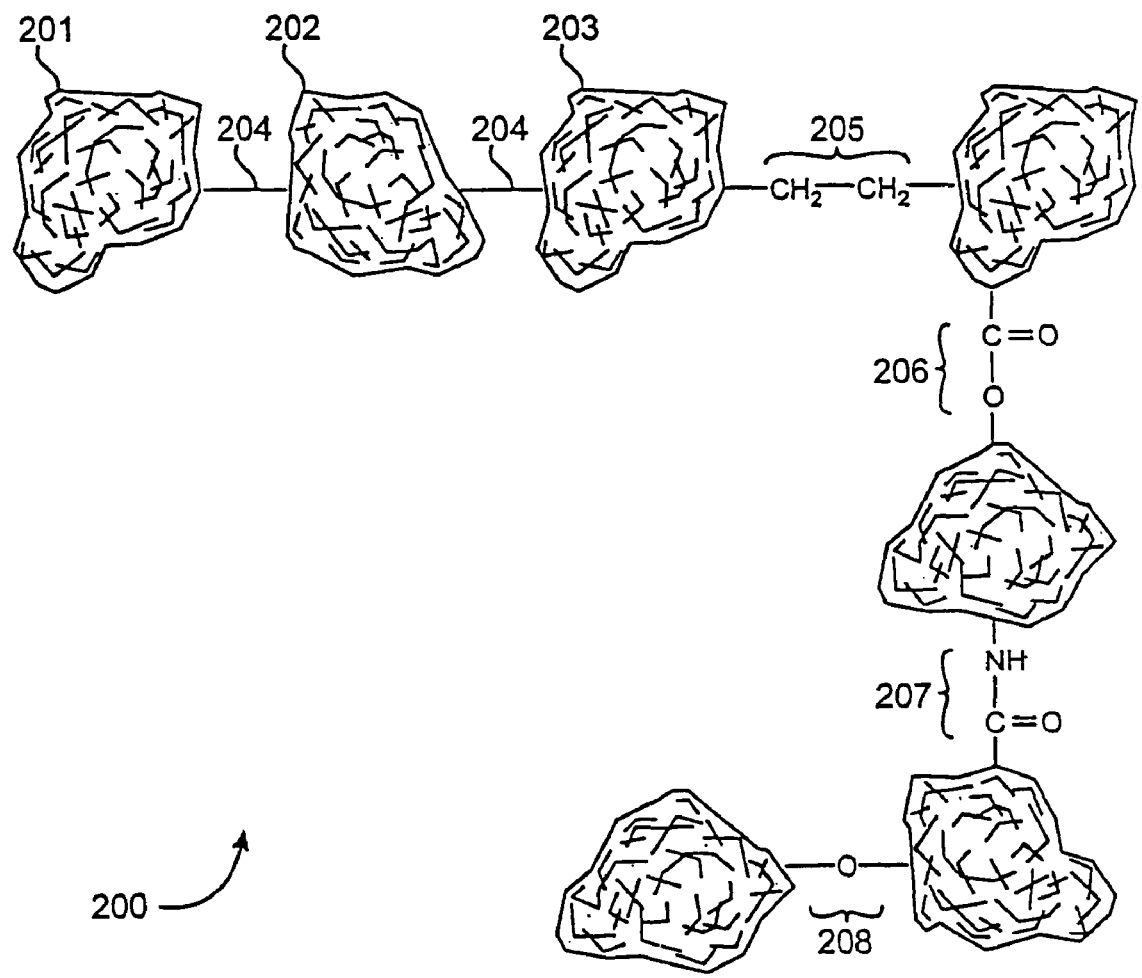
FIGS. 5A-5C illustrate exemplary polymer materials that contain higher diamondoids as recurring units.
Figure 5B:
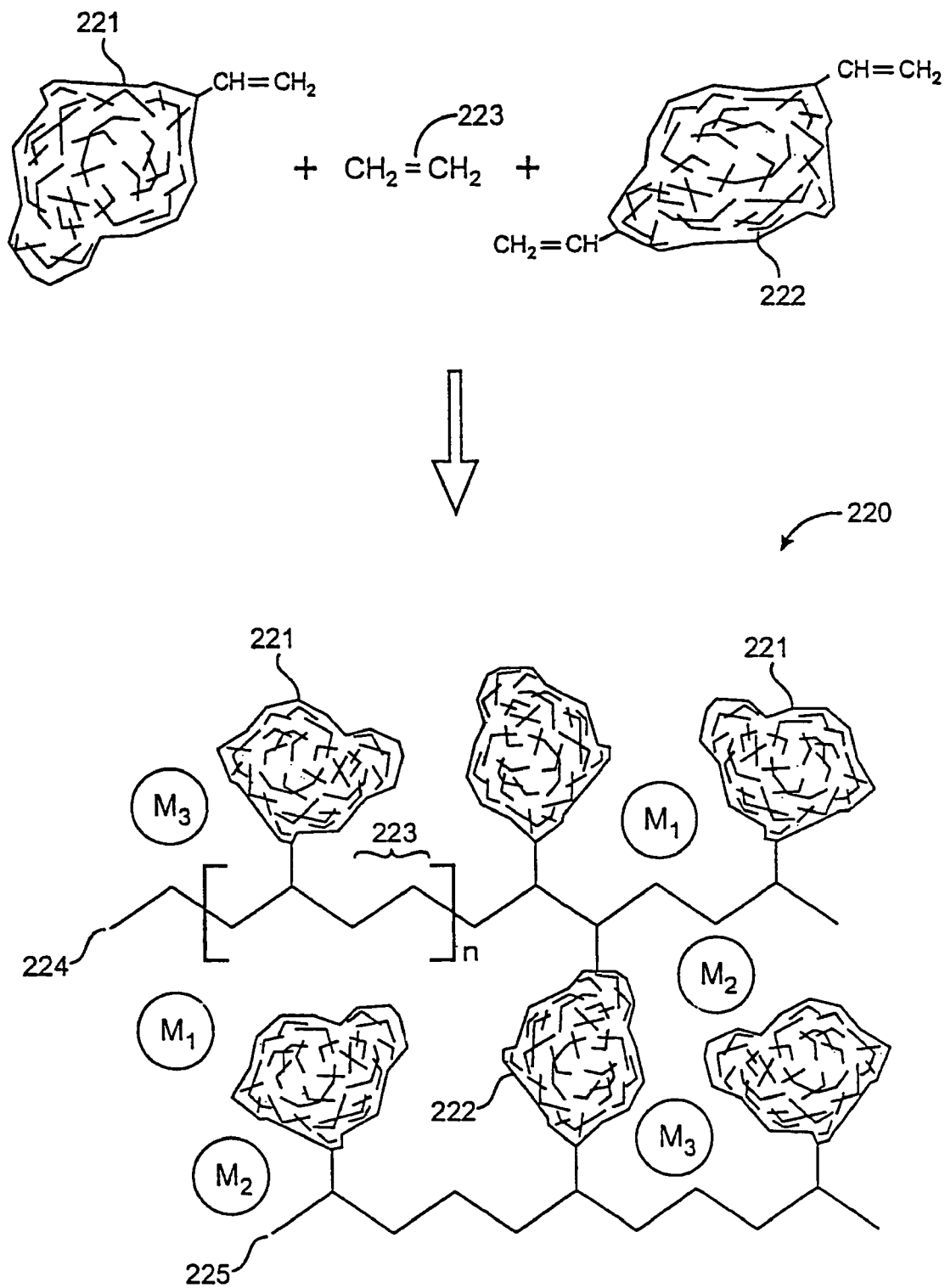
Figure 5C:
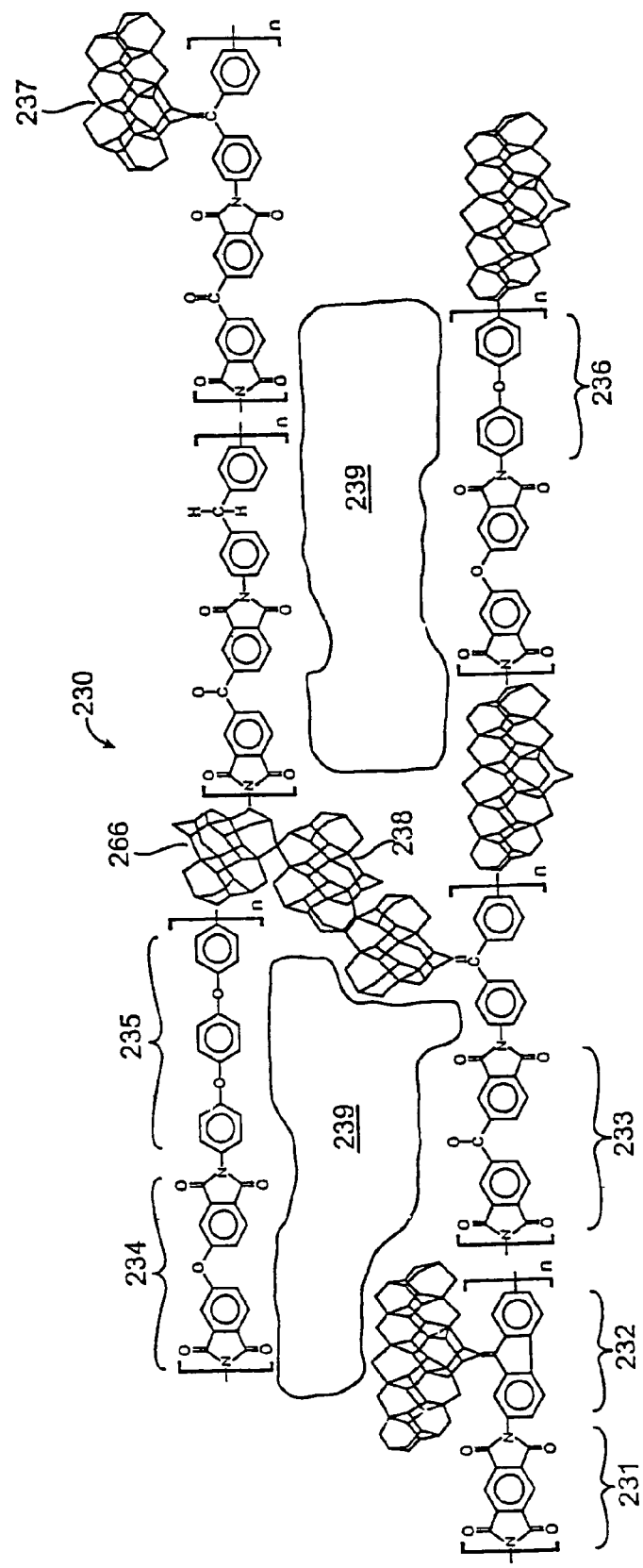
Figure 5D:
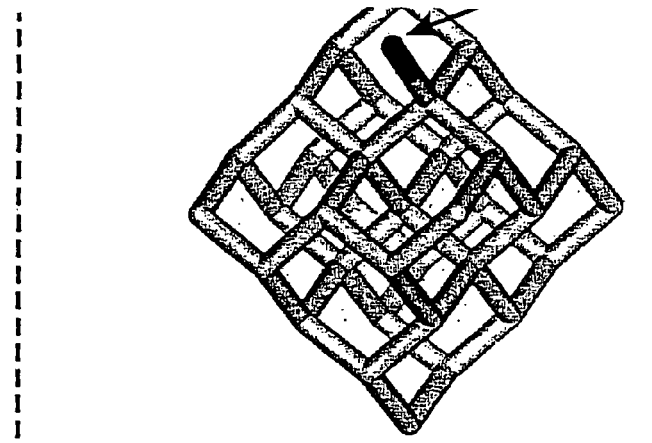
FIGS. 5D-5F illustrate the variety of carbon attachment sites on a decamantane molecule and how attachments to different sites in a polymer may result in cross-linked materials of varying rigidity.

Exemplary diamondoid-containing polymers are illustrated schematically in FIGS. 5A-5C. Referring to FIG. 5A, a diamondoid-containing polymer is shown generally at 200, where the polymer comprises diamondoid monomers 201, 202, 203 linked through carbon-to-carbon covalent bonds 204. The diamondoid monomers 201, 202, 203 may comprise any member of the higher diamondoid series tetramantane through undecamantane. The covalent linkage 204 comprises a bond between two carbon atoms where each of carbon atoms of the bond are members of the two adjacent diamondoids. Stated another way, two diamondoids in the polymeric chain are directly linked such that there are no intervening carbon atoms that are not part of a diamondoid nucleus (or part of an adamantane subunit).

Alternatively, two adjacent diamondoids may be covalently linked through carbon atoms that are not members (part of the carbon nucleus) of either of the two diamondoids. Such a covalent linkage is shown schematically in FIG. 5A at reference numeral 205. As discussed above, adjacent diamondoids may be covalently connected through, for example, an ester linkages 206, an amide linkages 207, and an ether linkage is 208.

In an alternative embodiment, a diamondoid-containing polymer shown generally at 220 in FIG. 5B comprises a copolymer formed from the monomers ethylene and a higher diamondoid having at least one ethylene substituent. The diamondoid monomer shown at 221 contains one substituent ethylene group. The diamondoid monomer shown at 222 contains two ethylene substituents, and could have more than two substituents. Either or both of these diamondoids may be copolymerized with ethylene 223 itself, as a third monomer participating in the reaction, to form the co-polymer 220 or subunits thereof. Because the diamondoid monomer 222 has two substituent polymerizable moieties attached to it, this particular monomer is capable of cross-linking chains 224 and chain 225 together. Such a cross-linking reaction is capable of producing polymers having properties other than those of the polymer depicted in FIG. 5A, since for the FIG. 5A polymer the diamondoid nucleus are positioned within the main chain. A consequence of the structures formed in FIGS. 5A and 5B is that it is possible to incorporate metallic elements, particles, and inclusions (illustrated as M1 to M3) by inserting them into the interstices of folded and cross-linked polymeric chains. The relative ratios of the monofunctional diamondoid monomer, the difunctional diamondoid monomer, and the ethylene monomer in the exemplary polymer of FIG. 5B may of course be adjusted to produce the desired properties with regard to stiffness, compactness, and ease of processing.

The exemplary polyimide-diamondoid polymer shown generally at 230 in FIG. 5C contains segments of polyimide chains derived from representative groups selected to illustrate certain relationships between structure and properties, in particular, how the properties of the exemplary polymer relate to the processing it has undergone. The dianhydride PMDA (pyromellitic dianhydride) shown at 231 and the diamine diaminofluorenone 232 are introduced into the chain for rigidity. The dianhydride BTDA (benzophenonetetracarboxylic dianhydride) shown at 233 provides the capability of further reaction at the carboxyl site, possibly for crosslinking purposes, and/or for the potential inclusion of metallic moieties into the material. The dianhydride oxydiphthalic dianhydride (ODPA) shown at 234, and the diamines oxydianiline (ODA) at 235 and bisaminophenoxybenzene at 236 may be introduced for chain flexibility and ease of processing of the material. Additionally, fluorinated dianhydrides such as 6FDA (not shown) may be introduced to lower the overall dielectric constant of the material.

The diamondoid components of the exemplary polymer illustrated schematically in FIG. 5C comprise a pentamantane diamondoid at 236, which is positioned in the main chain of the polymer, and an octamantane diamondoid at 237, which comprises a side group of the diamondoid-polyimide polymer at a position of a diamine (in this exemplary case, diaminobenzophenone) component. A diamondoid component 238 may be used as a cross-linking agent to connect two adjacent chains, through covalent linkages, or diamondoid component 238 may be passively present as an unfunctionalized "space filler" wherein it serves to separate main polymeric chains simply by steric hindrance. Folding of the main polymeric chains, particularly when diamondoid "fillers" 238 are present, may create voids 239, which may serve to reduce the overall dielectric constant of the material, since the dielectric constant of air (if it is the gas within the void), is one.

As shown in FIG. 1B the diamond nanocrystallites (higher diamondoids) that may be incorporated into a diamondoid-containing material in general, and into polymeric materials in particular, have a variety of well-defined molecular structures, and thus they may be attached to each other, attached to a main polymer chain, used as cross-linking agents, etc., in a great variety of ways.

Figure 5E:
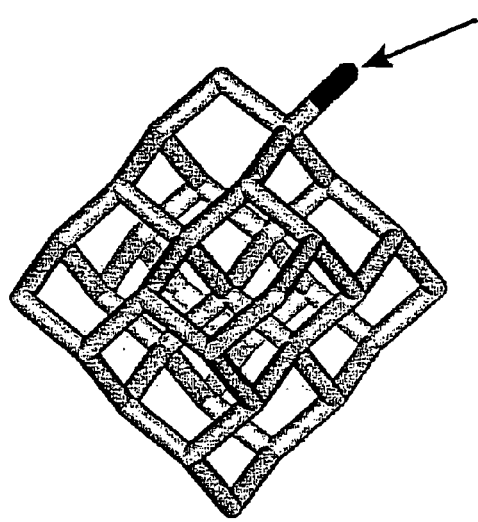
Figure 5F:
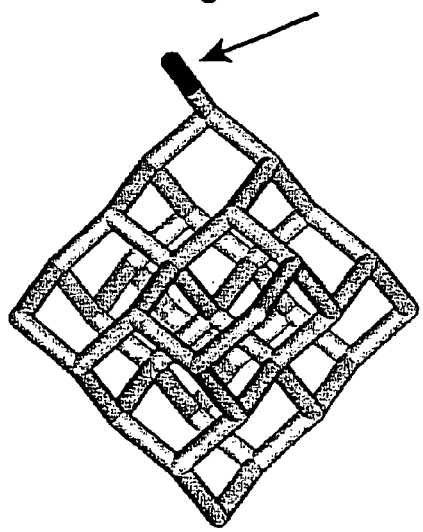

The molecular sites and the geometries of the attachments of a higher diamondoid to another diamondoid, and to a polymer chain, will also affect the properties of resulting materials. For example, the interconnection of higher diamondoid units through tertiary "bridge-head" carbons, as illustrated in FIG. 5E, will result in stronger, more rigid materials than those which result from interconnection through secondary carbons, as in FIG. 5F. Furthermore, attachment through tertiary carbons that are themselves bonded to the highest number of quaternary carbons in a higher diamondoid (nanocrystallite) will provide the strongest, most rigid materials, as in FIG. 5D.

There are other properties of higher diamondoids that may be exploited to design new materials with desirable properties. Higher diamondoids display classical diamond crystal faces such as the (111), (110), and (100) planes. These higher diamondoids may be oriented in materials such as polymers so that the resulting diamond nanocrystallites may have co-planer diamond faces. The diamondoids with chiral stcructure, may be used to fabricate the exemplary chiral polymers illustrated in FIGS. 5G-5H. The kinds of chiral polymers have potential uses in photonics, and for the integration of photonic and electronic devices.

Utility

The polymers of the present invention can take a variety of forms and can find a variety of applications. Such materials include composite matrix resins, structural adhesives and surface films that are used for aerospace structural applications. Furthermore, coating layers or moldings with excellent optical, electrical or electronic and mechanical properties are produced for use in optical fibers, photoresist compositions, conducting materials, paint compositions and printing inks.

In addition, higher diamondoid-containing polymers will have high thermal stability making them suitable for use in environments requiring such stability including for example, devices such as semiconductors, coatings for refractory troughs or other high temperature applications. Higher diamondoid containing polymers will also have improved wear resistance coatings which can could mean improved protection and extended lifetimes for metal or plastic tools, autoparts etc.

EXAMPLES

As used herein and in the Figures, the following abbreviations have the following meanings. Any abbreviation not defined below has its generally accepted meaning.

| | |
|---|---|
| API = | American Petroleum Institute |
| atm eqv = | atmospheric equivalent |
| btms = | bottoms |
| DMAc = | N,N-dimethylacetamide |
| NMP = | N-methyl-2-pyrrolidone |
| DMSO = | dimethylsulfoxide |
| DMF = | dimethylformamide |
| EOR Traps = | end of run traps |
| fid = | flame ionization detector |
| g = | grams |
| GC = | gas chromatography |
| GC/MS = | gas chromatography/mass spectroscopy |
| h = | hour |
| HPLC = | high performance liquid chromatography |
| HYD RDG = | hydrometer reading |
| L = | liter |
| min = | minute |
| mL = | milliliters |
| mmol = | millimols |
| N = | normal |
| pA = | pico amps |
| PEG = | polyethylene glycol |
| ppb = | parts per billion |
| ppm = | parts per million |
| RI = | refractive index |
| SIM DIS = | simulated distillation |
| ST = | start |
| TIC = | total ion current |
| TLC = | thin layer chromatography |
| THF = | tetrahydrofuran |
| UV = | ultraviolet |
| VLT = | vapor line temperature |
| VOL PCT = | volume percent |
| v/v = | volume to volume |
| wt = | weight |
| WT PCT = | weight percent |

Introduction

The steps used in the various Examples are shown schematically in FIG. 7.

Example 1 describes a most universal route for isolating higher diamondoids components which can be applied to all feedstocks. This process uses HPLC (Step 7, FIG. 7) as its final isolation step.

Example 2 describes a variation of the process of Example 1 in which preparative gas chromatography (Step 7', FIG. 7) replaces HPLC as the final isolation step.

Example 3 describes a variation of the process of Example 1 in which the pyrolysis (Step 5, FIG. 7) is omitted. As shown optionally in FIG. 7, the liquid chromatographic step (Step 6, FIG. 7) is also omitted. These variations generally have applicability only with selected feedstocks and generally when tetramantanes, pentamantane and cyclohexamantane are the target higher diamondoids.

Example 4 describes yet another process variation in which the final products of Examples 1 and 3 are subjected to preparative gas chromatography purification to give further separation of higher diamondoid components (Step 8, FIG. 7).

Example 5 describes the Bromination of a mixed tetramantane-alkyltetramantane feed and shows the preparation of a variety of mono- and polybromonated tetramantane derivatives and intermediates.

Examples 6-45 describe methods that could be used to prepare higher diamondoid derivatives and intermediates.

Examples 46-61 describe methods that could be used to prepare higher diamondoid-containing polymers.

Examples 62-72 describe methods that could be used to prepare higher diamondoid derivatives and intermediates.

Examples 73-79 describes additional methods that could be used to prepare higher diamondoid-containing polymers.

It will be understood that it is possible to vary the order of the various distillation, chromatography and pyrolysis steps, although the order set forth in Example 1 has given the best results.

Example 1

This Example has seven steps (see Flow Chart in FIG. 7).
Step 1. Feedstock selection
Step 2. GCMC assay development
Step 3. Feedstock atmospheric distillation
Step 4. Vacuum fractionation of atmospheric distillation residue
Step 5. Pyrolysis of isolated fractions
Step 6. Removal of aromatic and polar nondiamondoid components
Step 7. Multi-column HPLC isolation of higher diamondoids
 a) First column of first selectivity to provide fractions enriched in specific higher diamondoids.
 b) Second column of different selectivity to provide isolated higher diamondoids.

This example is written in terms of isolating several hexamantanes.

Step 1—Feedstock Selection

Figure 6:
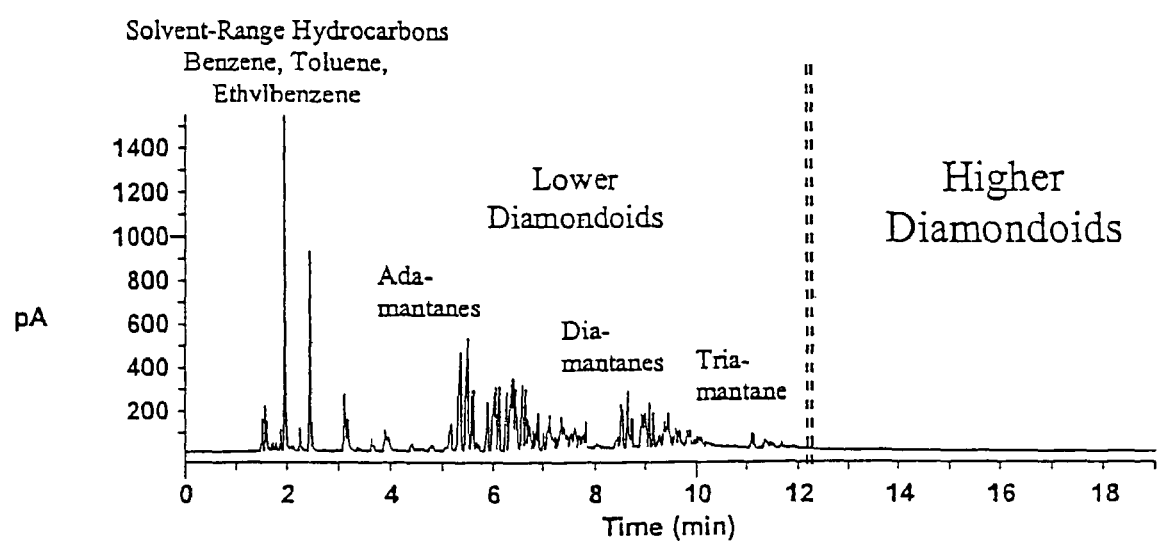
FIG. 6 illustrates the gas chromatogram of a gas condensate feedstock; one of the original feedstocks used in the Examples (Feedstock A).

Suitable starting materials were obtained. These materials included a gas condensate, Feedstock A (FIG. 6), and a gas condensate containing petroleum components, Feedstock B. Although other condensates, petroleums, or refinery cuts and products could have been used, these two materials were chosen due to their high diamondoid concentration, approximately 0.3 weight percent higher diamondoids, as determined by GC and GC/MS. Both feedstocks were light colored and had API gravities between 19 and 20° API.

Step 2—GC/MS Assay Development

Feedstock A was analyzed using gas chromatography/mass spectrometry to confirm the presence of target higher diamondoids and to provide gas chromatographic retention times for these target materials. This information is used to track individual target higher diamondoids through subsequent isolation procedures. FIG. 8A is a table that lists typical GC/MS assay information for the hexamantanes (GC retention times, mass spectral molecular ion (M+) and base peak). This table (FIG. 8A) also contains similar GC/MS assay information for other higher diamondoids. While relative G(retention times are approximately constant, non-referenced GC retentions vary with time. It is recommended that GC/MS assay values be routinely updated especially when GC retention time drift is detected.

Step 3—Feedstock Atmospheric Distillation

A sample of Feedstock B was distilled into a number of fractions based on boiling points to separate the lower boiling point components (nondiamondoids and lower diamondoids)

and for further concentration and enrichment of particular higher diamondoids in various fractions. The yields of atmospheric distillate fractions of two separate samples of Feedstock B are shown in Table 3, below and are contrasted to simulated distillation yields. As seen from Table 3, the simulated distillation data is in agreement with the actual distillation data. The simulated distillation data were used to plan subsequent distillation processes.

TABLE 3

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

TABLE 3-continued

Yields of Atmospheric Distillation Fractions from Two Separate Runs of Feedstock B

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Step 4—Fractionation of Atmospheric Distillation Residue by Vacuum Distillation

Figure 9:
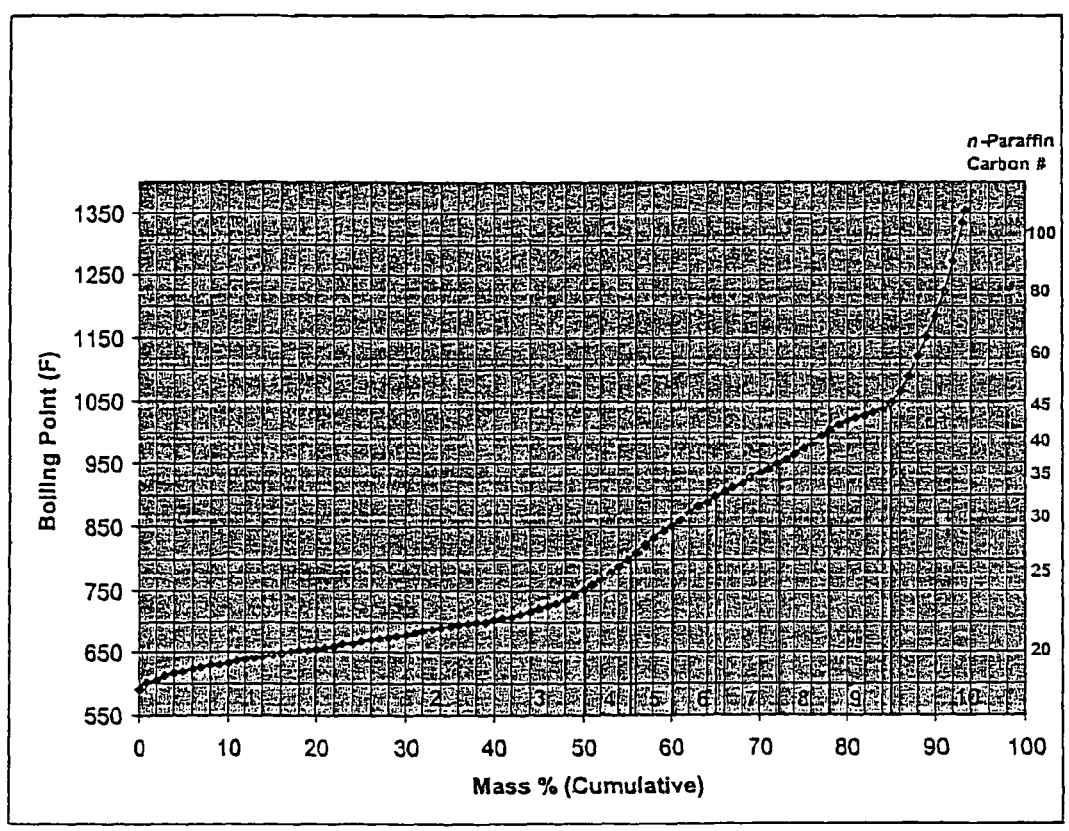
FIG. 9 illustrates a high temperature simulated distillation profile of Feedstock B using the atmospheric distillation 650° F.+bottoms as feedstock. This figure also illustrates the targeted cut points (1-10) we used for higher diamondoid isolations.

The resulting Feedstock B atmospheric residium from Step 3 (comprising 2-4 weight percent of the original feedstock) was distilled into fractions containing higher diamondoids as shown in FIGS. 9 and 10). The feed to this high temperature distillation process was the atmospheric 650° F.+bottoms. Complete Feedstock B distillation reports are given in Tables 4A and 4B. Tables 5A and 5B illustrate the distillation reports for Feedstock B 650° F.+distillation bottoms.

TABLE 4A

Distillation Report for Feedstock B

Feedstock B
Column Used: Clean 9" × 1.4" Protruded Packed

| CUT | VAPOR TEMP ST - END | | DISTILLATION RECORD | | | | NORMALIZED | | ACTUAL | |
|---|---|---|---|---|---|---|---|---|---|---|
| | | | WEIGHT G | VOLUME ml @ 60° F. | API 60/60 | DENSITY @ 60° F. | WT PCT | VOL PCT | WT PCT | VOL PCT |
| 1 | 226 | − 349 | 67.0 | 80 | 38.0 | 0.8348 | 7.61 | 8.54 | 7.39 | 8.26 |
| 2 | 349 | − 491 | 507.7 | 554 | 22.8 | 0.9170 | 57.65 | 59.12 | 55.98 | 57.23 |
| 3 | 491 | − 643 | 269.6 | 268 | 9.1 | 1.0064 | 30.62 | 28.60 | 29.73 | 27.69 |
| COL HOLDUP | | | 0.2 | 0 | 6.6 | 1.0246 | 0.02 | 0.00 | 0.02 | 0.00 |
| BTMS 643 + | | | 36.1 | 35 | 6.6 | 1.0246 | 4.09 | 3.74 | 3.98 | 3.62 |
| EOR TRAPS | | | 0.0 | 0 | | | 0.00 | 0.00 | | 0.00 |
| TOTALS | | | 880.6 | 937 | | | 100.00 | 100.00 | 97.09 | 96.80 |
| LOSS | | | 26.4 | 31 | | | | | 2.91 | 3.20 |
| FEED | | | 907.0 | 968 | 19.5 | 0.9371 | | | 100.00 | 100.00 |
| BACK CALCULATED API AND DENSITY | | | | | 19.1 | 0.9396 | | | | |

TABLE 4B

Distillation Report for Feedstock B

Feedstock B
Column Used: Clean 9" × 1.4" Protruded Packed

| TEMPERATURE DEGREES F. | | | | | | | | API GRAVITIES | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | | START OVERHEAD | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |

TABLE 4B-continued

Distillation Report for Feedstock B

Cut 2 looks Milky, White crystals form in Run Down Line. Heat Lamp applied to drip tube.
Cool to transfer btms to smaller flask.

| | | | | | | | | | | |
|---|---|---|---|---|---|---|---|---|---|---|
| 208 | 437.7 | 323 | 10.000 | 3:1 | | | START OVERHEAD | | | |
| 378 | 643.3 | 550 | 10.000 | 3:1 | 3 | 268 | 269.6 | 9.9 | 75.0 | 9.1 |
| | | | | Shutdown due to dry pot | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 5A

Vacuum Distillation Report for Feedstock B

Feedstock B - Atmospheric distillation resid 650° F. + bottoms
Column Used: Sarnia Hi Vac

| TEMPERATURE DEGREES F. | | | | | | | | API GRAVITIES | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | VOLUME ml 60° F. | WEIGHT G | HYD RDG | TEMP ° F. | 60° F. |
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | | MID AND | END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | −5 | 14.6 | | | |

TABLE 5B

Distillation Report for Feedstock B-btms

Feedstock B - Atmospheric distillation resid 650° F. + bottoms
Column Used: Sarnia HiVac

| CUT | VAPOR TEMP ST - END | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|
| 1 | 601 | – 656 | 666.4 | 639 | 4.1 | 1.0435 | 20.12 | 19.38 | 20.03 | 19.40 |
| 2 | 656 | – 702 | 666.9 | 646 | 5.6 | 1.0321 | 20.14 | 19.59 | 20.05 | 19.62 |
| 3 | 702 | – 752 | 334.3 | 330 | 8.3 | 1.0122 | 10.09 | 10.01 | 10.05 | 10.02 |

TABLE 5B-continued

| | | | | | | | | | | | |
|---|---|---|---|---|---|---|---|---|---|---|---|
| | Distillation Report for Feedstock B-btms |

| | | | | | | | | | | | |
|---|---|---|---|---|---|---|---|---|---|---|---|
| 4 | 752 | – | 800 | 167.7 | 173 | 14.5 | 0.9692 | 5.06 | 5.25 | 5.04 | 5.25 |
| 5 | 800 | – | 852 | 167.3 | 181 | 21.7 | 0.9236 | 5.05 | 5.49 | 5.03 | 5.50 |
| 6 | 852 | – | 900 | 167.1 | 181 | 21.9 | 0.9224 | 5.05 | 5.49 | 5.02 | 5.50 |
| 7 | 900 | – | 950 | 238.4 | 257 | 21.2 | 0.9267 | 7.25 | 7.79 | 7.17 | 7.80 |
| 8 | 950 | – | 976 | 85.4 | 91 | 18.9 | 0.9408 | 2.58 | 2.76 | 2.57 | 2.76 |
| 9 | 976 | – | 1000 | 80.8 | 85 | 18.2 | 0.9452 | 2.44 | 2.58 | 2.43 | 2.58 |
| 10 | 1000 | – | 1026 | 93.8 | 98 | 16.9 | 0.9535 | 2.83 | 2.97 | 2.82 | 2.98 |
| COL HOLDUP | | | | 4.0 | 4 | 3.4 | 1.0489 | 0.12 | 0.12 | 0.12 | 0.12 |
| BTMS | 1026 | + | | 621.8 | 593 | 3.4 | 1.0489 | 18.78 | 17.98 | 18.69 | 18.01 |
| EOR TRAPS | | | | 17.8 | 20 | | | 0.54 | 0.61 | 0.54 | 0.61 |
| TOTALS | | | | 3311.7 | 3298 | | | 100.00 | 100.00 | 99.56 | 100.15 |
| LOSS | | | | 14.6 | –5 | | | | | 0.44 | –0.15 |
| FEED | | | | 3326.3 | 3293 | 8.6 | 1.0100 | | | 100.00 | 100.00 |
| BACK CALCULATED API & DENSITY | | | | | | 9.4 | 1.0039 | | | | |

TABLE 6

Elemental Composition of Feedstock B
Analyses on Feedstock B 650 + F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 6 illustrates the partial elemental composition of Feedstock B atmospheric distillation (650° F.) residue including some of the identified impurities. Table 6 displays the weight percent nitrogen, sulfur, nickel and vanadium in Feedstock B atmospheric distillation residue. Subsequent steps remove these materials.

Step 5—Pyrolysis of Isolated Fractions

Figure 11A:
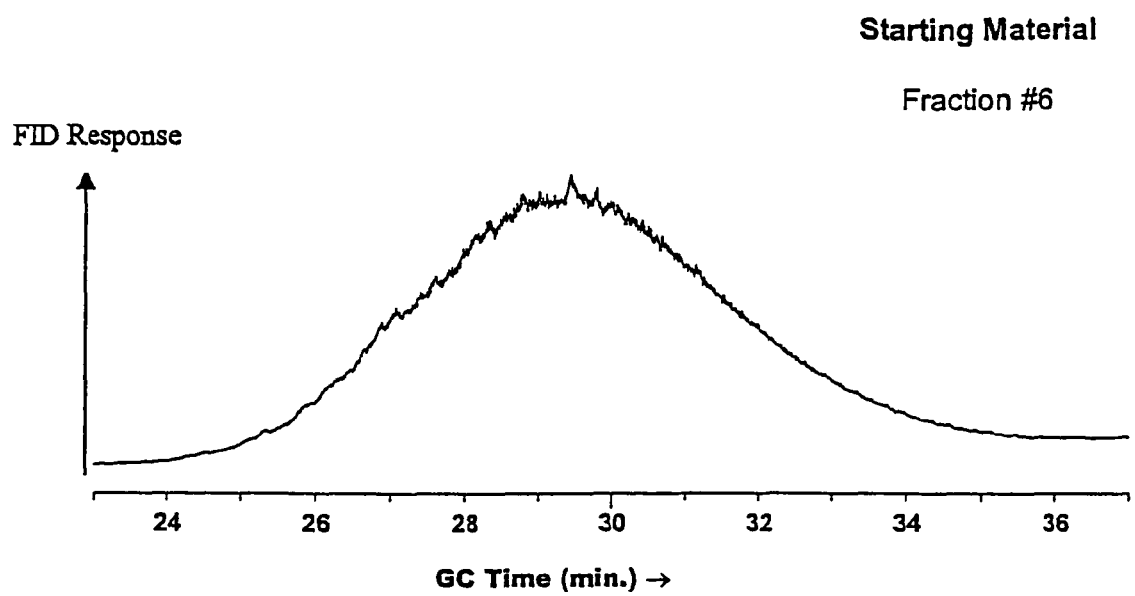
FIGS. 11A and 11B illustrate gas chromatograms (FID) of distillate fraction #6 (Table 5B) of Feedstock B 650° F.+distillation bottoms, and the resulting product of pyrolytic processing. These figures show that nondiamondoid components have been destroyed by the pyrolytic processing and that higher diamondoids especially hexamantanes have been concentrated and made available for isolation.
Figure 11B:
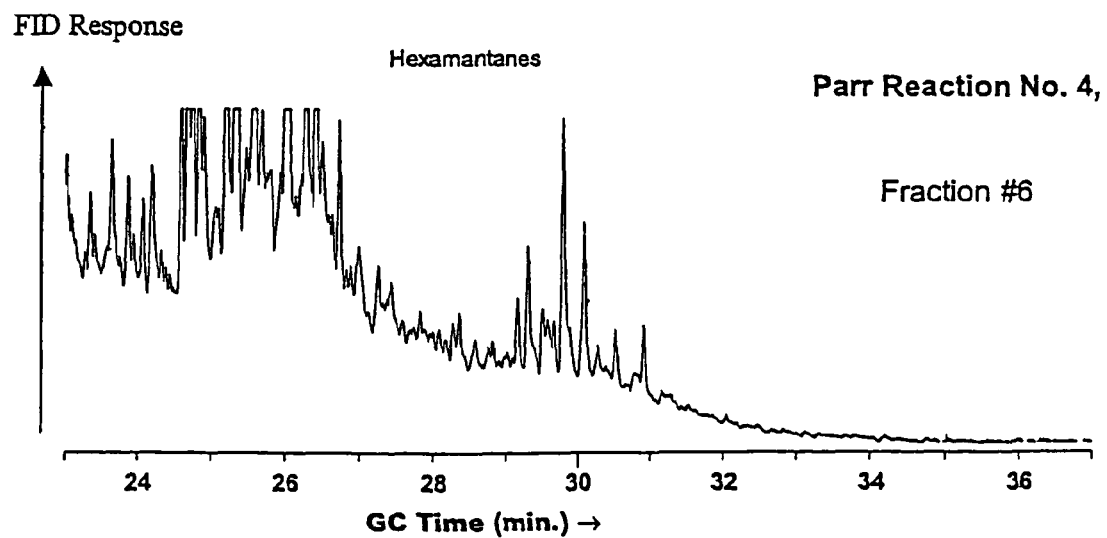

A high-temperature reactor was used to pyrolyze and degrade a portion of the nondiamondoid components in various distillation fractions obtained in Step 4 (FIG. 7) thereby enriching the diamondoids in the residue. The pyrolysis process was conducted at 450° C. for 19.5 hours. The gas chromatogram (FID) of fraction #6 (Table 5B) is shown in FIG. 11A. FIG. 11B is the chromatogram for the product of pyrolysis. A comparison of these chromatograms shows that pyrolysis has removed major nondiamondoid hydrocarbons and has significantly increased the higher diamondoid concentration, especially the hexamantanes. A 500 mL PARR® reactor from PARR Instrument Company, Moline, Ill. was used in this pyrolysis step.

Step 6—Removal of Aromatic and Polar Nondiamondoid Components

The pyrolysate produced in Step 5 was passed through a silica-gel gravity chromatography column (using cyclohexane elution solvent) to remove polar compounds and asphaltenes (Step 6, FIG. 7). The use of a silver nitrate impregnated silica gel (10 weight percent $AgNO_3$) provides cleaner diamondoid-containing fractions by removing the free aromatic and polar components. While it is not necessary to use this chromatographic aromatic separation method, it facilitates subsequent steps.

Step 7—Multi-Column HPLC Isolation of Higher Diamondoids

An excellent method for isolating high-purity higher diamondoids uses two or more HPLC columns of different selectivities in succession.

The first HPLC system consisted of two Whatman M20 10/50 ODS columns operated in series using acetone as mobile phase at 5.00 mL/min. A series of HPLC fractions were taken (see FIG. 12A). Fractions 36 and 37 were combined and taken for further purification on a second HPLC system. This combined fraction (36 and 37) contained hexamantanes #7, #11 and #13. (FIG. 12A).

Further purification of this combined ODS HPLC fraction was achieved using a Hypercarb stationary phase HPLC column having a different selectivity in the separation of various hexamantanes than the ODS column discussed above. FIG. 12B shows elution times of the individual hexamantanes on the Hypercarb HPLC column (with acetone as a mobile phase).

Figure 12A:
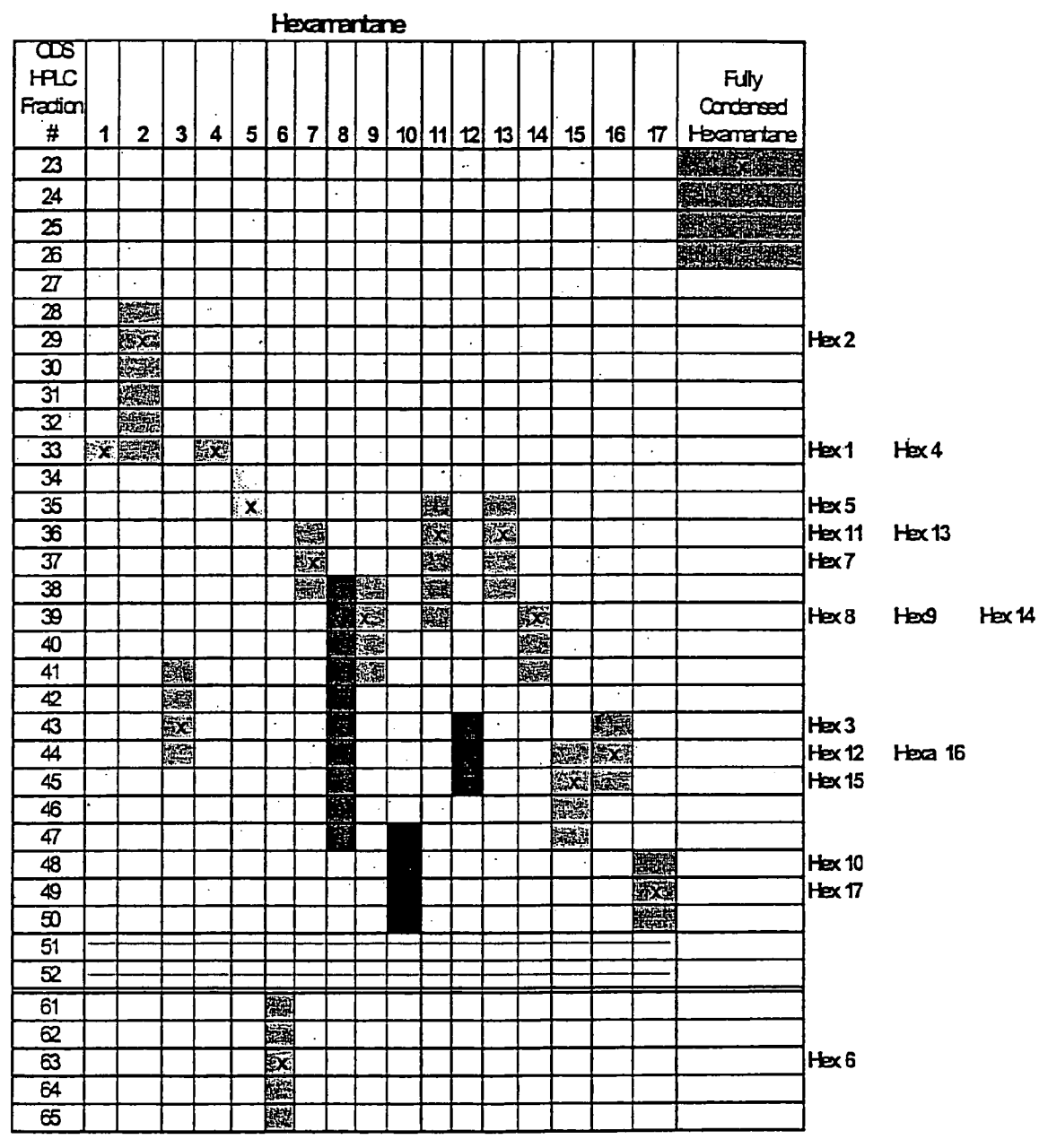

The differences in elution times and elution order of hexamantanes on ODS and Hypercarb HPLC columns are seen by comparing these two FIGS. 12A and 12B. For example, Hexamantanes #11 and #13 elute together on the ODS HPLC system (FIG. 12A) but in separate fractions (fractions 32 and 27, respectively) on the Hypercarb system (FIG. 12B).

Figure 13A:
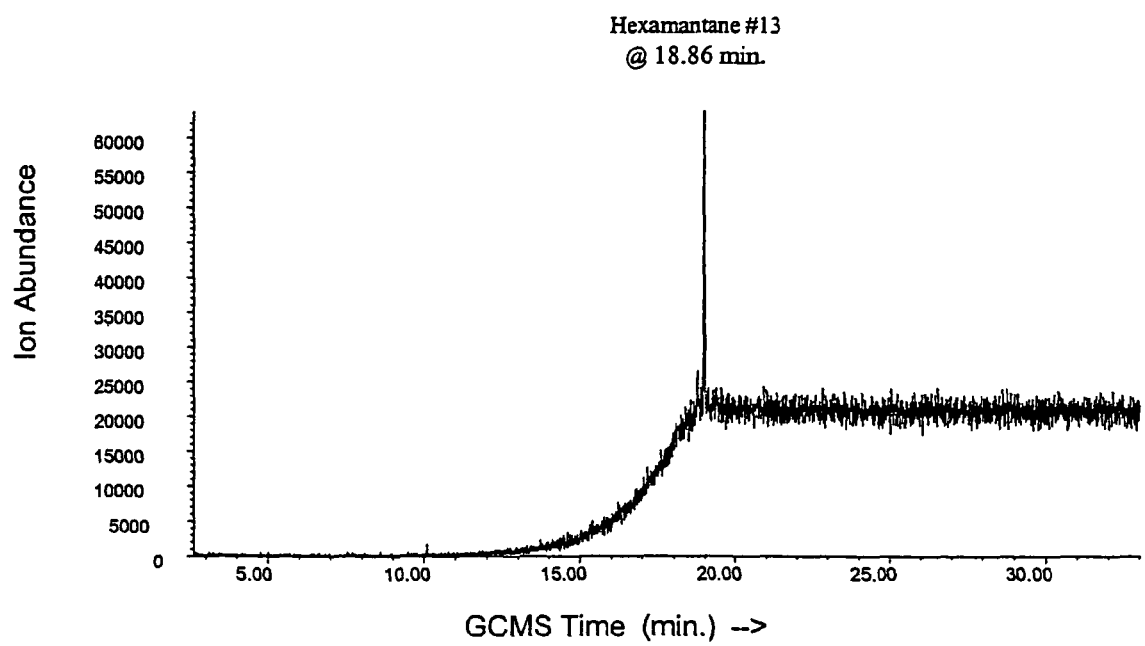
FIGS. 13A and 13B illustrate GC/MS total ion chromatogram (TIC) and mass spectrum of hexamantane #13 isolated using two different HPLC columns as shown in Example 1.
Figure 13B:
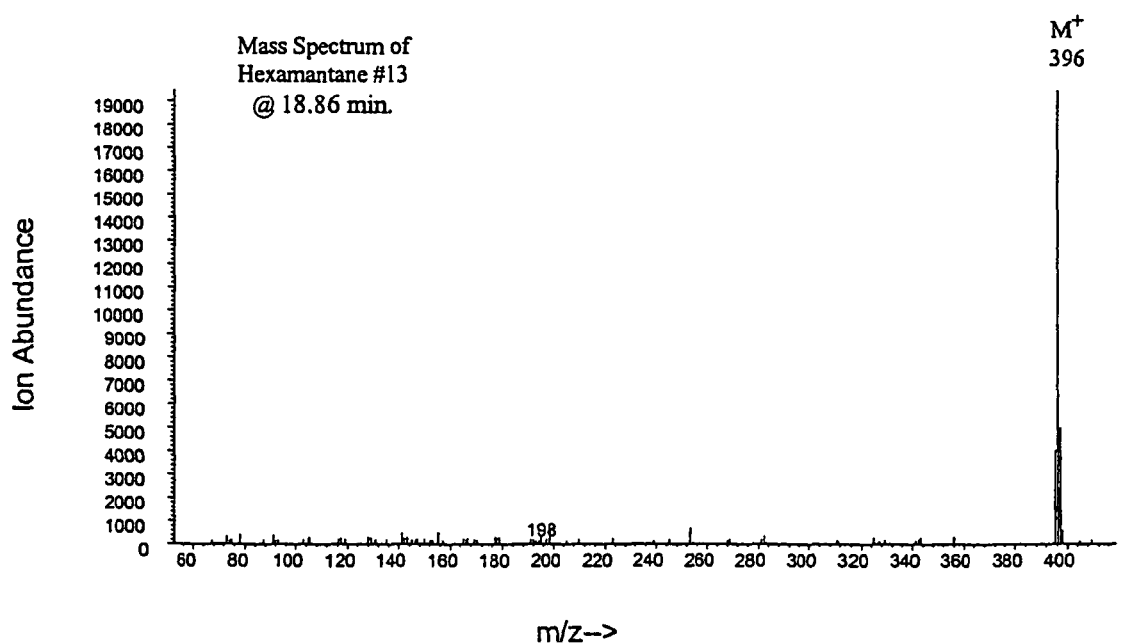

The different elution orders and times of selected higher diamondoids on these two systems can be used to separate co-eluting higher diamondoids. It can also be used to remove impurities. Using this method on combined ODS HPLC fractions 36 & 37, appropriate Hypercarb HPLC fractions were taken thus providing high-purity hexamantane #13 (FIGS. 13A and 13B). Other ODS HPLC fractions and Hypercarb HPLC cut points could be used to isolate the remaining hexamantanes. This isolation strategy is also applicable to the other higher diamondoids although elution solvent compositions can vary.

The ODS and Hypercarb columns can also be used in reverse order for these isolations. By using similar methodology as above, i.e. fractionating hexamantane-containing ODS fractions using the Hypercarb or other suitable column and collecting at corresponding elution times can lead to the isolation of the remaining hexamantanes in high purity. This is also true of the other higher diamondoids from tetramantanes to undecamantanes, including substituted forms.

Example 2

Steps 1, 2, 3, 4, 5 and 6 of Example 1 were repeated (FIG. 7). The following variation of Step 7 was then carried out.

Figure 14A:
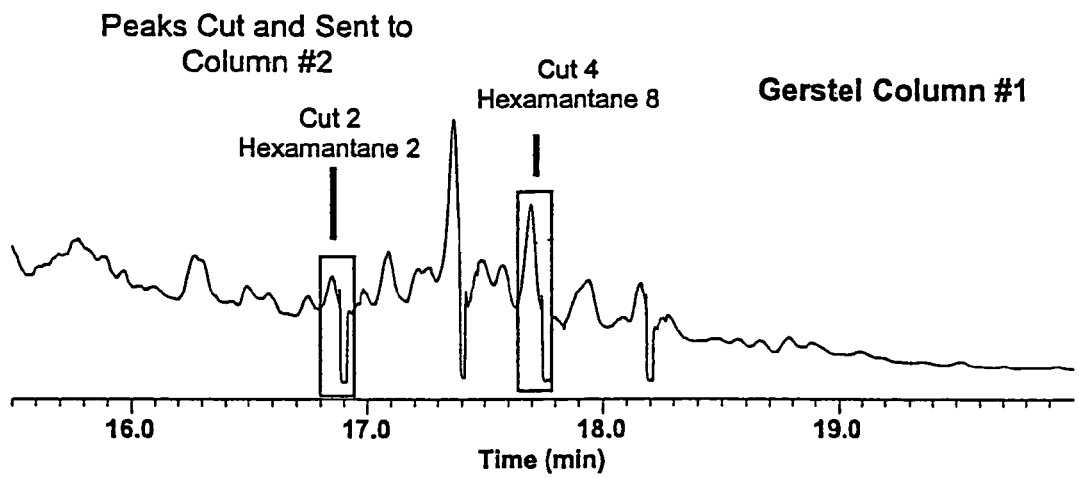
FIGS. 14A and 14B illustrate the preparative capillary gas chromatographic data for hexamantane isolations carried out in Example 2.

Step 7':

A two-column preparative capillary gas chromatograph was used to isolate hexamantanes from the product of Example 1, Step 6. The cut times for the hexamantanes were set for the first preparative capillary the GC column, methyl silicone DB-1 equivalent, using the retention times and patterns from GC/MS assay (Example 1, Step 2). The results are shown in FIG. 14A, two cuts identified as "peaks cut and sent to column 2", were taken which contains two of the hexamantane components from Feedstock B. The preparative capillary gas chromatograph used was manufactured by Gerstel, Inc., Baltimore, Md., USA.

Figure 14B:
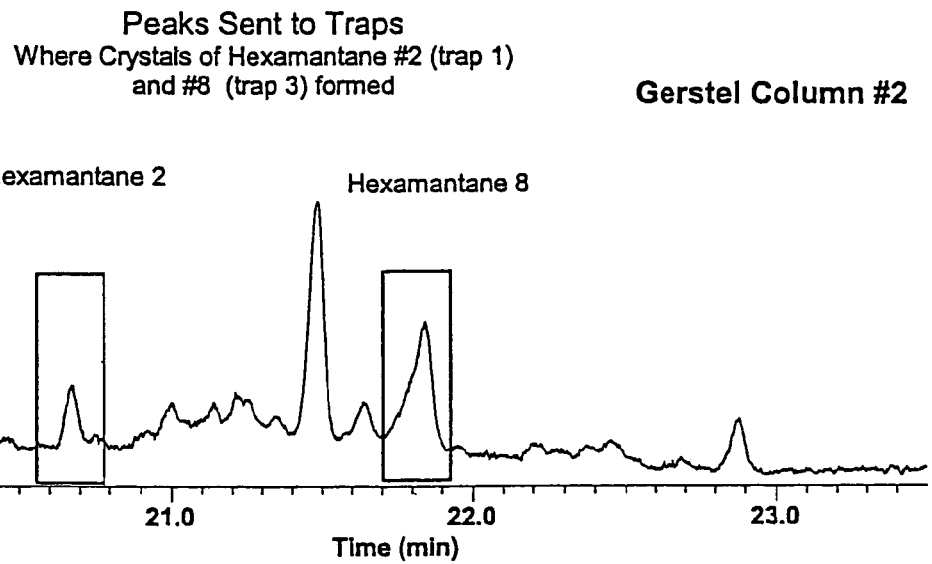
Figure 15C:
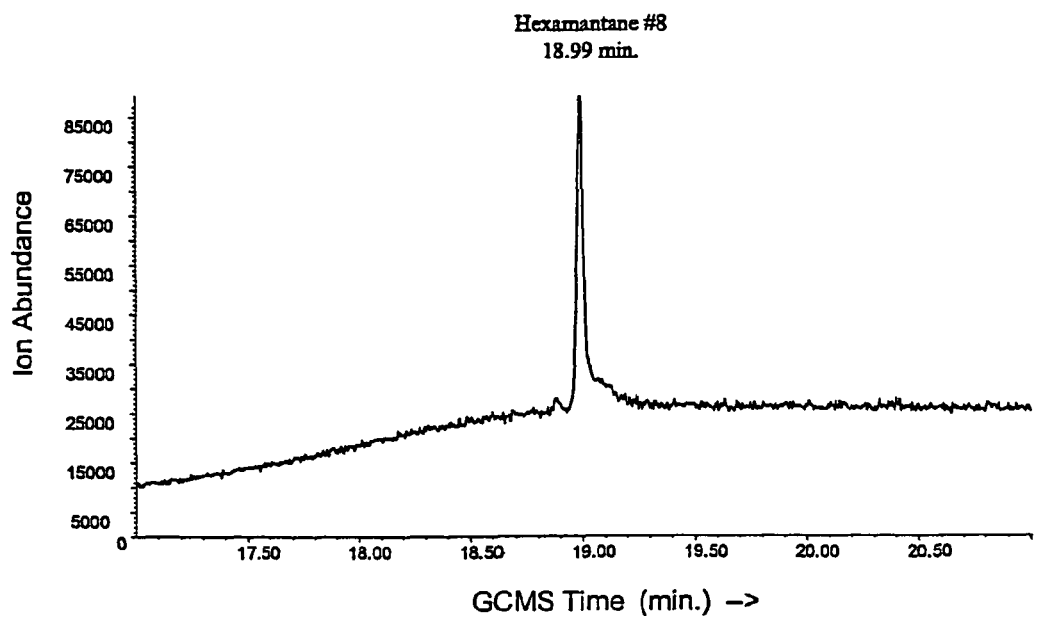
FIGS. 15C and 15D illustrate the GC/MS total ion chromatogram and mass spectrum of hexamantane #8.
Figure 15D:
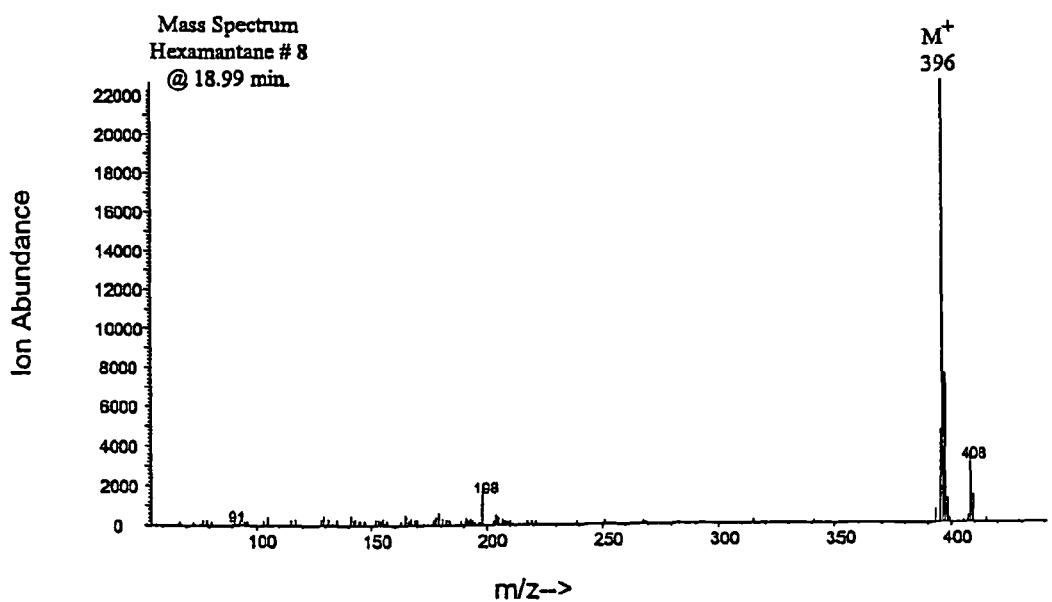

The first column was used to concentrate the higher diamondoids, such as hexamantanes by taking cuts that were then sent to the second column (see FIG. 14B illustrated for hexamantane #2 and #8). The second column, phenyl-methyl silicone, a DB-17 equivalent, further separated and purified the hexamantanes and then was used to isolate peaks of interest and retain them in individual traps (traps 1-6). GC trap fraction 1 contained crystals of hexamantane #2. GC trap fraction 3 contained crystals of hexamantane #8. Subsequent GC/MS analysis of trap #1 material (FIGS. 15A and 15B) showed it to be high purity hexamantane #2 based upon the GC/MS assay of Step 2. Similarly, the GC analysis of trap #3 material (FIGS. 15B and 15D) showed it to be primarily hexamantane #8. Photomicrographs of hexamantane #2 and #8 crystals. This procedure could be repeated to isolate the other hexamantanes. This is also true of the other higher diamondoids.

Example 3

Steps 1, 2, 3, and 4 (FIG. 7) of Example 1 were repeated using Feedstock A. Feedstock A is especially low in nondiamondoids in the atmospheric residue fraction recovered in Step 4. The pyrolysis Step (5) of Example 1 may be omitted especially when the higher diamondoids being sought are tetramantanes, pentamantanes and cyclohexamantane. In this case the fractions removed in Step 4 go directly to Steps 6 and 7 in Example 1 or directly to Step 7 in Example 2 (FIG. 7). This process variation can be applied to lower-boiling tetramantane-containing fractions of Feedstock B as well. However, pyrolysis is highly desirable where significant nondiamondoid components are present.

A fraction corresponding in cut point to fraction #1 of Step 4 (see distillation Table 3, Example 1 and FIG. 8) was taken from this feedstock. This fraction was further fractionated by preparative capillary gas chromatography similar to the processing shown in Step 7' of Example 2 (FIG. 7).

A two-column preparative capillary gas chromatograph was then used to isolate the target tetramantanes from the distillate fraction cleaned-up by column chromatography (Step 6, FIG. 7). Using the retention times and patterns from the GC/MS assay (from Step 2 of Example 1), the cut times for the target diamondoids (e.g., tetramantanes) were set for the first preparative capillary GC column, methyl silicone DB-1 equivalent. The results are shown on the top of FIG. 16 identified as cuts 1, 2 and 3.

Figure 16:
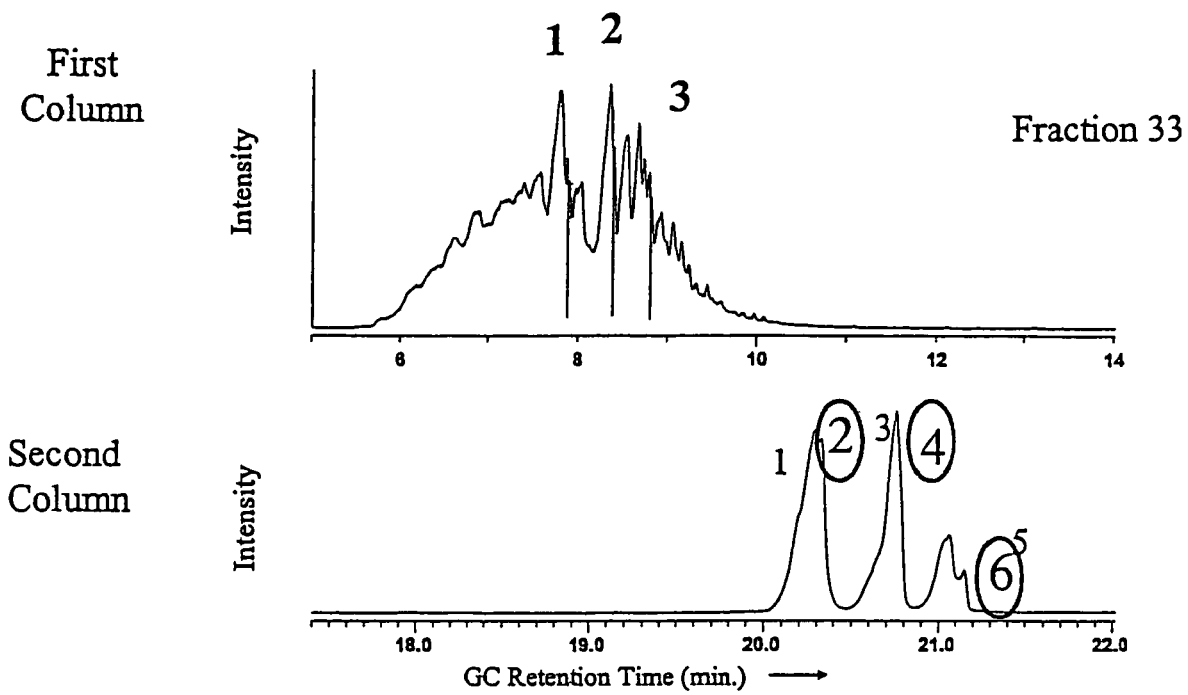
FIG. 16 illustrates the preparative capillary gas chromatographic data for tetramantane isolations carried out in Example 3. The first column shows cuts made on distillate fraction 33, Feedstock A. The bold face numbers refer to peaks of the tetramantanes. The second column shows peaks isolated and sent to the traps. The circled numbered peaks (2, 4, and 6) are the tetramantanes. It is noted that both enantiomers of the optically-active tetramantane are contained within one of these peaks.

The first column was used to concentrate the target diamondoids (e.g., tetramantanes) by taking cuts that were then sent to the second column (phenylmethyl silicone, a DB-17 equivalent) (see the bottom of FIG. 16). The second column further separated and purified the target diamondoids and then sent them into individual traps (traps 1-6). GC traps 2, 4 and 6 contained the selected tetramantanes (FIG. 16).

The highly concentrated tetramantane higher diamondoids were then allowed to crystallize in the trap or dissolved and recrystallized from solution. Under the microscope at 30× magnification, crystals of the tetramantanes were visible in preparative GC traps 2, 4, and 6. Where concentrations were not high enough for crystallization to occur, further concentration by preparative GC was necessary. The process would also work to isolate other higher diamondoids from Feedstock A.

Example 4

Preparative GC of HPLC Fractions

With the heptamantanes, octamantanes and higher diamondoids, etc., it may be desirable to further fractionate the HPLC products obtained in Example 1, Step 7. This can be carried out using preparative capillary gas chromatography as described in Example 2, Step 7'.

The following higher diamondoid components were isolated and crystallized: all of the tetramantanes from both Feedstocks A and B, all pentamantanes (mol. wt. 344) isolated from Feedstock B; two hexamantane crystals (mol. wt. 396) isolated from Feedstock B; and, two heptamantane crystals (mol. wt. 394) isolated from Feedstock B, octamantane crystal (mol. wt 446) isolated from Feedstock B. As well as a nonamantane crystal (mol. wt. 498) and a decamantane crystal (mol. wt. 456) isolated from Feedstock B. The other higher diamondoid components could also be isolated using the procedures set forth in these examples.

Example 5

Bromination of Higher Diamondoid Containing Feedstock

Bromination of a feedstock containing a mixture of higher diamondoids was carried out.

The feedstock was derived from Feedstock B described in Example 1. A sample of Feedstock B was subjected to atmospheric distillation as set forth in Example 1, Step 3. At the completion of the distillation a holdup fraction was obtained by rinsing the column. Its composition was similar to that of vacuum distillation fraction 1 indicated in FIG. 9. The holdup fraction was fractionated on a Whatman M40 10/50 ODS preparative scale HPLC column using acetone as mobile phase.

Figure 17:
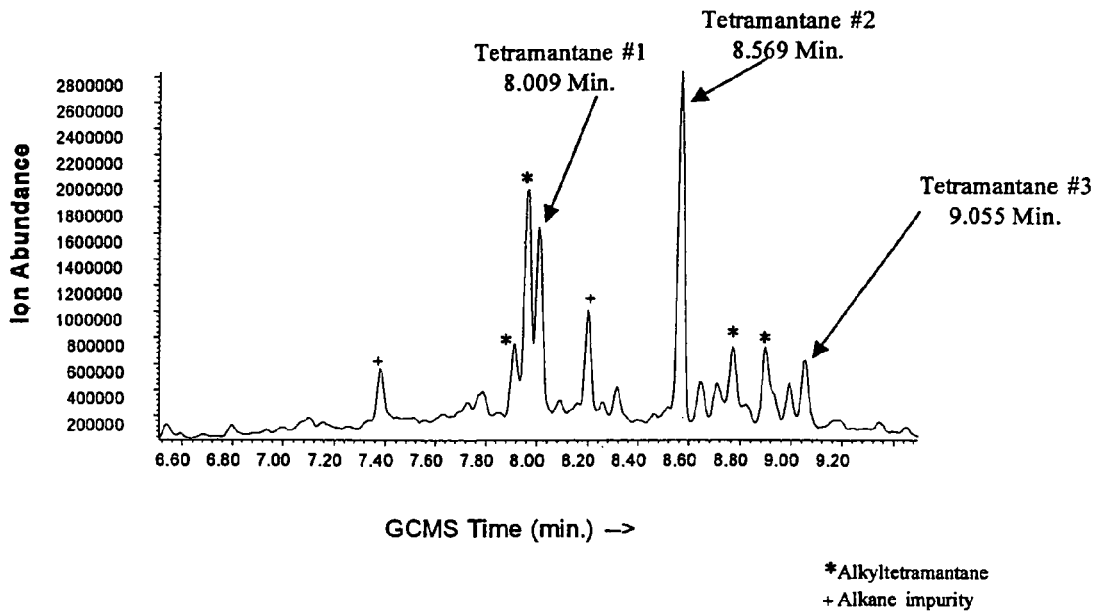
FIGS. 17-34 relate to the preparation of brominated higher diamondoids (tetramantanes and alkyltetramantanes).

A fraction containing all of the tetramantanes including some alkyltetramantanes and hydrocarbon impurities was obtained. The composition of this fraction is shown in FIG. 17. The tetramantanes were identified by mass spectra and retention times.

This fraction (about 10 mg) was mixed with anhydrous bromine excess (dried with concentrated $H_2SO_4$) in a 10 mL round-bottom flask. While stirring, the mixture was heated in an oil bath for about 4.5 hours under nitrogen, whereby the temperature was gradually raised from room temperature to about 100° C. The excess bromine was then removed by evaporation and the resulting brownish product was characterized by GC/MS.

Figure 18:
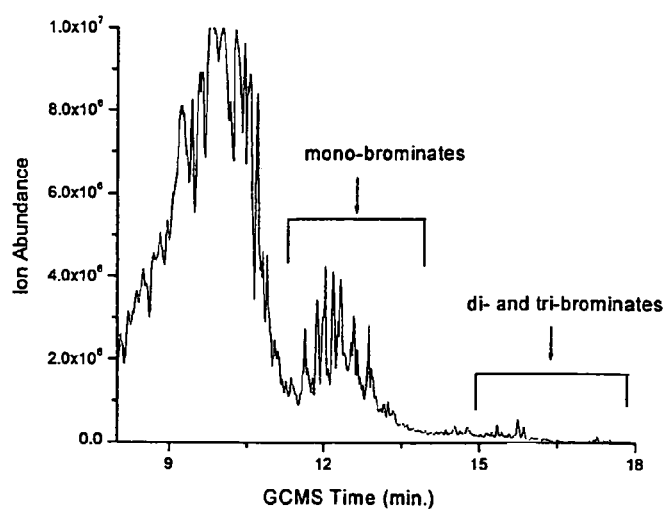

FIG. 18 shows the monobrominated, dibrominated and tribrominated tetramantane products formed (characterized by molecular ion 371, 447 and 527 respectively).

Figure 19:
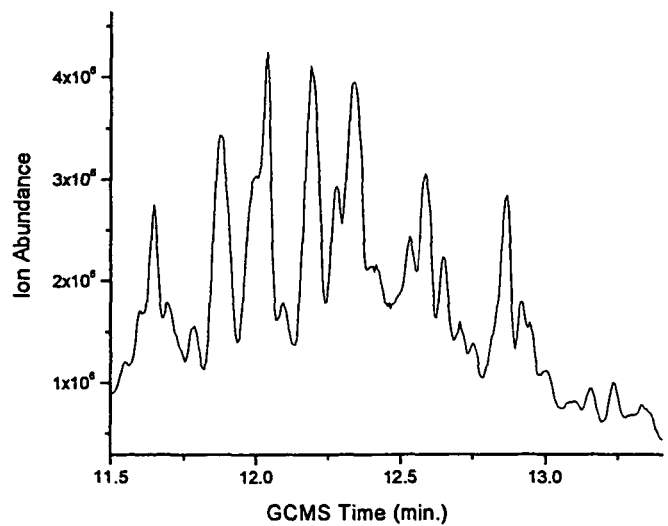

FIG. 19 shows the presence of monobrominated tetramantanes in the total ion chromatogram of the reaction product showing that these compounds are the major components within this GC/MS retention time range.

Figure 20:
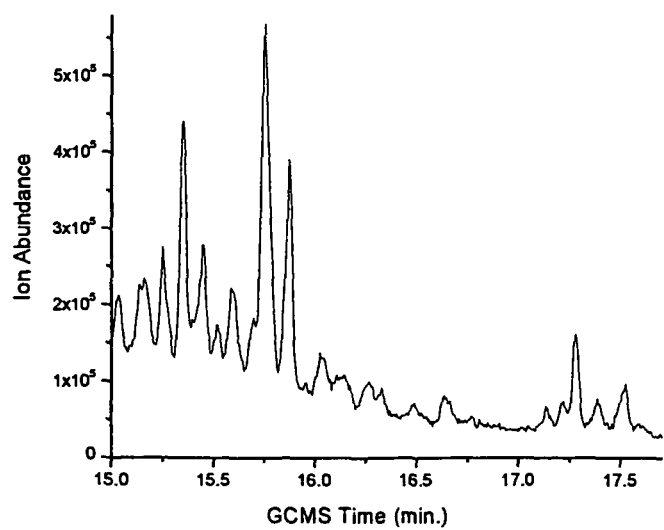

FIG. 20 shows the presence of di- and tri-brominated tetramantane products in the reaction mixture as the major components within this GC/MS retention time range.

Figure 21:
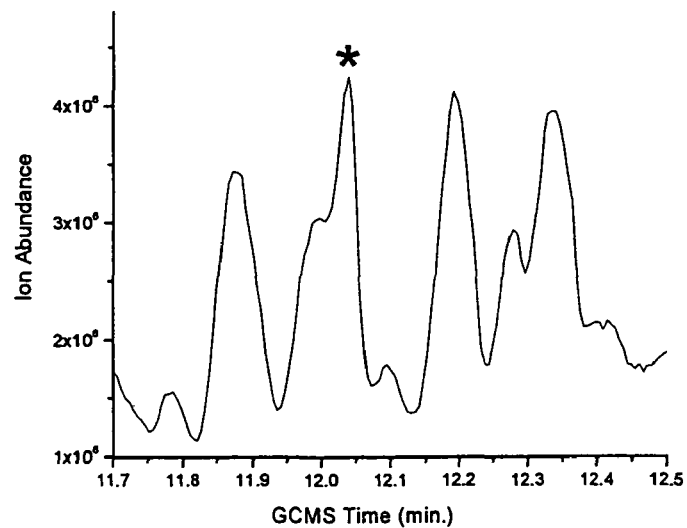

FIG. 21 shows the presence of a monobrominated tetramantane in the total ion chromatogram of the reaction mixture.

Figure 22:
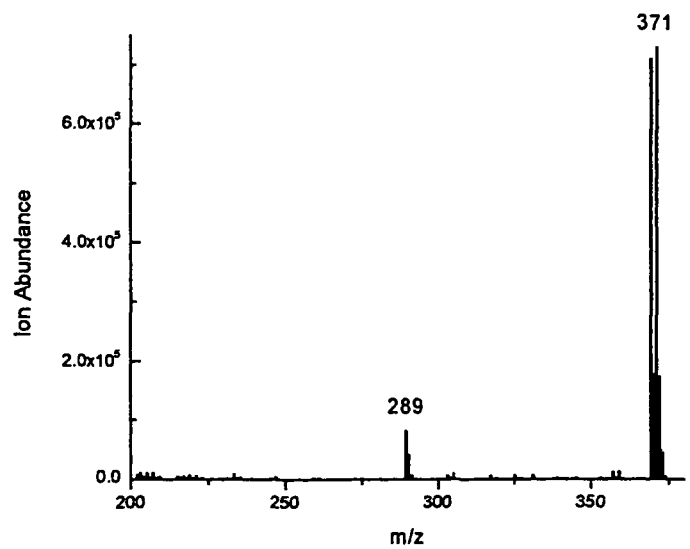

FIG. 22 is the mass spectrum of a monobrominated tetramantane with GC/MS retention time of 12.038 minutes from (FIG. 21). The base peak in this spectrum is the 371 m/z molecular ion.

Figure 23:
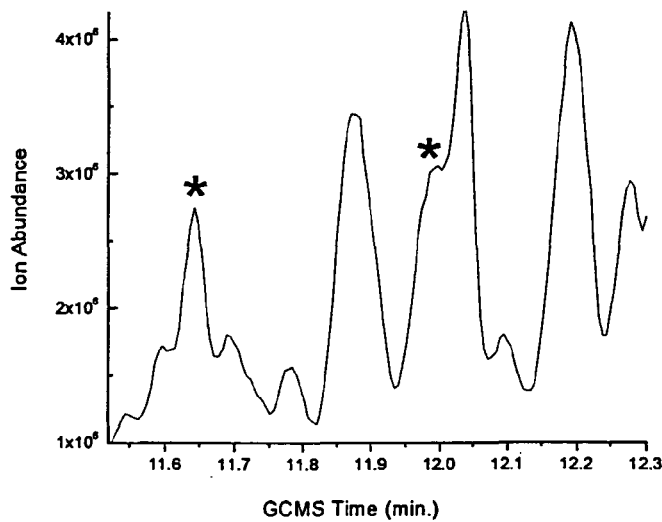

FIG. 23 shows the presence of monobrominated methyltetramantanes in the total ion chromatogram of the reaction product.

Figure 24:
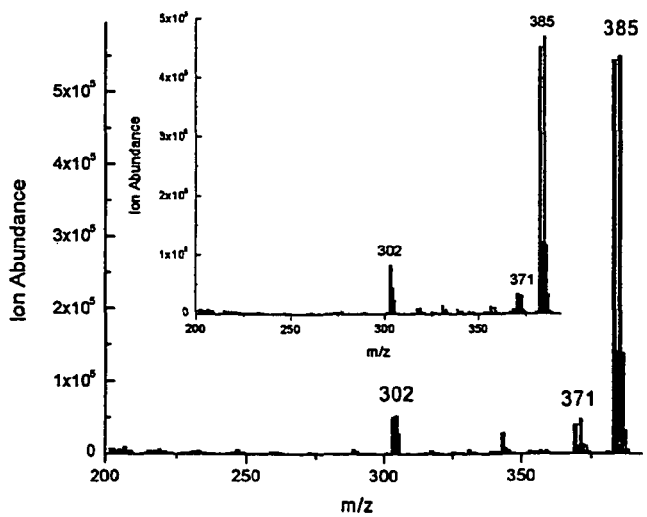

FIG. 24 are the mass spectra of monobrominated methyltetramantanes from FIG. 23 with GC/MS retention times of 11.992 minutes and 11.644 minutes. The base peak in this spectrum is the 385 m/z molecular ion.

Figure 25:
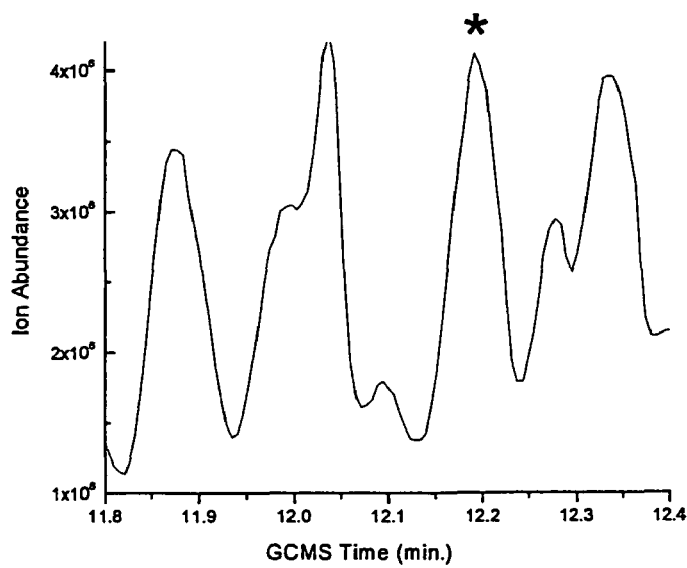

FIG. 25 shows the presence of brominated dimethyltetramantane in the total ion chromatogram of the product.

Figure 26:
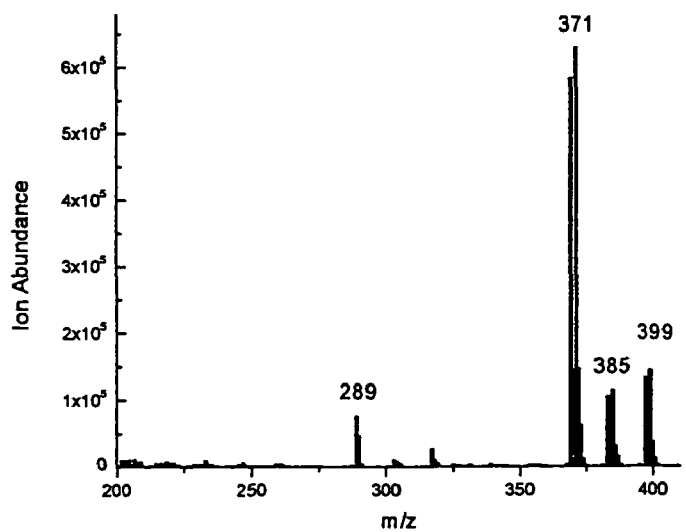

FIG. 26 is the mass spectrum of the monobrominated dimethyltatramantane eluting at 12.192 minutes from FIG. 25.

Figure 27:
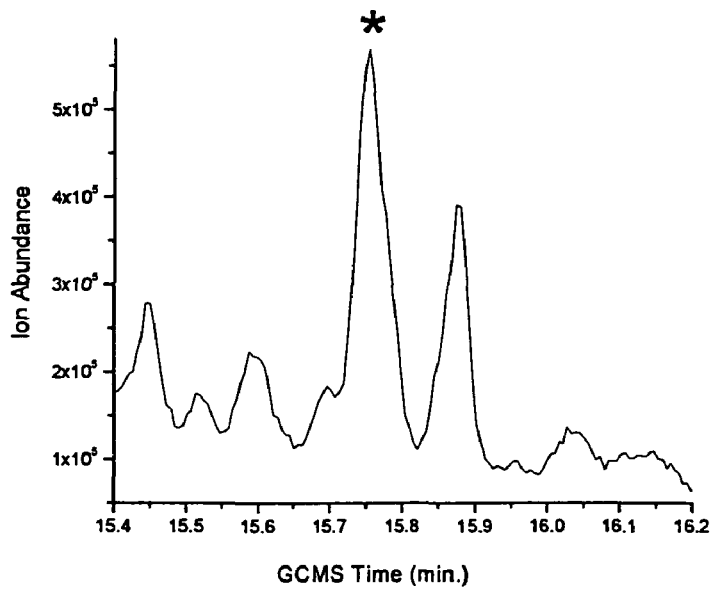

FIG. 27 shows the presence of dibrominated tetramantane in the total ion chromatogram of the reaction product.

Figure 28:
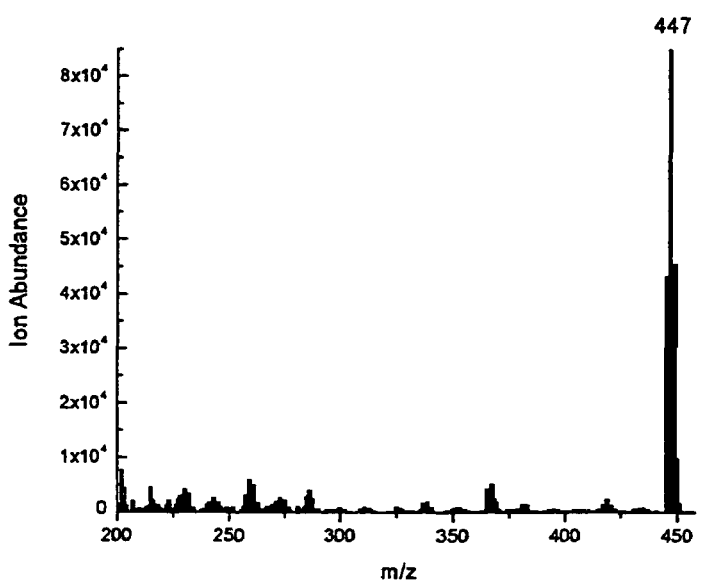

FIG. 28 is the mass spectrum of a dibrominated tetramantane with GC/MS retention time of 15.753 minutes from FIG. 27. The base peak in this spectrum is the 447 m/z molecular ion.

Figure 29:
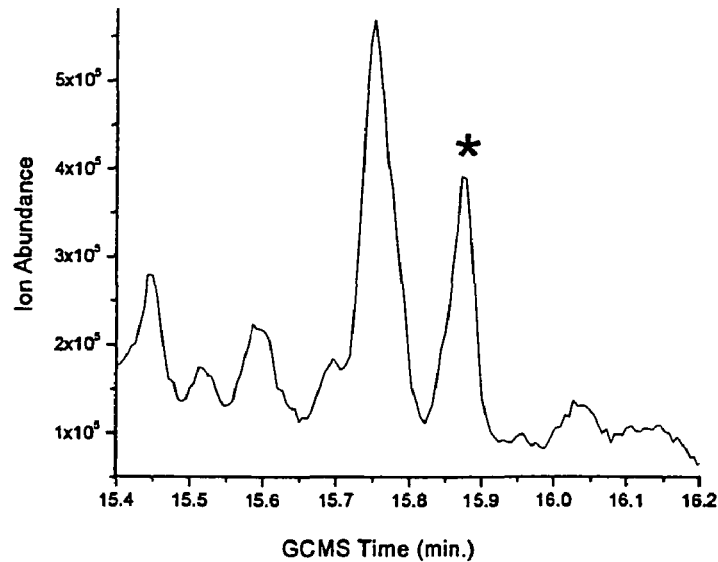

FIG. 29 shows the presence of dibrominated methyltetramantane in the total ion chromatogram of the reaction product.

Figure 30:
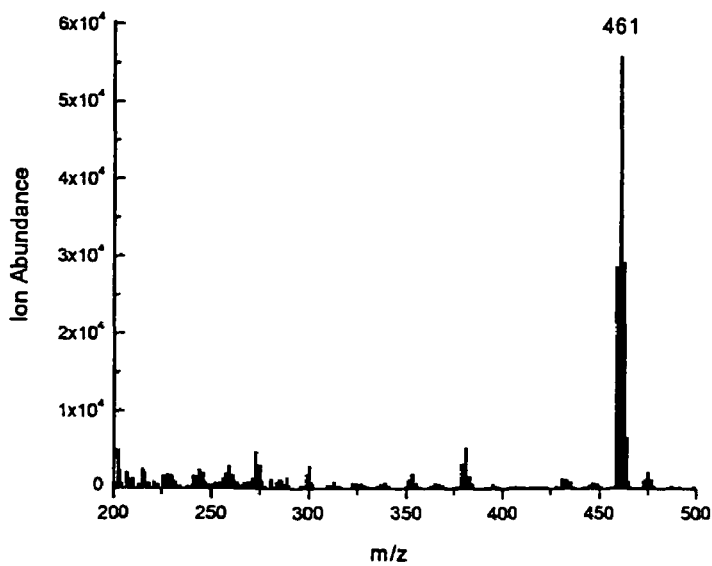

FIG. 30 is the mass spectrum of a dibrominated methyltetramantane with GC/MS retention time of 15.879 minutes from FIG. 30. The base peak in this spectrum is the 461 m/z molecular ion.

Figure 31:
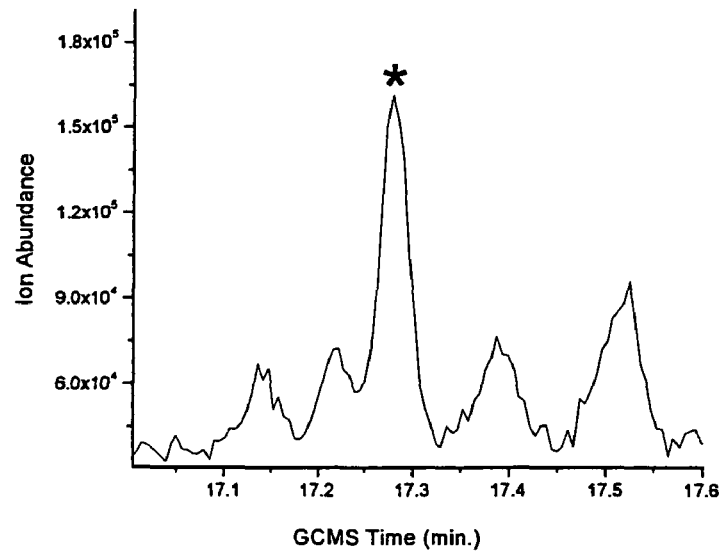

FIG. 31 shows the presence of tribrominated tetramantane in the total ion chromatogram of the reaction product.

Figure 32:
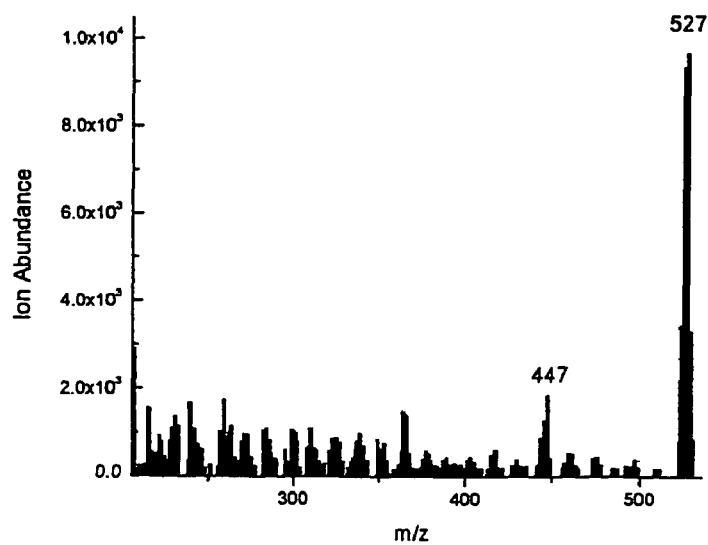

FIG. 32 is the mass spectrum of a tribrominated tetramantane with GC/MS retention time of 17.279 minutes from FIG. 31. The base peak in this spectrum is the 527 m/z molecular ion.

Figure 33:
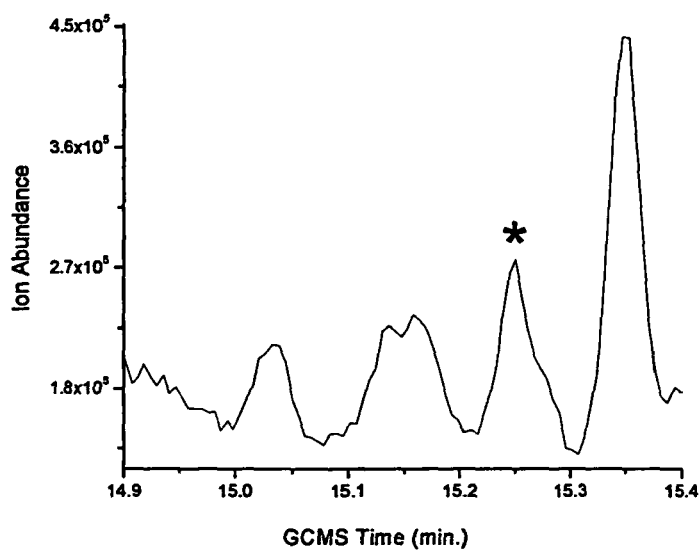

FIG. 33 shows the presence of tribrominated methyltetramantane in the total ion chromatogram of the reaction product.

Figure 34:
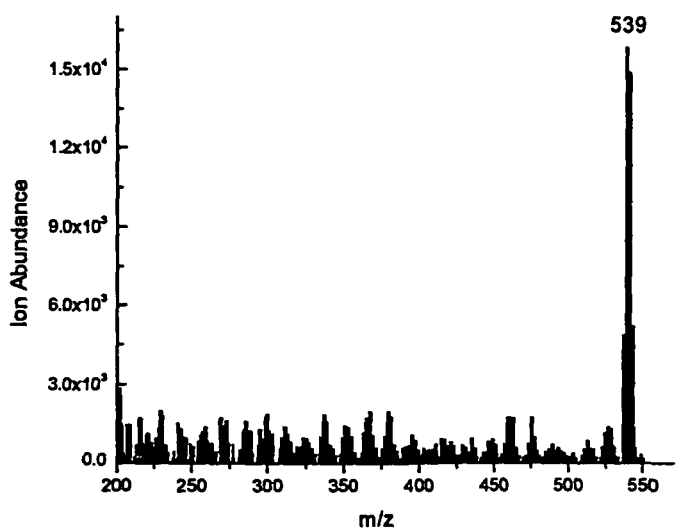

FIG. 34 is the mass spectrum of a tribrominated methyltetramantane with GC/MS retention time of 15.250 minutes from FIG. 34. The molecular ion is 541 m/z.

Example 6

Monobromination of Higher Diamondoids

A higher diamondoid (7.4 mmol) is mixed with anhydrous bromine (74 mmol) in a 150 mL round bottom flask. While stirring, the mixture is heated in an oil bath for about 4.5 h, whereby the temperature is gradually raised from an initial 30° C. to 105° C. The product monobrominated higher diamondoid dissolved in excess bromine is cooled and then taken up with 100 mL carbon tetrachloride which is poured into 300 mL ice water. The excess bromine is removed with sodium hydrogen sulfide while continuing cooling with ice water. After the organic phase has been separated, the aqueous solution is extracted once more with carbon tetrachloride. The combined extracts are washed with water, three times. After the organic phase has been dried with calcium chloride, the solvent is distilled off and the last residues are removed under vacuum. The residue is dissolved in a small amount of methanol and crystallized in a cold bath. Further purification of the crystals is carried out by sublimation under vacuum.

Example 7

Dibromination of Higher Diamondoids without Catalysts

A higher diamondoid (37 mmol) is heated to 150° C. for about 22 h with anhydrous bromine (0.37 mol) in a pressure vessel. The typical work-up and recrystallization of the oily reaction product from methanol is performed as described above. The crystals are sublimated in vacuum. The sublimate is recrystallized several times from a very small amount of n-hexane affording a pure dibrominated derivative.

Example 8

Dibromination of Higher Diamondoids with Catalysts

To a stirred mixture of 1.0 mol anhydrous bromine and 0.025 mole (2.5 mL) of boron bromide is added a few milligrams of aluminum bromide. The reaction mixture is maintained under a blanket of nitrogen during addition of reactants to a four-necked flask with stirrer, reflux condenser, and gas inlet. A higher diamondoid (0.1 mole) is added portionwise from a small flask attached to the fourth neck by means of Gooch crucible tubing. After refluxing for about 1.5 hours, hydrogen bromide evolution is no longer evident. Excess bromine is decomposed and the product isolation is accomplished as described above. After removal of the solvent, the residue is recrystallized frum methanol and n-hexane at room temperature to provide a pure dibrominated compound.

Example 9

Brominated Higher Diamondoids from Hydroxylated Compounds

A mixture of a suitable hydroxylated higher diamondoid and excess 48% hydrobromic acid is heated to reflux for a few hours (which can be conveniently monitored by GC analysis), cooled, and extracted with ethyl ether. The extract is combined and washed with aqueous 5% sodium hydroxide and water, and dried. Evaporation and normal column chromatography on alumina eluting with light petroleum ether, hexane, or cyclohexane, or their mixtures, with ethyl ether affords the bromide with reasonably high yields.

Example 10

Monophotochlorination of Higher Diamondoids

Photochlorination of a higher diamondoid is carried out at room temperature (25-30° C.) by metering 0.037 mole of chlorine into a solution of 0.074 mole of a higher diamondoid in 100 mL of solvent in the presence of illumination by a 150-watt ultraviolet (UV) lamp. The solvents employed can be carbon tetrachloride, benzene, or carbon disulfide. After a short induction period (approximately 2 minutes) the reaction may be initiated as evidenced by the fading of the chlorine color and the evolution of hydrogen chloride. The reaction mixture is washed by 5% sodium carbonate aqueous solution, water, and dried over anhydrous sodium sulfate. The product obtained by concentration of the dried solution is shown by GC to consist of several mono-chlorinated higher diamondoid isomers. Separation of those isomers is achieved by HPLC or even normal column chromatography on alumina, or silica gel, or simply by recrystallization from methanol and sublimation under vacuum, or by a combination of separation techniques as described herein to achieve the isomer separation.

Example 11

Monochlorination of Higher Diamondoids

A solution of 0.074 mole of a higher diamondoid and 10 mL (8.5 g, 0.092 mole) of tert-butyl chloride in 40 mL of anhydrous cyclohexane is prepared in a 0.1 L, three-necked, round-bottom flask fitted with a thermometer, a stirrer, and a gas exhaust tube leading to a bubbler submerged in water. The catalyst, aluminum chloride (total 0.46 g, 0.006 mole), is added in batches of 0.05g at regular intervals over a period of about 8 hours. Progress of the reaction is followed conveniently by the rate of escaping isobutane gas. Upon completion of the reaction, 10 mL of 1.0 N hydrochloride acid solution is added with vigorous stirring, followed by 50 mL of ethyl ether. The organic layer is separated, washed with 10 mL of cold water and 10 mL of a 5% sodium bicarbonate solution, and dried over anhydrous calcium chloride. After removal of the solvents under reduced pressure, the crude product is obtained. A GC analysis of this material reveals a composition of mainly monochlorinated higher diamondoids with a small amount of unreacted higher diamondoid. If necessary, recrystallization of a sample of this material from ethanol at −50° C. affords a pure monochlorinated higher diamondoid.

Example 12

Monohydroxylation of Higher Diamondoids

A solution of 11.0 mmol of a higher diamondoid in 18.7 g of methylene chloride is mixed with 4.22 g of a solution of 1.03 g (13.5 mmol) of peracetic acid in ethyl acetate. While being stirred vigorously, the solution is irradiated with a 100-watt UV light placed in an immersion well in the center of the solution. Gas evolution is evident from the start. The temperature is maintained at 40-45° C. for an about 21-hour irradiation period. At the end of this time, about 95% of the peracetic acid had been consumed. The solution is concentrated to near dryness, treated twice in succession with 100-mL portions of toluene and reevaporated to dryness. Final drying in a desiccator affords a white solid. A portion of the above material is dissolved in a minimum amount of benzene-light petroleum ether. This solution is then subjected to chromatography on alumina in the usual manner eluting with firstly 1:1 benzene/light petroleum ether, followed by a mixture of methanol and ethyl ether, to collect the unreacted higher diamondoid and the hydroxylated higher diamondoid isomers, respectively. Further separation of the isomers can be achieved by using HPLC techniques.

Alternatively, to 25 mL of acetic acid are added 10 mmol of a higher diamondoid, 0.8 mmol of N-hydroxyphthalimide (NHPI) and 0.6 mmol of acetylacetonatocobalt(II). The resultant mixture is stirred in an oxygen atmosphere at a temperature of 75° C. for about 3 hours. The reaction is monitored by GC, allowing for the isolation of the monohydroxylated higher diamondoid upon completion.

Example 13

Monohydroxylated Higher Diamondoids from Monobrominated Compounds

A suitable monobrominated higher diamondoid (0.066 mol) is heated to reflux for about 1 h in a round bottom flask. This flask is equipped with a stirrer and a reflux condenser to which 35 mL water, 3.5 mL tetrahydrofuran, 2.0 g potassium carbonate and 1.3 g silver nitrate is added while stirring the mixture. After cooling, the reaction product has crystallized, is separated and extracted with tetrahydrofuran. The extract is diluted with water and the precipitate is suctioned off, dried and purified by sublimation under vacuum.

Alternatively, a suitable monobromo higher diamondoid (0.1 mole) is mixed with 40 mL of 0.67 N hydrochloric acid and 450 mL DMF. The resultant mixture is stirred at reflux temperature for about 1 hour. The solid product is filtered and recrystallized from n-hexane to produce the monohydroxylated higher diamondoid.

Example 14

Dihydroxylated Higher Diamondoids from Dibrominated Compounds

A suitable dibrominated higher diamondoid (0.066 mol) is heated, refluxing for about 1 h in a round bottom flask. The flask is equipped with a stirrer and a reflux condenser. While stirring, the following is added: 70 mL water, 10 mL tetrahydrofuran, 4.0 g potassium carbonate and 2.6 g silver nitrate. After cooling, the reaction product is separated out and extracted with tetrahydrofuran. The extract is diluted with water and the precipitate is suctioned off, dried and purified by sublimation under vacuum.

Alternatively, a mixture of a dibromo higher diamondoid (0.12 mole) and 70% nitric acid (200 mL) is heated at 70-75° C. until bromine evolution ceases. The reaction mixture is poured into water (250 mL) and the precipitate is filtered. The filtrate is made alkaline with 10% aqueous sodium hydroxide and the mixture is filtered. The combined precipitates are washed with water (3×200 mL) and acetone (2×150 mL) and dried to provide the desired compound.

Example 15

Polyhydroxylation of Higher Diamondoids

Into a 4-neck flask immersed in a cooling bath equipped with the following: a low temperature condenser (−20° C.), an air driven well-sealed mechanical stirrer, a solid addition funnel and a thermocouple. To this flask the following is added: 0.037 mole of a higher diamondoid, 150 mL methylene chloride, 200 mL double distilled water, 192 grams sodium bicarbonate and 300 mL t-butanol. This mixture is stirred and cooled to 0° C. and 200 grams 1,1,1-trifluoro-2-propanone (TFP) is added. The mixture is stirred and cooled down to −8° C. Then, 200 grams oxone is added from the solid addition funnel over the course of 3 hours. The reaction mixture is stirred at 0° C. approximately overnight (16 hours). The TFP is recovered by distillation (heating pot to 40° C. and condensing TFP in a receiver immersed in dry ice/acetone). The remainder of the mixture is filtered by suction and a clear solution is obtained. The solution is rotavapped to dryness, providing a mixture of polyhydroxylated higher diamondoids that can be purified by chromatography and/or recrystallization.

Example 16

Oxidation of Higher Diamondoids to Higher Diamondoidones

A solution of 11.0 mmol of a suitable higher diamondoid in 18.7 g of methylene chloride is mixed with 4.22 g of a solution of 1.03 g (13.5 mmol) of peracetic acid in ethyl acetate. While being stirred vigorously, the solution is irradiated with a 100-watt UV light placed in an immersion well in the center of the solution. Gas evolution is evident from the start. The temperature is maintained at 40-45° C. for an about 21-hour irradiation period. At the end of this time, about 95% of the peracetic acid is consumed. The solution is concentrated to near dryness, treated twice in succession with 100-mL portions of toluene and is reevaporated to dryness. Final drying in a desiccator affords a solid.

The solid, a hydroxylated higher diamondoid mixture, is then partially dissolved in acetone. The oxygenated components of this mixture go into the solution but not all of the unreacted higher diamondoid. Chromic acid-sulfuric acid solution is added dropwise until an excess is present, and the reaction mixture is stirred overnight. The acetone solution is decanted from the precipitated chromic sulfate and the unreacted higher diamondoid, and is dried with sodium sulfate. The unreacted higher diamondoid is recovered by dissolving the chromium salts in water and filtering. Evaporation of the acetone solution affords a white solid. This crude solid is chromatographed on alumina with standard procedures eluting first with 1:1 (v/v) benzene/light petroleum ether, followed by ethyl ether, or a mixture of ethyl ether and methanol (95:5 v/v), to collect the unreacted higher diamondoid and the higher diamondoidone, respectively. Further purification by recrystallization from cyclohexane affords a pure higher diamondoidone.

Example 17

Monohydroxylated Higher Diamondoids at the Secondary Carbons from Higher Diamondoidones A suitable higher diamondoidone is reduced with lithium aluminum hydride (a little excess) in ethyl ether at low temperatures. After completion of the reaction, the reaction mixture is worked up by adding saturated $Na_2SO_4$ aqueous solution to decompose excess hydride at low temperature. Decantation from the precipitated salts gives a dry ether solution, which, when evaporated, affords a crude monohydroxylated higher diamondoid at the secondary carbon. Further recrystallization from cyclohexane gives a pure sample.

Example 18

Mononitration of Higher Diamondoids

A mixture of 0.05 mole of a higher diamondoid and 50 mL of glacial acetic acid is charged to a stirred stainless 100 mL autoclave, which is pressurized with nitrogen to a total pressure of 500 p.s.i.ga. After the mixture is then heated to 140° C., 9.0 g (0.1 mole) of concentrated nitric acid is introduced into the reaction zone by means of a feed pump at a rate of 1-2 mL per minute. When the acid feed is completed, the reaction temperature is maintained at 140° C. for 15 minutes, after which time the reaction mixture is cooled down to room temperature and diluted with an excess of water to precipitate the products. The filtered solids is then slurried with a mixture of 10 mL of methanol, 15 mL of water, and 1.7 g of potassium hydroxide for 18 hours at room temperature. After dilution with water, the alkali-insoluble material is extracted by light petroleum ether. The petroleum ether extracts is washed by water and dried over anhydrous magnesium sulfate. Concentration of this solution affords a white solid. The aqueous alkali solution from which the alkali-insoluble material had been extracted is cooled to 0-3° C. and neutralized by the dropwise addition of an aqueous acetic acid-urea mixture to regenerate some more products. GC analysis shows that the alkali-insoluble sample is mainly mononitro higher diamondoid with a small amount of dinitro product as well as a few unidentified components in minor quantities. The separation of analytically pure mononitro product from the other components of the alkali-insoluble product is difficult. However, by recrystallization from methanol and repeated sublimation, a pure sample of mononitro higher diamondoid is obtained.

Example 19

Mononitro Higher Diamondoids from Monoamino Compounds

A suspension of 0.01 mole of a suitable monoaminated higher diamondoid in 50 mL water is heated to 60° C. To this suspension a solution of 3.5 g potassium permanganate in 50 mL water (about 1 hour) is gradually added dropwise. After this permanganate solution has been added, the mixture is heated to reflux for about 2 hours, whereby the fraction sublimating in the condenser is washed back in again. At the end of the reaction, the crystals located in the condenser are rinsed out with dilute hydrochloric acid, stirred a little longer in the hydrochloric acid to remove the unreacted amine and filtered off. The crystals are purified twice by sublimation under vacuum.

Example 20

Monocarboxylation of Higher Diamondoids

A mixture of 29.6 g (0.4 mole) tert-butanol and 55 g (1.2 mole) 99% formic acid is added dropwise over about 3 hours to a mixture of 470 g 96% sulfuric acid and 0.1 mole higher diamondoid dissolved in 100 mL cyclohexane while stirring vigorously at room temperature. After decomposing with ice, the acids are isolated and purified by recrystallization from methanov/water giving the monocarboxylated higher diamondoid. In addition to using cyclohexane one can also use n-hexane as the solvent for the reaction. A test with only 50 mL cyclohexane indicates a substantially worse yield.

Example 21

Monocarboxylated Higher Diamondoids from Monobrominated Compounds

In 360 mL concentrated sulfuric acid, which has been cooled to +10° C., is placed in a 1-L three-necked flask, which is equipped with a stirrer, a reflux condenser and an Anschütz top with two dropping funnels. After removing the ice bath, while stirring, a suitable monobrominated higher diamondoid (0.056 mole) dissolved in 25 mL dry, highly pure n-hexane and 25.3 mL anhydrous formic acid is added dropwise into the flask in a course of about 1 hour with the resulting reaction mixture turning reddish brown. A fume hood is necessary to remove the carbon monoxide produced. After the dropwise addition has been completed, the mixture is vigorously stirred at room temperature for about an additional 2 hours. Then the reaction mixture is poured onto ice, whereby the acid precipitates out of solution. After standing for an additional about 2 hours, additional acid separates out. The acid is purified by dissolution in ether and extraction with dilute sodium hydroxide aqueous solution. The acid which precipitates during the acidification is recrystallized from dilute methanol.

Example 22

Monocarboxylated Higher Diamondoids from Monohydroxylated Compounds

A monocarboxylated higher diamondoid can be formed using a monohydratedoxlated precursor. When a monohydroxylated higher diamondoid is used, one follows the procedure described in Example 24 above, except that the amount of n-hexane must be increased to 150 mL due to the lower solubility of the monohydroxalted higher diamondoid in n-hexane.

Example 23

Monochlorocarboxylated Higher Diamondoids from Monobrominated Compounds

A mixture of a suitable monobrominated higher diamondoid (0.012 mole) and 9.0 g trichloroethylene is added dropwise over about 4 hours into 24 mL 90% sulfuric acid at 103-106° C. while stirring. After the addition is completed, the mixture is stirred for about an additional 2 hours at the specified temperature above. Then the mixture is cooled down and hydrolyzed with ground ice. The precipitated product can be freed from the neutral fraction by dissolution in dilute sodium hydroxide solution and extraction with ethyl ether. When acidified with dilute hydrochloric acid solution, the carboxylic acid precipitates out of the alkaline solution. Further purification could be achieved by recrystallization from cyclohexane.

Example 24

Dicarboxylated Higher Diamondoids from Dihydroxylated Compounds

Formic acid (98%, 280 mL) is added dropwise to a stirred solution of a dihydroxylated higher diamondoid (0.091 mol) in concentrated sulfuric acid (96%, 1.3 L) at 0° C. The mixture is stirred at 0° C. for about 2 hours and then stirred at room temperature for about 4 hours, after which the mixture is then poured over ice/water. The resultant product is washed with water and acetone and dried to afford the dicarboxylated higher diamondoid.

Example 25

Monoacetaminated Higher Diamondoids from Monobrominated Compounds

A suitable monobrominated higher diamondoid (0.093 mole) is dissolved in 150 mL acetonitrile. While stirring the mixture, 30 mL concentrated sulfuric acid is slowly added to the solution, whereby the mixture heats up by reaction. After the mixture has been left standing for about 12 hours, the solution is poured into 500 mL ice water, whereby the monoacetamino higher diamondoid separates out in high purity. By neutralizing the filtrate an additional small amount of the reaction product can be obtained.

Example 26

Monoacetaminated Higher Diamondoids from Monohydroxylated Compounds

A suitable monohydroxylated higher diamondoid (0.046 mole) is dissolved in 120 mL highly pure glacial acetic acid and treated with 13 mL acetonitrile and 4 mL concentrated sulfuric acid. The reaction mixture is left standing (closed) for about 20 hours at room temperature, and then twice the volume of water is added to it. After a few hours the precipitated reaction product is filtered off, and after drying it is recrystallized from cyclohexane.

Example 27

Monoacetaminated Higher Diamondoids from Monocarboxylated Compounds

Within 12 minutes, 4.1 g (0.1 mole) acetonitrile and a suitable monocarboxylated higher diamondoid (0.018 mole) are added to 20 mL 100% sulfuric acid at room temperature while stirring vigorously. Ice is added after about 1.5-hour post reaction. Then a precipitate is separated out. The suspension is made basic with sodium hydroxide solution and suctioned over a glass frit. Recrystallization from cyclohexane affords the monoacetaminated higher diamondoid product.

Example 28

Monoformylaminated Higher Diamondoids from Monocarboxylated Compounds

Within 7 minutes, 8.16 g (0.17 mole) sodium cyanide and a suitable monocarboxylated higher diamondoid (0.028 mole) mixture is added to 100 mL 100% sulfuric acid while stirring vigorously. After ½ hour, decomposition is carried out by pouring the reaction mixture onto 250 g crushed ice which is then made basic by the addition of a sufficient amount of sodium hydroxide solution and extracted five times with benzene/ether. The solvent is removed in vacuo from the combined extracts and the residue is recrystallized from benzene/hexane to afford the monoformylaminated higher diamondoid.

Example 29

Monoarylated Higher Diamondoids from Monobrominated Compounds 1.1 g sublimated iron(III) chloride and 20 mL absolute thiophene-free benzene are placed in a 150-mL three-necked flask, which is equipped with a stirrer, a reflux condenser and a dropping funnel. While stirring and heating the mixture in the steam bath, a solution of a suitable monobrominated higher diamondoid (0.018 mole) in 30 mL benzene is added dropwise to the above flask over about 30 minutes. The reaction mixture is heated for about an additional 3 hours until the production of hydrogen bromide drops off. This mixture is kept standing over night and poured onto a mixture of ice and hydrochloric acid. The benzene phase is separated out and the aqueous solution is extracted twice with benzene. The combined benzene extracts are washed several times with water and dried with calcium chloride. The residue solidifies upon cooling and is completely free of the solvent in vacuum. Recrystallization from a small amount of methanol while cooling with $CO_2$/trichloroethylene and further sublimation under vacuum afford the monoalkylated higher diamondoid.

Example 30

Monoethenylated Higher Diamondoids from Monobrominated Compounds

Step 1: a solution of a suitable monobrominated higher diamondoid (0.046 mole) in 15 mL n-hexane in a 150-mL three-necked flask (equipped with a stirrer, a gas inlet tube and a gas discharge tube with a bubble counter) is cooled to −20 to −25° C. in a cooling bath. While stirring the flask 4.0 g powdered freshly pulverized aluminum bromide of high quality, and ethylene is added in such a way that the gas intake can be controlled with the bubble counter. The reaction is completed after about 1 hour. The reaction solution is decanted from the catalyst and into a mixture of ether and water. The ether layer is separated off, while the aqueous phase is extracted once more with ether. The combined ether extracts are washed with water and dilute sodium carbonate aqueous solution. After they have been dried over calcium chloride, ether is distilled off. The residue is separated by distillation under vacuum providing crystals of the higher diamondoidyl ethyl bromide.

Step 2: a solution of 0.7 g fine powdered potassium hydroxide and the above higher diamondoidyl ethyl bromide (0.012 mole) in 10 mL diethylene glycol is heated to 220° C. in the oil bath for 6 hours. After cooling down, the mixture is diluted with 30 mL water and exacted with ethyl ether. The ether extract is washed twice with water and dried over calcium chloride. The residue left behind after the ether has been distilled off is sublimated in vacuum, and if necessary for suitable purity, the compound can be recrystallized from methanol.

Example 31

Monoethynylated Higher Diamondoids from Monobrominated Compounds

Step 1: in a 150-mL two-necked flask with a stirrer and a drying tube, a mixture of 0.069 mole of a suitable monobromonated higher diamondoid and 20 mL vinyl bromide is cooled to −65° C. in a cooling bath. While stirring, 4.5 g powdered aluminum bromide is added in portions and the mixture is stirred for an additional about 3 hours at the same temperature. Then the reaction mixture is poured into a mixture of 30 mL water and 30 mL ethyl ether. After vigorously stirring, the ether layer is separated and the aqueous layer is extracted once more with ether. The combined ether extracts are washed with water and dilute sodium carbonate solution. After it has been dried with calcium chloride and the solvent has been distilled off, the residue is distilled under vacuum.

Step 2: 15 g powdered potassium hydroxide in 30 mL diethylene glycol is heated to reflux with 0.046 mole of the above product for about 9 hours in the oil bath. The monoethynylated higher diamondoid compound which is formed, is then sublimated in the condenser and must be returned to the reaction mixture from time to time. At the end of the reaction time, the reaction mixture is distilled until no more solid particles go over. The distillate is extracted with ethyl ether and the ether phase is washed with water and dried over calcium chloride. A short time after the ether has been distilled off, the residue solidifies. This residue is then sublimated under vacuum and, if necessary, recrystallized from methanol.

Example 32

Mono- and Diethynylated Higher Diamondoids from Monobrominated Compounds

A solution of a monobromo higher diamondoid (14.2 mmol) and vinyl bromide (5 mL) in $CH_2Cl_2$ (25 mL) is cooled with a dry ice-acetone bath (−30° C.). To this mixture aluminum bromide (4.9 mmol) is added, portionwise, over 30 minutes while the internal temperature is kept below −24° C., then the mixture is stirred at −30° C. for 45 min., diluted with $CH_2Cl_2$ and slowly poured over crushed ice and concentrated hydrochloric acid (20 mL). From this, the organic layer is separated and the aqueous layer is extracted with $CH_2Cl_2$. The combined organic layers are washed with brine, dried and filtered. Solvent is evaporated under reduced pressure to give an oil.

The oil is dissolved in DMSO (50 mL) and potassium t-butoxide (36 mmol) is added over 1 hour. The mixture is stirred at room temperature for 3 days and then heated at 50-55° C. for 3.5 hours. Standard isolation procedures with $CH_2Cl_2$ gives an oil. Bulb to bulb distillation provides a semi-solid residue. The residue is chromatographed on silica gel (hexane and 95:5 hexane/$CH_2Cl_2$) to afford the mono- and diethynylated higher diamondoid.

Example 33

Higher Diamondoids Monocarboxylic-Acid Ethyl Ester from Activated Monocarboxylated (Acid Chloride) Compounds 0.017 mole of a suitable monocarboxylated higher diamondoid is mixed with 4.2 g $PCl_5$ in a 50-mL flask with a stirrer and a reflux condenser. The reaction starts after approximately 30-60 seconds with liquefaction of the reaction mixture. The mixture is heated for about 1 hour while stirring the flask on the steam bath. The $POCl_3$ formed is distilled off under vacuum. The acid chloride left behind as a residue is cooled with ice water, and 6.0 mL absolute ethanol is added dropwise. This mixture is heated about an additional 1 hour on the steam bath allowed to cool and then poured into 50 mL. The ester is taken up with ethyl ether and then washed with potassium carbonate aqueous solution and water. After drying, fractionation is carried out over calcium chloride under vacuum.

Example 34

Diesterified Higher Diamondoids from Dihydroxylated Compounds

To 2 mL of dioxane is added a dihydroxylated higher diamondoid (1.0 mmol) and triethylamine (2.2 mmol) at a temperature of 50° C. The resultant mixture is added dropwise to a solution of acrylic acid chloride (2.2 mmol) in dioxane (2 mL). The mixture is maintained at 50° C. for about 1 hour. Until the desired diacrylate is formed, the compound is isolated using standard methods.

Example 35

Monomethylhydroxylated Higher Diamondoids from Monoesterified Compounds 0.014 mole of a suitable higher diamondoid monocarboxylic acid-ethyl ester dissolved in 10 mL absolute ether. This mixture is slowly added dropwise, to a room temperature stirred suspension of 0.8 g lithium alanate in 16 mL absolute ether. This mixture is stirred for an additional about 1 hour and then water is carefully added. The ether solution is separated out and the aqueous phase is extracted with ether two more times. After the combined extracts have been dried with calcium chloride, the ether is distilled off and the residue is recrystallized from methanol/water.

Example 36

Monoaminated Higher Diamondoids from Monoacetaminated Compounds

A suitable monoacetaminated higher diamondoid (0.015 mole) is heated to reflux for about 5 hours with a solution of 6 g powdered sodium hydroxide in 60 mL diethylene glycol. After it has been cooled down, the mixture is poured into 150 mL water and extracted with ethyl ether. The ether extract is dried with potassium hydroxide. The ether is distilled off and the residue is sublimated to afford the product monoaminated higher diamondoid.

Example 37

Monoaminated Higher Diamondoids from Mononitro Compounds

A mixture of 0.412 mmol of a mononitro higher diamondoid and 11.5 g of sodium sulfide nonahydrate in 400 mL of mixed solvent of THF/$H_2O$ (3:2 v/v) is vigorously stirred for about 12 hours at 75° C. After cooling to room temperature, the mixture is concentrated below 40° C. under reduced pressure until the volume is reduced to about 15 mL. The precipitate is filtered with suction followed by washing well with water and a 1.0 N HCl aqueous solution. This crude product is dissolved in chloroform or ethyl ether and washed with water (4×80 mL) to neutralize any sodium hydroxide in the organic phase (chloroform or ether) until the material is essentially free from sodium hydroxide and/or sodium chloride. After removal of the solvent, a crude product is obtained. The separation and purification of the product is carried out with column chromatography on neutral $Al_2O_3$ using chloroform/hexane as the eluent, to yield a pure monoaminated higher diamondoid. If necessary, further purification with column chromatography could be repeated for several times.

Example 38

Monoaminated Higher Diamondoids from Monochlorinated Compounds

A suitable monochlorinated higher diamondoid is converted by the acetonitrile-sulfuric acid procedure described above, to the monoacetaminated higher diamondoid. The crude amide, without prior purification, is saponified to afford a monoaminated higher diamondoid. Purification of the amine as described above gives a pure monoaminated higher diamondoid.

Example 39

Monoaminated Higher Diamondoids from Monocarboxylated Compounds

Step 1: 0.017 moles of a suitable monocarboxylated higher diamondoid is mixed with 4.2 g $PCl_5$ in a 50-mL flask equipped with a stirrer and a reflux condenser. The reaction starts after 30-60 seconds with liquefaction of the reaction mixture. The mixture is heated for an additional hour while stirring on a steam bath. The $POCl_3$ formed during the reaction is distilled off under vacuum to afford an acid chloride.

Step 2: a solution of the above higher diamondoidyl monocarboxylic acid-chloride (0.027 mole) in 12 mL absolute tetrahydrofuran is slowly added dropwise to a 60 mL of a concentrated aqueous ammonia solution, while stirring and cooling the mixture with ice water. The amide (higher diamondoidyl monocarboxylic acid-amide) is then separated out of the mixture as a precipitate. The precipitate is suctioned, washed well with water and recrystallized from cyclohexane after it has been dried.

Step 3: 0.018 mole of the above amide is dissolved in 25 mL absolute methanol. This solution is added to a solution of 1.0 g sodium in 25 mL absolute methanol, in a 150-mL three-necked flask with a stirrer, a reflux condenser and dropping funnel. To this flask 1.0 mL bromine is added dropwise with ice cooling, and then the mixture is slowly heated to around 55° C. (water bath temperature). After the mixture has been cooled, water is added and the precipitate is separated out by filtration. Further purification can be achieved by recrystallization from ethanol.

Step 4: the above product is finally saponified and worked up in the same way as described above to afford the target compound.

Example 40

Monoaminated Higher Diamondoids from Monobrominated Compounds

Step 1: a monobromo higher diamondoid (0.028 mol) is mixed with 40 in mL formamide. The resultant mixture is refluxed for about 12 hours. After cooling, the reaction mixture is poured into water and extracted with dichloromethane. The organic phase is dried with magnesium sulfate, filtered, and evaporated to dryness under vacuum to provide a mono N-formyl higher diamondoid.

Step 2: the above mono N-formyl higher diamondoid (0.023 mol) is mixed with 100 mL of 15% hydrochloric acid. The resultant mixture is heated to boiling for about 24 hours. After cooling, the precipitate is filtered and recrystallized from isopropanol to afford the monoamino higher diamondoid.

Example 41

2,2-Bis(4-hydroxyphenyl) Higher Diamondoids from Keto Compounds

A flask is charged with a mixture of a higher diamondoidone (0.026 mole), phenol (16.4 g, 0.17 mole), and butanethiol (0.15 mL). Heat is applied and when the reaction mixture becomes liquid at about 58° C., anhydrous hydrogen chloride is introduced until the solution becomes saturated. Stirring is continued at about 60° C. for several hours, during which period a solid forms. The solid obtained is filtered off, washed with dichloromethane and dried to afford the bisphenol higher diamondoid product. This product is purified by sublimation after recrystallization from toluene.

Example 42

2,2-Bis(4-aminophenyl) Higher Diamondoids from Keto Compounds

A higher diamondoidone (0.041 mole) in solution with 15 mL of 35% HCl aqueous solution housed in a 100 mL autoclave is combined with excess aniline (15.7 g, 0.17 mole) and the mixture is stirred at about 120° C. for about 20 hours. After cooling, the solution is made basic with addition of a NaOH aqueous solution to pH 10. The resulting oily layer is separated and distilled to remove the unreacted excess aniline. The residual crude product is recrystallized from benzene to afford the higher diamondoid derived bisphenylamine.

Example 43

2,2-Bis[4-(4-aminophenoxy)phenyl] Higher Diamondoids from Bisphenol Higher Diamondoids A mixture of a 2,2-bis(4-hydroxyphenyl) higher diamondoid (0.01 mole), p-fluoronitrobenzene (3.1 g, 0.022 mole), potassium carbonate (3.31 g, 0.024 mole) and N,N,-dimethylacetamide (DMAc, 10 mL) is refluxed for about 8 hours. The mixture is then cooled and poured into a ethanol/water mixture (1:1 by volume). The crude product is crystallized from DMF to provide the 2,2-bis[4-(4-nitrophenoxy)phenyl] higher diamondoid.

Hydrazine monohydrate (20 mL) is added dropwise to a mixture of the above product (0.002 mole), ethanol (60 mL), and a catalytic amount of 10% palladium on activated carbon (Pd/C, 0.05 g) at the boiling temperature. The reaction mixture is refluxed for about 24 hours, and the product 2,2-Bis [4-(4-aminophenoxy)phenyl] higher diamondoid is precipitated during this period. This mixture is then added to enough ethanol to dissolve the product and filtered to remove Pd/C. After cooling, the precipitated crystals are isolated by filtration and recrystallized from 1,2-dichlorobenzene.

Example 44

[Higher Diamondoid-Higher Diamondoid] from Monobromonated Higher Diamondoid

A suitable monobrominated higher diamondoid (50 mmole) is dissolved in 30 mL of xylene and heated to reflux in a three-necked flask fitted with thermometer, nitrogen inlet, stirrer, and reflux condenser, under a slow stream of nitrogen. Then a total of 1.15 g of small pieces of sodium metal is added to the stirred reaction mixture over a period of about 4 hours. After all sodium has been added, the mixture is refluxed for about an additional hour and then filtered in the hot state. On cooling to room temperature, the product higher diamondoid covalently bonded to a higher diamonoid is crystallized from the filtrate. Condensation of the filtrate provides some additional amount of the product. Recrystallization from benzene gives a pure sample. Alternatively, using the same procedure as above, a dibromonated higher diamondoid is used to form a three diamondoid product.

Example 45

Dibromination of Higher Diamondoid-Higher Diamondoid for production of Higher Diamondoid Polymer A suitable higher diamondoid covalently bonded to another higher diamondoid (14 mmole) is charged into a round-bottom flask fitted with a long reflux condenser. Then 20 mL of bromine is added with stirring, and hydrogen bromide is formed. Hydrobromic acid evolution ceases after about 15 min. the reaction mixture is then heated to reflux (ca. 61° C. pot temperature) for about 2 hours. The cooled reaction product is diluted with 75 mL of $CCl_4$ and transferred to a separatory funnel. The $CCl_4$ is then shaken with ice-water, and sodium bisulfite is added until excess bromine is destroyed. The organic layer is separated and the water layer is extracted twice with 50 mL of $CCl_4$. The combined organic solution is dried over sodium sulfate and the solvent is stripped under slight vacuum. The reaction product in the pot is precipitated with methanol, filtered off, and recrystallized from dioxane to give a Br-[Higher Diamondoid-Higher Diamondoid]-Br product. Such a reaction can be continued to form a higher diamondoid polymer.

Example 46

Polymerization of Diacrylated Higher Diamondoids

The following compositions are subjected to polymerization: diacrylated higher diamondoid; monoacrylated higher diamondoid; a 50:50 mixture by weight of monoacrylated higher diamondoids and methyl methacrylate; and, a 50:50 mixture by weight of monoacrylated higher diamondoid and diethylene glycol bis allylcarbonate. To the various compositions is added 0.1 part by weight of a photo-polymerization initiator (benzophenone). The mixture is applied to a glass plate and photo-polymerized by irradiation with ultraviolet light.

Example 47

Polymerization of Diethynylated Higher Diamondoids

A sample of a diethynylated higher diamondoid (275 mg) is sealed in a glass tube and heated to 200° C. for 14 hours and at 250° C. for 48 hours. The tube is cooled to room temperature and opened to afford a polymeric resin.

Example 48

Copolymerization of Monoethynylated Higher Diamondoids and Diethynylated Compounds A mixture of a monoethynylated higher diamondoid (55% by weight) and diethynylated higher diamondoid (45% by weight) is sealed in a tube and heated at 175° C. for 2 hours, 200° C. for 14 hours, 210° C. for 8 hours, 225° C. for 48 hours and at 250° C. for 16 hours. The tube is then cooled to room temperature and opened to give a polymeric resin.

Example 49

Polyesters Derived from 2,2-Bis(4-hydroxyphenyl) Higher Diamondoids by Solution Polycondensation A 2,2-bis(4-hydroxyphenyl) higher diamondoid (0.005 mole) is mixed with pyridine (2 mL) at room temperature for about 20 minutes. Terephthaloyl chloride (1.015 g, 0.005 mole) in nitrobenzene (20 mL) is added to the above solution at room temperature for about 5 minutes and then the mixture is heated to about 150° C. for about 10 hours. The resulting polymer solution is poured into methanol to precipitate the polymer. The polymer is washed with hot methanol, collected on a filter, and dried in vacuo at about 60° C. for about 24 hours.

Example 50

Polyamides Derived from 2,2-Bis[4-(4-aminophenoxy)phenyl] Higher Diamondoids by Solution Polycondensation A flask is charged with a mixture of a 2,2-bis[4-(4-aminophenoxy)phenyl] higher diamondoid (0.9 mmol), terephthalic acid (0.149 g, 0.9 mmol), triphenyl phosphite (0.7 mL), pyridine (0.6 mL), N-methyl-2-pyrrolidone (NMP, 2 mL) and calcium chloride (0.25 g). It is refluxed under argon for about 3 hours. After cooling, the reaction mixture is poured into a large amount of methanol with constant stirring, producing a precipitate that is washed thoroughly with methanol and hot water, collected on a filter, and dried to afford a polyamide containing higher diamondoid components along the polymer chain.

Example 51

Polyimides Derived from 2,2-Bis[4-(4-aminophenoxy)phenyl] Higher Diamondoids by Chemical Imidization To a stirred solution of a 2,2-bis[4-(4-aminophenoxy)phenyl] higher diamondoid (1.2 mmol) in DMAc (7 mL) is gradually added pyromellitic dianhydride (0.262 g, 1.2 mmol). The mixture is stirred at room temperature for 2-4 hours under argon atmosphere to form the poly(amic acid). Imidization is carried out by adding DMAc and an equimolar mixture of acetic anhydride and pyridine into the abovementioned poly(amic acid) solution with stirring at room temperature for about 1 hour and then heating at about 100° C. for an additional about 3 hours. The reaction product is subsequently poured into methanol and the precipitate is filtered off, washed with methanol and hot water, and dried to afford the polyimide containing higher diamondoid components along the polymer chain.

Example 52

Polyimides Derived from 2,2-Bis(4-aminophenyl) Higher Diamondoids by Chemical Imidization To a solution of a 2,2-bis(4-aminophenyl) higher diamondoid (5 mmol) in 17.9 mL of NMP, 3,3',4,4'-benzophenonetetracarboxylic dianhydride (BTDA, 98.6%, 1.61 g, 5 mmol) is added with a solid content of 15 wt %. The solution is continuously stirred at room temperature for about 24 hours. To the reaction mixture are added 1.5 mL of acetic anhydride and 2.0 mL of pyridine and then the temperature is raised to about 120° C. and kept at this temperature for about 3 hours. The resulting solution is poured into excess methanol and filtered. The precipitated polymer is washed several times with water and methanol, and then the polymer is dried at about 100° C. for around 12 hours in vacuo.

Example 53

Polyimides Derived from 2,2-Bis(4-aminophenyl) Higher Diamondoids by Solution Polymerization To a solution of a 2,2-bis(4-aminophenyl) higher diamondoid (5 mmol) in 19 mL of freshly distilled m-cresol, 3,3',4,4'-benzophenonetetracarboxylic dianhydride (98.6%, 1.61 g, 5 mmol) and isoquinoline (0.95 mL) as a catalyst are added at room temperature under nitrogen atmosphere. The reaction mixture is heated to about 70~80° C. over 2 hours and kept at this temperature for about 2 hours. Afterwards, the solution temperature is slowly raised to about 200° C. over 2 hours and refluxed for 6 hours. The polymerization is performed under a gentle nitrogen stream to remove the water produced during imidization. Work-up is done by pouring the resulting solution into excess methanol and filtering. The precipitated polymer is washed several times with water and methanol, and then the polymer is dried at about 100° C. for around 12 hours in vacuo.

Example 54

Linear Polyaspartimides Derived from 2,2-Bis[4-(4-aminophenoxy)phenyl] Higher Diamondoids by the Michael Addition Reaction In a 100 mL three necked flask equipped with a magnetic stirrer, a reflux condenser, thermometer and nitrogen inlet, 0.553 g (1.25 mmol) of bis(3-ethyl-5-methyl-4-maleimidophenyl)methane (BEMM) is added to 3.5 mL of m-cresol. When all the BEMM is dissolved, 1.25 mmol of a diamine 2,2-bis[4-(4-aminophenoxy)phenyl] higher diamondoid is added. Then 0.1 mL of glacial acetic acid, used as a catalyst, is added into the mixture so that the above diamine is completely dissolved. The reaction mixture is then immersed in an oil bath maintained at 100-110° C. for about 100 hours to polymerize. The resulting polymer is isolated by pouring the viscous reaction mixture into excess ethanol under vigorous stirring. The polymer precipitate is collected by filtration and washed thoroughly with ethanol and extracted with hot ethanol using a Soxhlet extractor and subsequently dried in a vacuum oven at 70° C. for about 24 hours.

Example 55

4-(1-Higher Diamondcidyl)-1,3-Benzenediols from Brominated Compounds

A suitable brominated higher diamondoid (0.046 mole), resorcinol (5.51 g, 0.05 mole), and benzene (50 mL) are combined in a reaction flask equipped with a nitrogen inlet, a condenser fitted with a caustic scrubber, and a stirrer. This mixture is heated to reflux and for about 72 hours to allow for reaction under a constant nitrogen purge to assist in the removal of HBr formed. The reaction mixture is cooled to ambient temperature and the higher diamondoidyl substituted resorcinol is crystallized from solution. Residual resorcinol is removed by precipitating a solution of the product in methanol into warm water followed by filtrating and washing with water. Subsequent purification to a polymerization quality monomer is accomplished by vacuum drying to remove residual water, recrystallizing from toluene, and finally subliming to afford the product.

Example 56

4-(1-Higher Diamondoidyl)-1,3-Bis(4-aminophenoxy)benzene from 4-(1-Higher Diamondoidyl)-1,3-Benzenediol A mixture of a 4-(1-higher diamondoidyl)-1,3-benzenediol (13 mmol), p-chloronitrobenzene (4.53 g, 28.8 mmol), potassium carbonate (4.3 g, 31.2 mmol) and dry N,N-dimethylformamide (DMF, 30 mL) is refluxed for about 8 hours. The mixture is then cooled and poured into a methanol-water solution (1:1 by volume). The crude product is recrystallized from glacial acetic acid.

Hydrazine monohydrade (10 mL) is added dropwise to a mixture of the above product (4-(1-higher diamondoidyl)-1,3-bis(4-nitrophenoxy)benzene, 12.3 mmol), ethanol (25 mL), and a catalytic amount of 10% palladium on activated carbon (Pd/C, 0.05 g) at the boiling temperature. The reaction mixture is refluxed for about 24 hours, and the diamine product is precipitated during this period. The mixture is then added to a sufficient amount of ethanol to dissolve the diamine product and filtered to remove Pd/C. After cooling, the recipitated crystals are isolated by filtration and recrystallized from 1,2-dichlorobenzene to afford a pure diamine product.

Example 57

4-(1-Higher Diamondoidyl)-1,3-Bis(4-trimellitimidophenoxy)benzene from 4-(1-Higher Diamondoidyl)-1,3-Bis(4-aminophenoxy)benzene A flask is charged with 1.73 mmol of a 4-(1-higher diamondoidyl)-1,3-bis(4-aminophenoxy)benzene, 0.68 g (3.54 mmol) of trimellitic anhydride, and 5 mL of DMAc. The mixture is stirred at room temperature for about 5 hours under argon atmosphere. While continuing to maintain agitation and room temperature, 2.4 mL of acetic anhydride and 1.5 mL of pyridine are added incorporating for about 1 hour. Afterwards the mixture is heated at 100° C. for about 4 hours and then cooled and poured into methanol. The precipitate is filtered off and is purified by extraction with hot ethanol using a Soxhlet extractor and subsequently dried in a vacuum oven at 70° C. for 24 hours to afford diimide-dicarboxylic acid: 4-(1-higher diamondoidyl)-1,3-bis(4-trimellitimidophenoxy)benzene.

Example 58

Polyamide-imides Derived from 4-(1-Higher Diamondoidyl)-1,3-Bis(4-trimellitimidophenoxy)benzene by Solution Polycondensation A mixture of the diimide-dicarboxylic acid (4-(1-higher diamondoidyl)-1,3-bis(4-trimellitimidophenoxy)benzene, 0.7 mmol), 0.362 g of a diamine (2,2-bis[4-(4-aminophenoxy)phenyl]hexafluoropropane, 0.7 mmol), 0.25 g of calcium chloride, 0.6 mL of triphenyl phosphite, 0.6 mL of pyridine, and 3.0 mL of NMP is heated with stirring at 100° C. for about 2 hours under argon stream. After cooling, the reaction mixture is poured into a large amount of methanol with constant stirring, producing a precipitate that is washed thoroughly with hot water and methanol, collected on a filter, and dried at 100° C. under vacuum for 24 hours to afford a pure polyamideimide containing higher diamondoid components in the polymer backbone.

Example 59

Poly(aryl ethers) Derived from 4-(1-Higher Diamondoidyl)-1, 3-Benzenediols by Nucleophilic Aromatic Substitution Polymerization A 4-(1-higher diamondoidyl)-1,3-benzenediol (20.5 mmol) and 4,4'-difluorobenzophenone (4.468 g, 20.5 mmol) mixture is dissolved in 35 mL DMAc and 10 mL toluene in a reaction flask fitted with a nitrogen blanket, mechanical stirrer, and a Dean-Stark trap. To this mixture $K_2CO_3$ (2.969 g, 21.48 mmol) is added while stirring and heating to reflux. Reflux is held at around 130° C. for about 1 hour followed by the gradual removal of toluene from the reaction flask until the flask temperature reaches around 160° C. (ca. 2 hours). The reaction mixture is maintained at 160° C. for 10 hours and then cooled to ambient temperature. The polymer solution is diluted with chloroform, filtered to remove the inorganic salts, acidified, and then precipitated into methanol. Filtration and drying of the product at about 120° C. under vacuum gives the homopolymer.

Example 60

Co-Polymerization from 4-(1-Higher Diamondoidyl)-1,3-Benzenediols and 2,2-Bis(4-Hydroxyphenyl)propane by Nucleophilic Aromatic Substitution Co-polymerizations are carried out with different molar ratios of comonomers (2,2-bis(4-hydroxyphenyl)propane and a 4-(1-higher diamondoidyl)-1,3-benzenediol) using either DMAc or tetramethylene sulfone (sulfolane) as solvent. For instance, a 4-(1-higher diamondoi lyl)1.3-benzenediol (10.25 mmol) and 2,2-bis(4-hydroxyphenyl)propane (10.25 mmol) and 4,4'-difluorobenzophenone (4.468 g, 20.5 mmol) can be dissolved in 35 mL DMAc and 10 mL toluene in a reaction flask fitted with a nitrogen blanket, mechanical stirrer, and a Dean-Stark trap. To this mixture $K_2CO_3$ (2.969 g, 21.48 mmol) is added while stirring and heating to reflux. Reflux is held at around 130° C. for about 1 hour followed by the gradual removal of toluene from the reaction flask until the flask temperature reaches around 160° C. (ca. 2 hours). The reaction mixture is maintained at 160° C. for 10 hours and then cooled to ambient temperature. The polymer solution is diluted with chloroform, filtered to remove the inorganic salts, acidified, and then precipitated into methanol. Filtration and drying of the product at about 120° C. under vacuum gives the copolymer. If sulfolane is used as the solvent, the co-polymers are Soxhlet extracted with methanol to remove solvent and salts from the insoluble polymer.

Example 61

Poly(3-benzyloxypropyl malate-co-ethyl Higher Diamondyl Malate (85/15) from 3-Benzyloxypropylmalolactonate and Ethyl Higher Diamondoidyl Malolactonate by Anionic Ring-Opening Co-Polymerization A flask is charged with a mixture of 3-benzyloxypropylmalolactonate (85 mol %), ethyl higher diamondoidyl malolactonate (15 mol %) and tetraethylammonium benzoate ($10^{-3}$ eq. per mole of total moles of the co-monomers, acting as an initiator of the anionic ring-opening co-polymerization) under nitrogen. The mixture is then well stirred and warmed to 37° C. under nitrogen atmosphere and is maintained at this temperature for 15 days. After completion of the co-polymerization reaction, the copolymers are collected and washed with small amount of water, ethanol, and dried in vacuum for about 24 hours.

Example 62

Higher Diamondoidyl Propenyl Ether from Monohydroxylated Compounds

To a 150 mL round bottom flask are added a monohydroxylated higher diamondoid (2 mmol) and 3-bromo-1-propene (2 mmol) and 50 mL dry DMSO. The mixture is stirred and heated to about 100° C. under nitrogen atmosphere for a few hours. After completion of the reaction, the reaction mixture is poured into water (50 mL) and is extracted with ethyl ether or chloroform (3×50 mL). The combined organic layer is washed with water, dried over anhydrous $Na_2SO_4$, filtered, and the solvent is evaporated to give a crude product. The resulting crude product is purified by chromatography to afford higher diamondoidyl propenyl ether monomer suitable for polymerization.

Example 63

Higher Diamondoidyl Propynyl Ether from monohydroxylated Compounds

To a 150 mL round bottom flask the following is added, a monohydroxylated higher diamondoid (2 mmol), a 3-bromo-1-propyne (2 mmol), and 50 mL dry DMSO. The mixture is stirred and heated to about 100° C. under nitrogen atmosphere for a few hours. After completion of the reaction, the reaction mixture is poured into water (50 mL) and extracted with ethyl ether or chloroform (3×50 mL). The combined organic layer is washed with water, dried over anhydrous $Na_2SO_4$, filtered, and the solvent evaporated to give a crude product. The resulting crude product is purified by chromatography to afford higher diamondoidyl propynyl ether monomer suitable for polymerization.

Example 64

Higher Diamondoidyl Acryloyl Ester from monohydroxylated Compounds

To a 150 mL round bottom flask the following is added, a monohydroxylated higher diamondoid (2 mmol) and acryloyl chloride (2 mmol) and 50 mL dry THF. The mixture is stirred and heated to reflux under nitrogen atmosphere for a few hours. After completion of the reaction, the solvent is evaporated to dryness and the resulting crude product is purified by chromatography to afford higher diamondoidyl acryloyl ester monomer suitable for polymerization.

Example 65

Higher Diamondoidyl Monocarboxylic-Acid Propenyl Ester from Activated Monocarboxylic (Acid Chloride) Compounds 0.017 mole of a suitable monocarboxylated higher diamondoid is mixed with 4.2 g $PCl_5$ in a 50-mL flask equipped with a stirrer and a reflux condenser. The reaction starts after 30-60 seconds with liquefaction of the reaction mixture. The mixture is heated for an additional about 1 hour while stirring on a steam bath. The $POCl_3$ formed during reaction is distilled off under vacuum. The remaining acid chloride residue is cooled with ice water and 2-propen-1-ol (0.017 mole) is added dropwise. The mixture is heated for an additional 1 hour on a steam bath, cooled, and then poured into 50 mL water. The ester is taken up with ethyl ether and then washed with an aqueous potassium carbonate solution and water. After drying, fractionation is carried out over calcium chloride and under vacuum to afford propenyl ester suitable for polymerization.

Example 66

Higher Diamondoidyl Monocarboxylic-Acid Propynyl Ester from Activated Monocarboxylic (Acid Chloride) Compounds 0.017 mole of a suitable monocarboxylated higher diamondoid is mixed with 4.2 g $PCl_5$ in a 50-mL flask equipped with a stirrer and a reflux condenser. The reaction starts after 30-60 seconds with liquefaction of the reaction mixture. The mixture is heated for an additional about 1 hour while stirring on a steam bath. The $POCl_3$ formed is distilled off under vacuum. The acid chloride left behind as a residue is cooled with ice water, and dropwise 2-propyn-1-ol (0.017 mole) is added. The mixture is heated for an additional 1 hour on the steam bath, cooled and then poured into 50 mL water. The ester is taken up with ethyl ether and then washed with potassium carbonate aqueous solution and water. After drying, fractionation is carried out over calcium chloride under vacuum to afford propynyl ester monomer suitable for polymerization.

Example 67

Higher Diamondoidyl Monocarboxylic-Acid Propenyl Amide from Activated Monocarboxylic (Acid Chloride) Compounds 0.017 mole of a suitable monocarboxylated higher diamondoid is mixed with 4.2 g $PCl_5$ in a 50-mL flask equipped with a stirrer and a reflux condenser. The reaction starts after 30-60 seconds with liquefaction of the reaction mixture. The mixture is heated for an additional 1 hour while stirring on a steam bath. The $POCl_3$ formed is distilled off under vacuum. The resulting acid chloride residue is cooled with ice water, and 3-amino-1-propene (0.017 mole) is added dropwise. The mixture is heated for an additional 1 hour on the steam bath, cooled and then poured into 50 mL water. The amide is taken up with ethyl ether and then washed with potassium carbonate aqueous solution and water. After drying, purification of the crude amide is conducted by chromatography to afford propenyl amide suitable for polymerization.

Example 68

Higher Diamondoidyl Monocarboxylic-Acid Propynyl Amide from Activated Monocarboxylic (Acid Chloride) Compounds 0.017 mole of a suitable monocarboxylated higher diamondoid is mixed with 4.2 g $PCl_5$ in a 50-mL flask equipped with a stirrer and a reflux condenser. The reaction starts after 30-60 seconds with liquefaction of the reaction mixture. The mixture is heated for an additional 1 hour while stirring on a steam bath. The $POCl_3$ formed is distilled off under vacuum. The acid chloride left behind as a residue is cooled with ice water, and 3-amino-1-propyne (0.017 mole) is added dropwise. The mixture is heated for an additional 1 hour on the steam bath, cooled, and then poured into 50 mL water. The amide is taken up with ethyl ether and then washed with potassium carbonate aqueous solution and water. After drying, purification of the crude amide is conducted by chromatography to afford propynyl amide suitable for polymerization.

Example 69

Monoacryloylaminated Higher Diamondoids from Monoaminated Compounds

To a 150 mL round bottom flask are added a monoaminated higher diamondoid (2 mmol) and acryloyl chloride (2 mmol) and 50 mL dry THF. The mixture is stirred and heated to reflux under nitrogen atmosphere for a few hours. After completion of the reaction, which is conveniently monitored by TLC or GC analysis, the solvent is evaporated to dryness and the resulting crude product is purified by chromatography to afford higher diamondoidyl acryloyl amide monomer suitable for polymerization.

Example 70

Higher Diamondoidyl Propenyl Amide from Monoaminated Compounds

To a 150 mL round bottom flask the following is added, a monoaminated higher diamondoid (2 mmol) and 3-bromo-1-propene (2 mmol) and 50 mL dry DMSO. This mixture is stirred and heated to reflux under nitrogen atmosphere for a few hours. After completion of the reaction, which is conveniently monitored by TLC or GC analysis, the reaction mixture is poured into water (50 mL) and extracted with ethyl ether or chloroform (3×50 mL). The combined organic layer is washed with water, dried over anhydrous $Na_2SO_4$, filtered, and the remaining solvent is evaporated to give a crude product. The resulting crude product is purified by chromatography to afford higher diamondoidyl propenyl amide monomer suitable for polymerization.

Example 71

Higher Diamondoidyl Propynyl Amide from Monoaminated Compounds

To a 150 mL round bottom flask the following is added, a monoaminated higher diamondoid (2 mmol) and 3-bromo-1-propyne (2 mmol) and 50 mL dry DMSO. The mixture is stirred and heated to reflux under nitrogen atmosphere for a few hours. After completion of the reaction, which is conveniently monitored by TLC or GC analysis, the reaction mixture is poured into water (50 mL) and extracted with ethyl ether or chloroform (3×50 mL). The combined organic layer is washed with water and dried over anhydrous $Na_2SO_4$, filtered, and the solvent is evaporated to give a crude product. The resulting crude product is purified by chromatography to afford higher diamondoidyl propynyl amide monomer suitable for polymerization.

Example 72

Phenyl Higher Diamondoid-Modified PEGs [Poly(ethylene glycol)s] from Alcoholate of Higher Diamondoidylphenol To a stirred solution of a poly(ethylene gylcol) (PEG, 1 mmol) in 15 mL dichloromethane, 1 mL of triethylamine is added. This solution is cooled in an ice bath under nitrogen atmosphere. Then 1 g of 4-toluenesulfonylchloride (5.2 mmol) is added. The reaction is continued st 0° C. for 2 hours and then the mixture stirred at room temperature overnight. The product is precipitated in diethyl ether. An additional recrystallization from ethanol is performed in order to remove the triethylammonium chloride formed during the reaction according a pure PEG tosylate.

Under a nitrogen atmosphere, a higher diamondylphenol (4 mmol) dissolved in 70 mL of freshly distilled dichloromethane is added dropwise to 0.24 g of sodium hydride suspended in 30 mL of distilled dichloromethane. The solution is stirred for 2 hours at room temperature before adding dropwise the PEG tosylate (a little excess) dissolved in 50 mL of dichloromethane. The reaction mixture is kept at 40° C. for 24 hour. The obtained polymer is precipitated in ethyl ether, recrystallized from ethanol and stored at 4° C.

Example 73

Design of Diamonds Containing Polymers or Co-Polymers

Polymers such as polyamides, polyimides, polyesters, polycarbonates which are easily processed soluble, mechanically strong and thermally stable are very important materials in wide range of industries, such as the microelectronics industry. Introduction of different pendant groups such as cardo groups along the polymer backbone has been shown to impart greater solubility and enhanced rigidity as well as better mechanical and thermal properties of the resulting polymers. Of particular interest is introducing cage hydrocarbons into the polymer chain because such cardo groups show significant characteristics such as high cardo/hydrogen ratio, high thermal and oxidative stability, rigidity, hydrophobicity, and transparency. Previous studies involved the introduction of only adamantyl groups because of the limited availability of other lower diamondoid hydrocarbons (diamantane and triamantane) and the unavailability of higher diamondoid hydrocarbons (tetramantane, pentamantane, hexamantane and the like). Incorporation of adamantyl groups into the polymer backbone resulted in great improvements in the solubility, thermal stability and other physical properties of the resulting polymers. We now describe a series of polymers and co-polymers containing higher diamondoid hydrocarbon moieties in the polymer backbone with improved physical properties and processability. It should be pointed out that only examples based on iso-tetramantane are given below in Examples 74-79. This does not mean that iso-tetramantane is the only choice for these applications. All other higher diamondoids and their isomers and/or their multifunctional derivatives are good candidates for such applications.

Example 74

Figure 35:
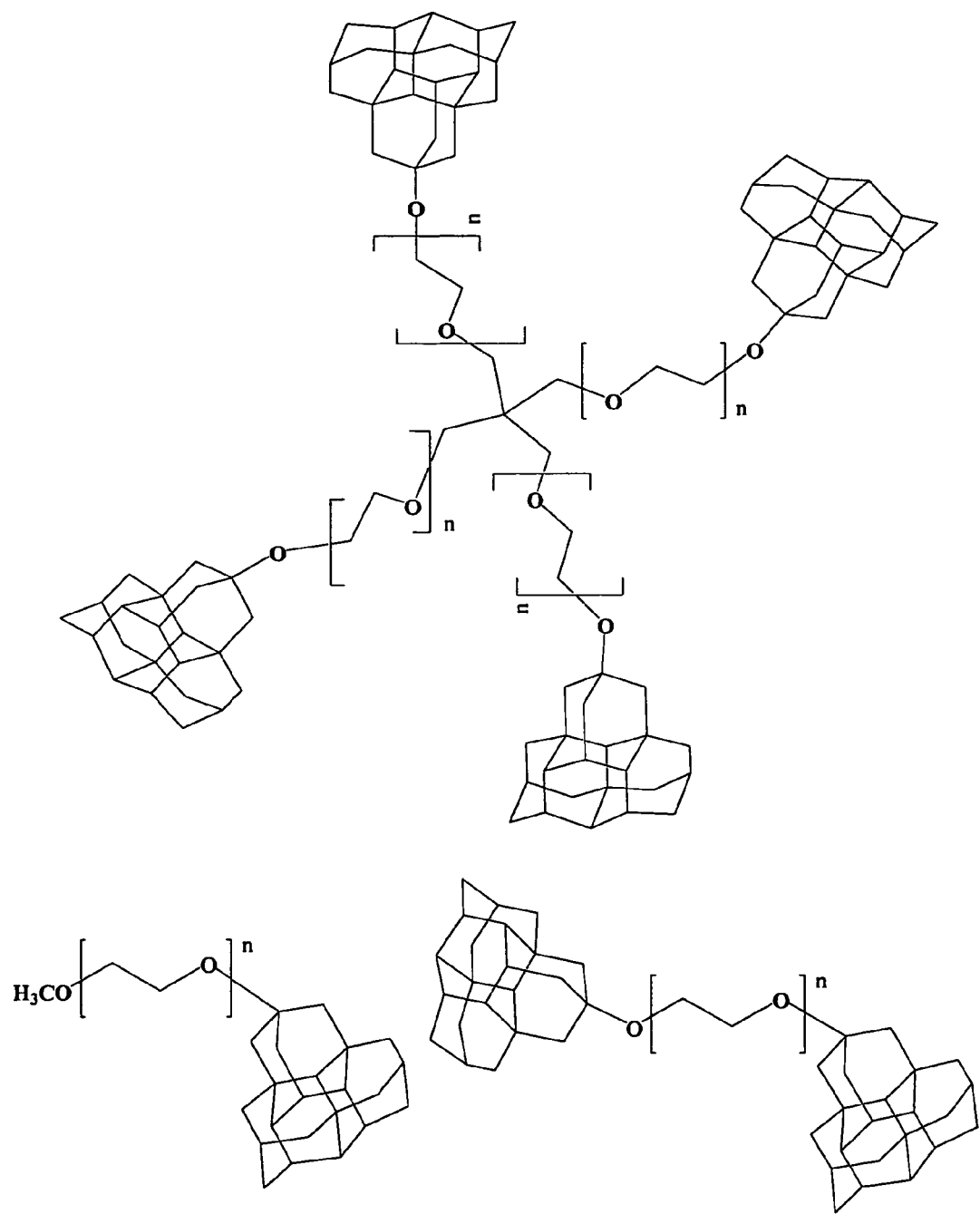

Water Soluble Poly)ethylene glycol)s (PEGs) Containing Higher Diamondoids for Potential Drug Delivery Purposes Host-guest interactions are very important processes in human biology. The water solubility of drugs is a key factor in determining their medical efficacy in living tissue. In order to enhance drug efficiency, poly(ethylene glycol)s (PEGs) can be modified by higher diamondoid hydrocarbon compounds at their OH terminal ending(s). These hydrophobic groups may be selected based upon their potentially strong interactions with other groups in "cavities" formed in PEG polymer chains and thus can help deliver the drugs which have low solubility in water. Examples are shown in FIG. 35.

Example 35

Carbon-Rich Polymers for Nanolithography

Rapid advances in the miniaturization of microelectronic devices require the development of new imageable polymeric materials for 193 nm microlithography (The National Technology Roadmap for Semiconductors, Semiconductor Industry Association (SIA), San Jose, Calif., 1997). The design challenge for 193 nm resist materials is the trade-off between plasma-etch resistance (which requires a high carbon/hydrogen ratio in the polymer structure) and optical properties for lithographic performance.

Figure 36:
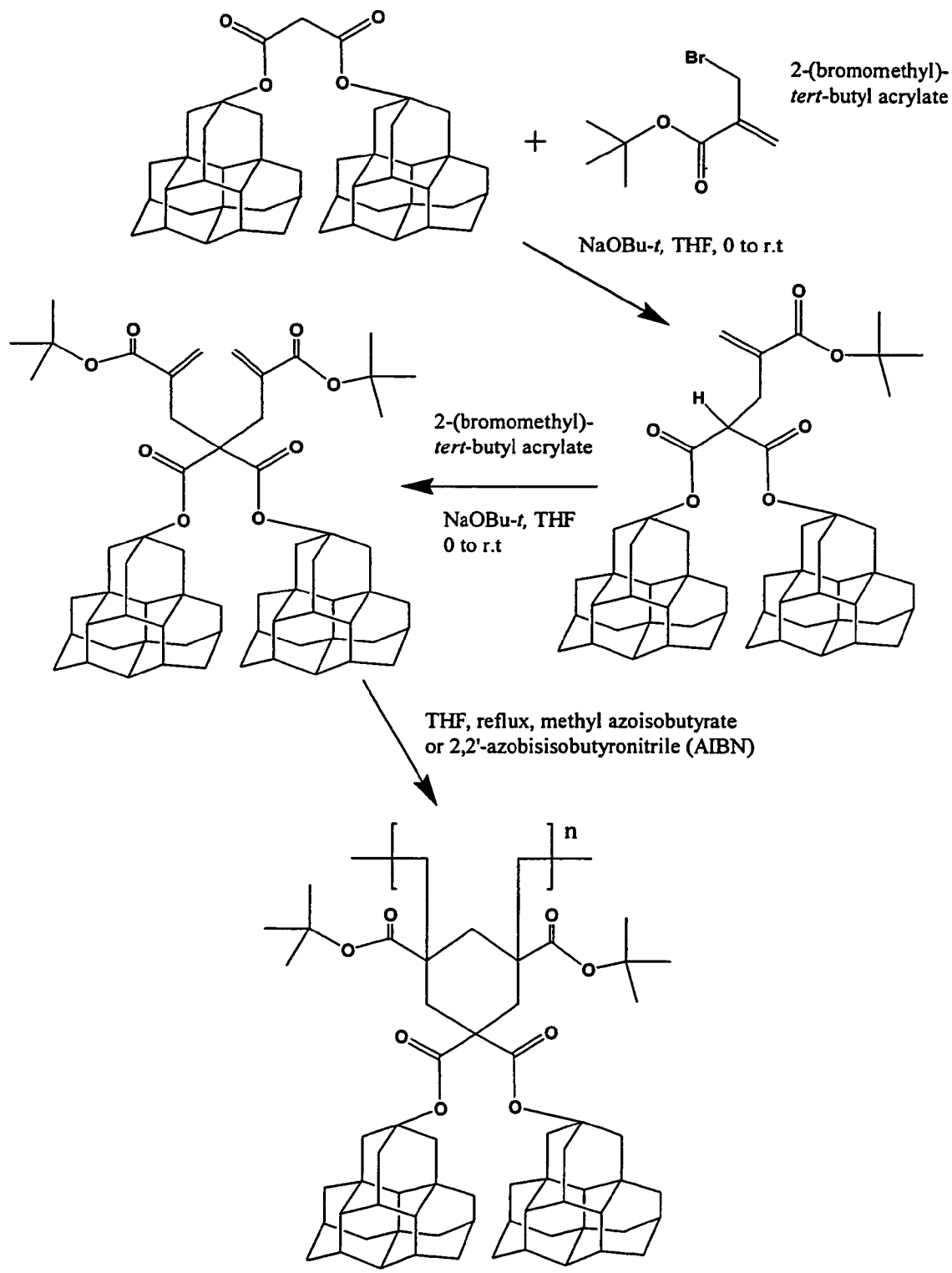

In FIG. 36 we show the design of a carbon-rich cyclopolymer incorporating both imageable functionalities (tert-butyl esters) for chemical amplification, and high etch-resistance moieties (higher diamondoids such as tetramantanes, pentamantanes, hexamantanes and the like). To adjust the physical properties of polymers, such as wettability and adhesion properties, a wide range of co-polymers can be prepared. This was shown to be feasible for adamantine-containing cyclopolymers and co-polymers by D. Pasini, E Low and J. M. J. Fréchet (Advanced Materials, 12, 347-351 (2000)), and those materials showed excellent imaging properties. In addition, since the synthetic routes involve free radical polymerization techniques, metal contamination of the underlying semiconductor substrates is not an issue, as is the case for polymers based on norbornene (Chemical of Materials, 10 3319 (1998); 10, 3328 (1998)). Furthermore, adamantane-containing temperature ($T_d$) and good film-forming properties. Polymers based on higher diamondoids would be expected to have even better properties.

Example 76

Soluble Higher Diamondoid-Containing Polyesters Based on Diamondoid Bisphenol

Figure 37B:
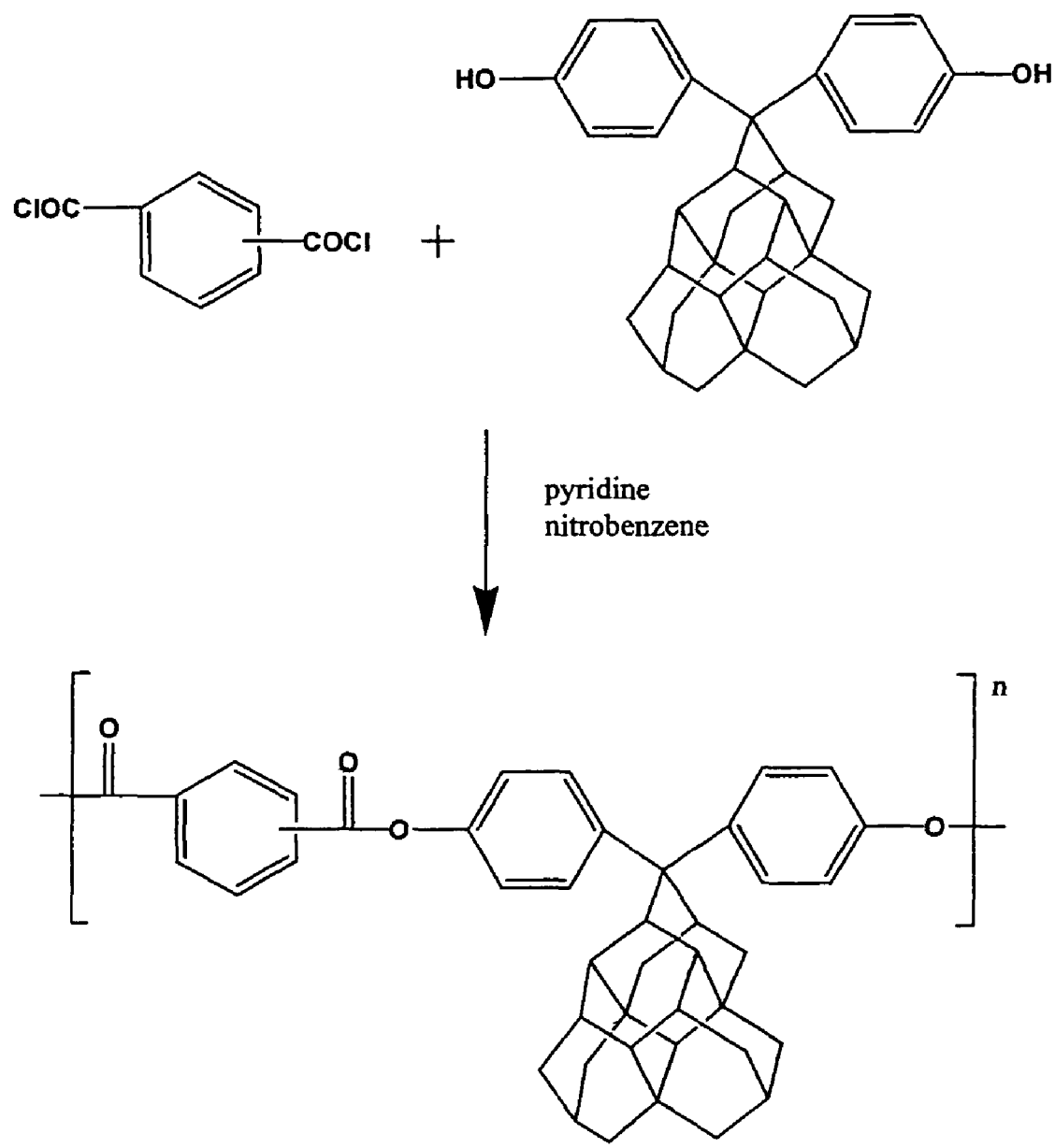

Polyarylates derived from bisphenol and iso/terephthalic acid are well accepted as highly thermally stable materials. However, polyarylates are generally difficult to process because of their limited solubility in organic solvents and their high melting temperatures or high $T_g$'s by virtue of their rigid structures. It has been reported that incorporation of bulky pendant cardo groups, such as adamantly groups, into polymer backbones, results n enhanced thermal properties of the polymers. compared with polymers containing aromatic bisphenols (FIG. 37A). As an example of the type of polymer, FIG. 37B shows the design of an iso-tetramantane containing polyester.

Example 77

Soluble Higher Diamondoid Containing Polyamides Based on Diamondoid Diamines

Aromatic polyamides attract much interest because of their high-temperature resistance and mechanical strength. However, the applications of polyamides are limited by processing difficulties arising from their low solubility in organic solvents and their high glass transition or melting temperature. A number of successful approaches to increasing the solubility and processability of polyamides, without sacrificing their thermal stability, employ the introduction of flexible or non-symmetrical linkages into the polymer backbone or the incorporation of bulky substituents, such as pendant groups, into the polymer backbone. The inter-chain interaction of the polymers can be decreased by the introduction of bulky pendant groups, resulting in improved solubility of the polymers. Generally, the incorporation of pendant groups results in amorphous materials with increased solubility in common organic solvents.

Figure 38:
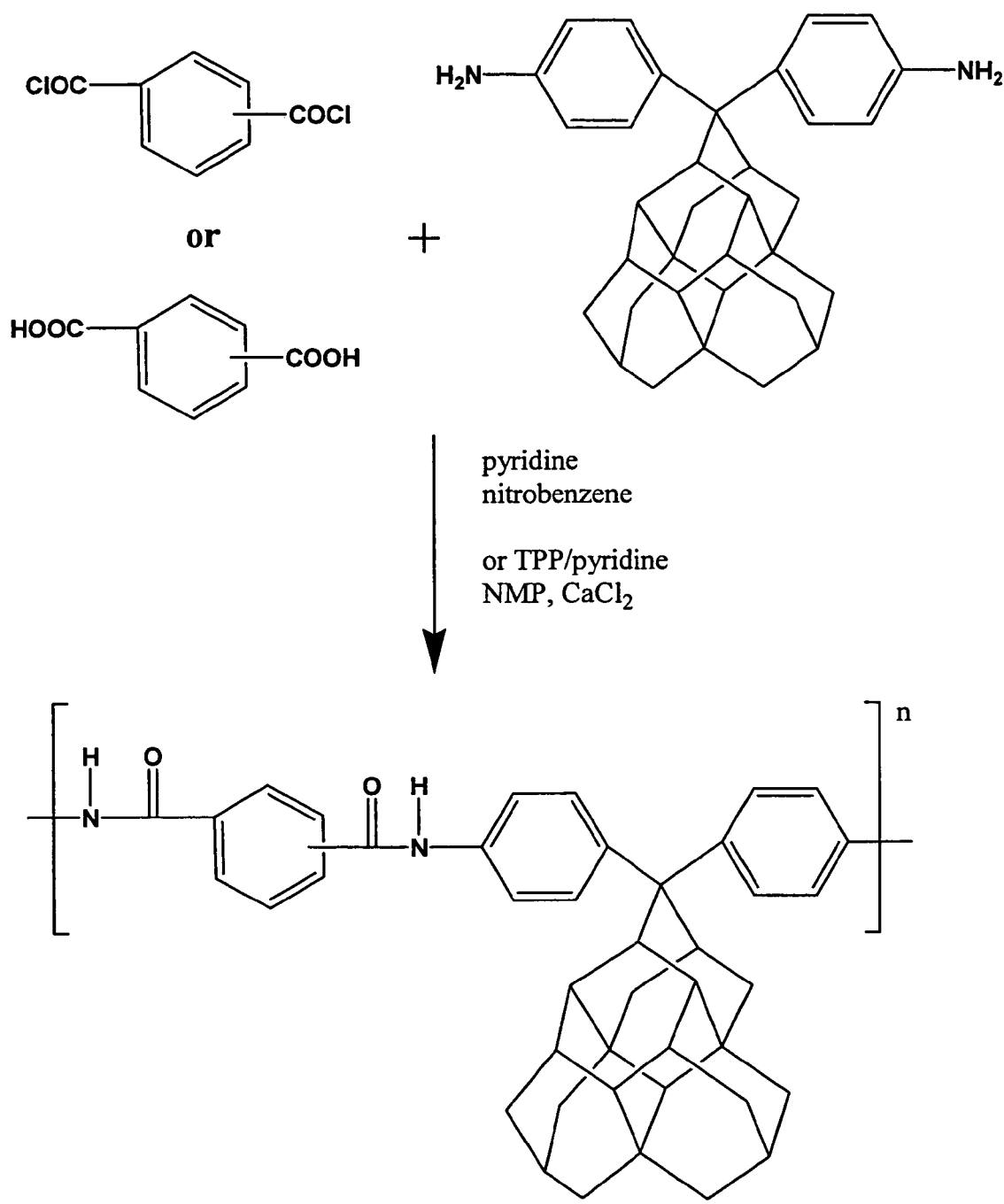

FIG. 38 presents an example of this design which incorporates iso-tetramantane groups in the polyamide backbone.

Example 78

Soluble Diamondoid-Containing Polyimides Based on Diamondoid Diamines

Figure 39A:
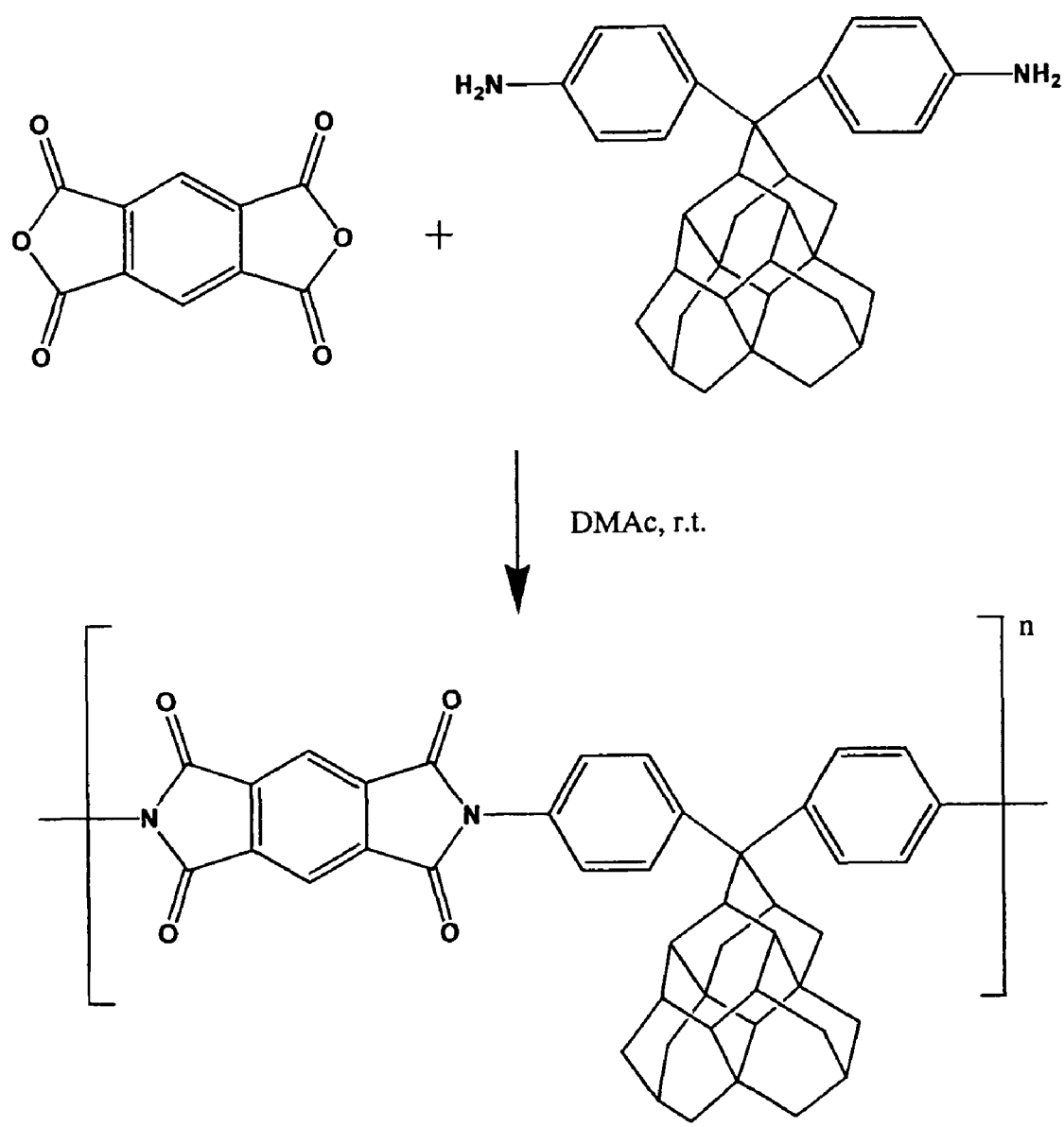
Figure 40:
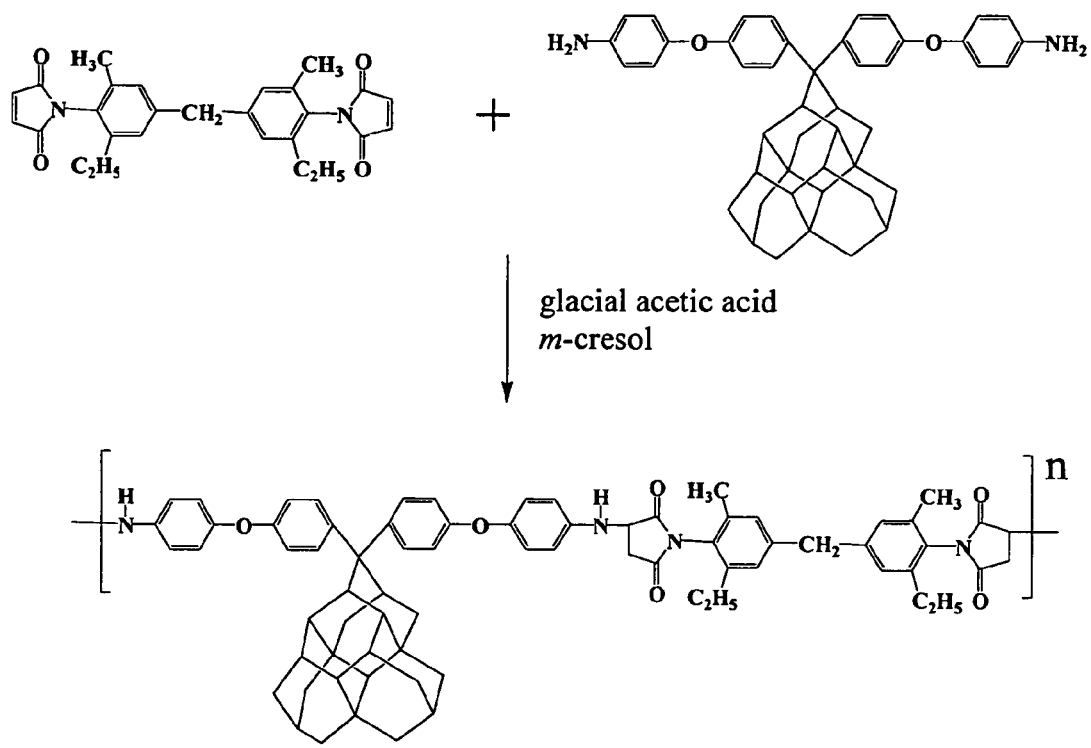

The outstanding properties of aromatic polyimides, such as excellent thermo-oxidative stability and superior chemical resistance, led to the use of polyimides in many applications such as insulating materials for electronics, semipermeable membranes for gas separations, and high-temperature adhesives and coatings. (J. M. Sonnett, T. P. Gannett, Polyimides: Fundamental and Applications", M. K. Ghosh and K. L. Mittal, Ed., Marcel Dekker, New York, 1996). However, in general, aromatic polyimides are insoluble and intractable and are, only processable under extreme conditions. Therefore, a great deal of effort has focused on increasing their processability while minimizing loss of their thermal stability. To overcome these processing problems, flexible or bulky groups, such as adamantly groups, into the polymer backbone was shown to increase both thermal stability and solubility in organic solvents, thus improving the processability of polyimides. In addition, since such cage hydrocarbon groups are bulky, their incorporation into polymer backbones significantly improves the penetration of solvent molecules into the polymer, thus increasing solubility. As an example, we now present a polyimide containing iso-tetramantane groups along its polymer backbone (FIG. 39A), and a design of polyaspartimide containing iso-tetramantyl groups (FIG. 40). It should be noted that the dianhydride could be non-aromatic or other aromatic dianhydrices as shown in FIG. 39B, for example.

Example 79

Figure 41:
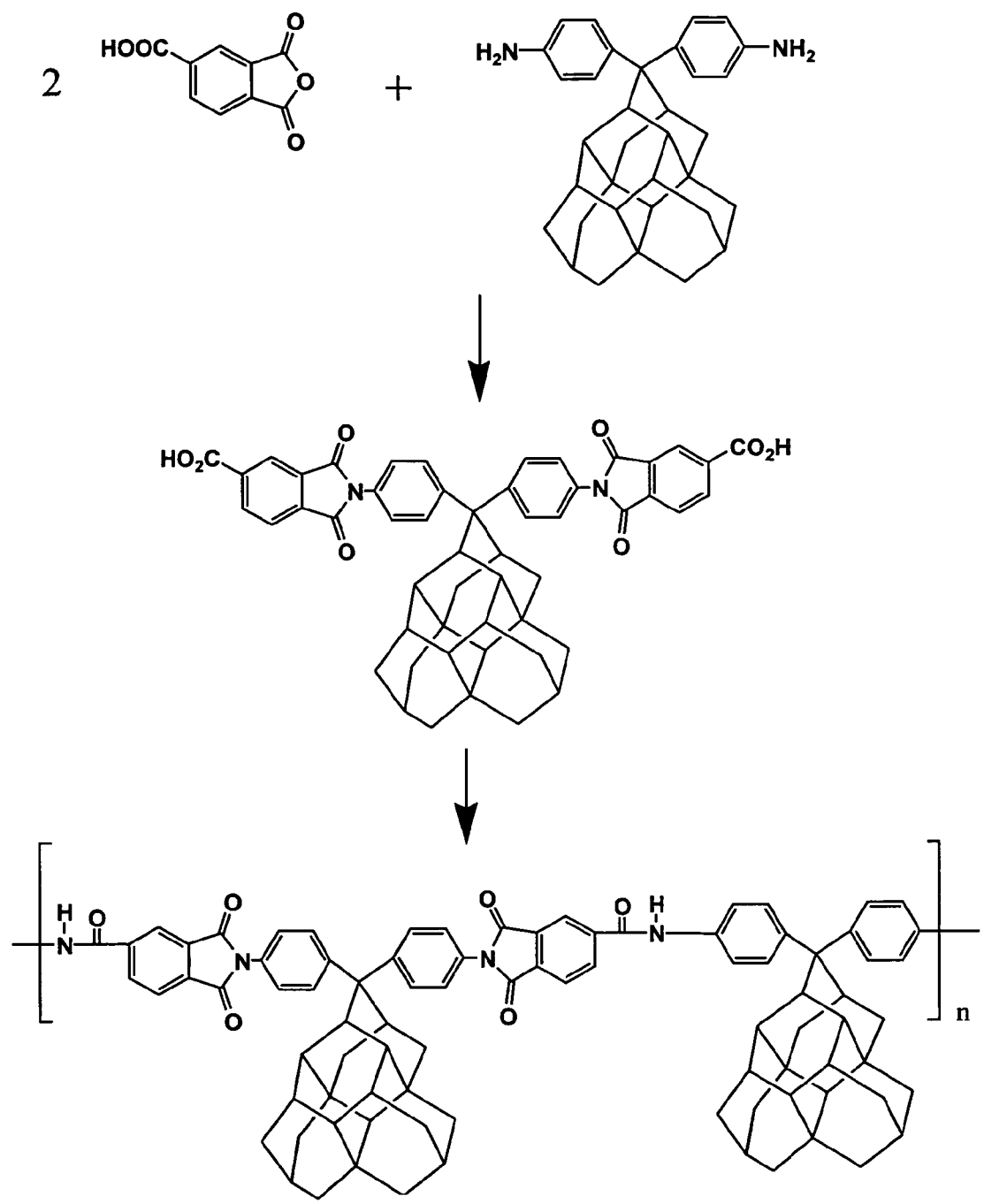

Soluble Higher Diamondoid Containing Polyamide-imides Based on Higher Diamondoid Diamide-Dicarboxylic Acids and Diamines Aromatic polyimides are recognized as a class of high performance materials because of their remarkable thermal and oxidative stabilities and their excellent electrical and mechanical properties, even during long periods of operation. Unfortunately, strong interactions between polyimide chains and their rigid structure make them intractable. Poor thermoplastic fluidity and solubility are the major problems for wide applications of polyimides. On the other hand, polyamides have the advantage of good solubility and processability, as do polyetherimides. Therefore, polyamide-imide or polyetherimide might be the most useful materials, combining the advantages of both polyimides (such as high-temperature stability) and polyamides (such as good processability). In combination with the advantages of diamondoid hydrocarbons, we present a sample design of a polyamide-imide containing iso-tetramantyl groups in the polymer chain (FIG. 41). The diamines involved in the polymerization reaction could be either higher diamondoid diamides such shown in FIG. 40 or other aromatic diamines or their combinations. Selected examples of aromatic diamines are presented in FIG. 42.

What is claimed is:

1. A higher diamondoid derivative containing a covalently-attached moiety replacing a hydrogen which is a polymerizable moiety or which can be converted to a polymerizable moiety.

2. The higher diamondoid derivative of claim 1 containing one or two polymerizable moieties.

3. The higher diamondoid derivative of claim 2 containing one polymerizable moieties.

4. The higher diamondoid derivative of claim 2 containing two polymerizable moieties.

5. The higher diamondoid derivative of claim 1 having the formula:

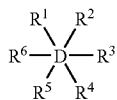

wherein D is a higher diamondoid nucleus, and
$R^1$, $R^2$, $R^3$, $R^4$, $R^5$ and $R^6$ are independently selected from the group consisting of hydrogen and a polymerizable moiety; provided at least one of the R's is a polymerizable moiety.

6. The higher diamondoid derivative of claim 2 wherein the polymerizable moieties are selected from alkenyl, alkynyl, OH, $C_2H_3O$, SH, $NH_2$, $CO_2H$, $C_6H_5$, $C_6H_4NH_2$, $C_6H_4CO_2H$ or $C_6H_4OH$.

7. The higher diamondoid derivative of claim 2, wherein the one or more polymerizable moieties are attached to tertiary carbons of the higher diamondoid.

8. The higher diamondoid derivative of claim 5 wherein the higher diamondoid is tetramantane.

9. The higher diamondoid derivative of claim 5 wherein the higher diamondoid is pentamantane.

10. The higher diamondoid derivative of claim 5 wherein the higher diamondoid is hexamantane.

11. The higher diamondoid derivative of claim 5 wherein the higher diamondoid is heptamantane.

12. The higher diamondoid derivative of claim 5 wherein the higher diamondoid is octamantane.

13. The higher diamondoid derivative of claim 5 wherein the higher diamondoid is nonamantane.

14. The higher diamondoid derivative of claim 5 wherein the higher diamondoid is decamantane.

15. The higher diamondoid derivative of claim 5 wherein the higher diamondoid is undecamantane.

16. The higher diamondoid derivative of claim 5 wherein the polymerizable moiety has the structure:

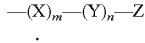

wherein
X is O, $NR^7$, OC(O), $NR^8C(O)$, C(O)O or $C(O)NR^9$, wherein $R^7$, $R^8$ and $R^9$ are independently hydrogen or alkyl;
Y is alkylene, arylene, alkarylene, heteroarylene or alkheteroarylene;
Z is alkenyl, alkynyl, OH, $C_2H_3O$, SH, $NH_2$, $CO_2H$, $C_6H_5$, $C_6H_4NH_2$, $C_6H_4CO_2H$ or $C_6H_4OH$
m is 0 or 1; and,
n is 0 or 1.

17. The higher diamondoid derivative of claim 16, wherein there is one or two polymerizable moieties on the derivative.

18. The higher diamondoid derivative of claim 17, wherein there is one polymerizable moiety on the derivative.

19. The higher diamondoid derivative of claim 17, wherein there are two polymerizable moieties on the derivative.

20. The higher diamondoid derivative of claim 16, wherein Z is selected from the group consisting of ethenyl, ethynyl, propenyl, propynyl, isobutenyl and butynyl.

21. The higher diamondoid derivative of claim 16, wherein Z is selected from a group consisting of OH and SH.

22. The higher diamondoid derivative of claim 16, wherein Z is selected from a group consisting of $NH_2$, $C_2H_3O$ and $CO_2H$.

23. The higher diamondoid derivative of claim 16, wherein Z is selected from a group consisting of $C_6H_5$, $C_6H_4NH_2$, $C_6H_4CO_2H$ and $C_6H_4OH$.

24. The higher diamondoid derivative of claim 16, wherein X is O, OC(O), $NR^7$, $NR^8C(O)$, C(O)O, or $C(O)NR^9$.

25. The higher diamondoid derivative of claim 16, wherein m is 0 and Y is alkylene or arylene.

26. The higher diamondoid derivative of claim 16, wherein m is 0 and Y is alkylene.

27. The higher diamondoid derivative of claim 16, wherein m is 0 and n is 0.

28. The higher diamondoid derivative of claim 24, wherein Y is —$CH_2$— or —$(CH_2)_2$—.

29. A higher diamondoid intermediate containing a covalently-attached moiety replacing a hydrogen which is a polymerizable moiety or which can be converted to a polymerizable moiety.

30. The higher diamondoid intermediate of claim 29 containing one or two intermediate moieties.

31. The higher diamondoid intermediate of claim 30 containing one intermediate moieties.

32. The higher diamondoid intermediate of claim 30 containing two intermediate moieties.

33. The higher diamondoid intermediate of claim 29 having the formula:

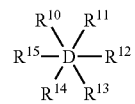

wherein
D is a higher diamondoid nucleus; and
$R^{10}$, $R^{11}$, $R^{12}$, $R^{13}$, $R^{14}$ and $R^{15}$ are independently selected from the group consisting of hydrogen and an intermediate moiety; provided at least one of the R's is an intermediate moiety.

34. The higher diamondoid intermediate of claim 33 wherein the intermediate is present in an amount of at least 100 ppm of the composition in which it is present.

35. The higher diamondoid intermediate of claim 34 wherein the intermediate moieties are selected from H, F, Cl, Br, I, OH, SH, $NH_2$, $NHCOCH_3$, NHCHO, $CO_2H$, $CO_2R'$, COCl, CHO, $CH_2OH$, =O, $NO_2$, —CH=$CH_2$, —C≡CH and $C_6H_5$; wherein R' is alkyl.

36. The higher diamondoid intermediate of claim 34, wherein the one or more intermediate moieties are attached to tertiary carbons of the higher diamondoid.

37. The higher diamondoid intermediate of claim 34 wherein the higher diamondoid is tetramantane.

38. The higher diamondoid intermediate of claim 34 wherein the higher diamondoid is pentamantane.

39. The higher diamondoid intermediate of claim 34 wherein the higher diamondoid is hexamantane.

40. The higher diamondoid intermediate of claim 34 wherein the higher diamondoid is heptamantane.

41. The higher diamondoid intermediate of claim 34 wherein the higher diamondoid is octamantane.

42. The higher diamondoid intermediate of claim 34 wherein the higher diamondoid is nonamantane.

43. The higher diamondoid intermediate of claim 34 wherein the higher diamondoid is decamantane.

44. The higher diamondoid intermediate of claim 34 wherein the higher diamondoid is undecamantane.

45. The higher diamondoid intermediate of claim 34 wherein $R^{10}$ is an intermediate moiety with at most one other R being an intermediate moiety.

46. The higher diamondoid intermediate of claim 45, wherein $R^{10}$ is OH.

47. The higher diamondoid intermediate of claim 45, wherein $R^{10}$ is Br.

48. The higher diamondoid intermediate of claim 45, wherein $R^{10}$ is $NH_2$.

49. The higher diamondoid intermediate of claim 45, wherein $R^{10}$ is $CO_2H$.

50. The higher diamondoid intermediate of claim 45, wherein $R^{10}$ is =O.

51. The higher diamondoid intermediate of claim 45, wherein $R^{10}$ is F.

52. The higher diamondoid intermediate of claim 45, wherein $R^{10}$ is Cl.

53. The higher diamondoid intermediate of claim 45, wherein $R^{10}$ is I.

54. The higher diamondoid intermediate of claim 45, wherein $R^{10}$ is $NO_2$.

55. The higher diamondoid intermediate of claim 45, wherein $R^{10}$ is $CO_2CH_2CH_3$.

56. The higher diamondoid intermediate of claim 45, wherein $R^{10}$ is COCl.

57. The higher diamondoid intermediate of claim 45, wherein $R^{10}$ is CHO.

58. The higher diamondoid intermediate of claim 45, wherein $R^{10}$ is $CH_2OH$.

59. The higher diamondoid intermediate of claim 45, wherein $R^{10}$ is $CH=CH_2$.

60. The higher diamondoid intermediate of claim 45, wherein $R^{10}$ is C≡CH.

61. The higher diamondoid intermediate of claim 45, wherein $R^{10}$ is $C_6H_5$.

62. The higher diamondoid intermediate of claim 45, wherein $R^{10}$ is SH.

63. The higher diamondoid intermediate of claim 45, wherein $R^{10}$ is $NHCOCH_3$.

64. The higher diamondoid intermediate of claim 45, wherein $R^{10}$ is NHCHO.

* * * * *